United States Patent
Alves et al.

(10) Patent No.: US 9,677,117 B2
(45) Date of Patent: Jun. 13, 2017

(54) BIOLUMINESCENT SUCCINATE DETECTION ASSAY

(71) Applicant: Promega Corporation, Madison, WI (US)

(72) Inventors: Juliano Alves, Madison, WI (US); Said A. Goueli, Fitchburg, WI (US); Hicham Zegzouti, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/715,528

(22) Filed: May 18, 2015

(65) Prior Publication Data

US 2016/0102338 A1    Apr. 14, 2016

Related U.S. Application Data

(60) Provisional application No. 62/061,635, filed on Oct. 8, 2014.

(51) Int. Cl.
| C12Q 1/66 | (2006.01) |
| C12Q 1/25 | (2006.01) |
| C12Q 1/26 | (2006.01) |
| C12Q 1/48 | (2006.01) |

(52) U.S. Cl.
CPC .............. *C12Q 1/66* (2013.01); *C12Q 1/25* (2013.01); *C12Q 1/26* (2013.01); *C12Q 1/48* (2013.01); *G01N 2333/9015* (2013.01); *G01N 2333/90245* (2013.01); *G01N 2333/91194* (2013.01); *G01N 2333/91235* (2013.01)

(58) Field of Classification Search
None
See application file for complete search history.

(56) References Cited

U.S. PATENT DOCUMENTS

| 4,923,796 | A | 5/1990 | Deneke et al. |
| 5,316,907 | A | 5/1994 | Lurie et al. |
| 5,618,665 | A | 4/1997 | Lurie et al. |
| 5,837,465 | A | 11/1998 | Squirrell et al. |
| 5,891,659 | A * | 4/1999 | Murakami ............. C12Q 1/66 435/15 |
| 6,132,983 | A | 10/2000 | Lowe et al. |
| 6,171,808 | B1 | 1/2001 | Squirrell et al. |
| 6,265,177 | B1 | 7/2001 | Squirrell et al. |
| 6,265,179 | B1 | 7/2001 | Zhou et al. |
| 6,599,711 | B2 | 7/2003 | Crouch et al. |
| 6,602,677 | B1 | 8/2003 | Wood et al. |
| 6,762,026 | B1 | 7/2004 | Sugiyama |
| 6,811,990 | B1 | 11/2004 | Corey et al. |
| 6,911,319 | B2 | 6/2005 | Crouch et al. |
| 7,247,435 | B2 | 7/2007 | Sugiyama |
| 7,332,278 | B2 | 2/2008 | Lowery et al. |
| 7,338,775 | B1 | 3/2008 | Ostanin et al. |
| 8,183,007 | B2 | 5/2012 | Zegzouti et al. |
| 8,802,411 | B2 * | 8/2014 | Zegzouti ............. C12Q 1/008 435/15 |
| 2004/0101922 | A1 | 5/2004 | Somberg et al. |
| 2004/0253685 | A1 | 12/2004 | Sessa |
| 2005/0208608 | A1 | 9/2005 | Raven et al. |
| 2006/0199238 | A1 | 9/2006 | Charter et al. |
| 2007/0015790 | A1 | 1/2007 | Cali et al. |
| 2008/0044813 | A1 | 2/2008 | Jansson et al. |
| 2008/0050762 | A1 | 2/2008 | Corey et al. |
| 2008/0305507 | A1 | 12/2008 | Yuan et al. |
| 2009/0075309 | A1 | 3/2009 | Gambhir et al. |
| 2009/0093519 | A1 | 4/2009 | Schein et al. |
| 2009/0298108 | A1 | 12/2009 | Schultz et al. |
| 2010/0227344 | A1 * | 9/2010 | Sun ...................... C12Q 1/32 435/8 |
| 2013/0109037 | A1 | 5/2013 | Goueli et al. |

FOREIGN PATENT DOCUMENTS

| CN | 1164259 | 11/1997 |
| CN | 1395619 | 2/2003 |
| EP | 0794260 | 9/1997 |
| JP | 2003070499 | 3/2003 |
| WO | WO 99/14336 | 3/1999 |
| WO | WO 00/24878 | 5/2000 |
| WO | WO 01/20002 | 3/2001 |
| WO | WO 01/31028 | 5/2001 |
| WO | WO 01/34830 | 5/2001 |
| WO | WO 03/040100 | 5/2003 |
| WO | WO 2004/027378 | 4/2004 |
| WO | WO 2004/027421 | 4/2004 |
| WO | WO 2009/079120 | 6/2009 |

(Continued)

OTHER PUBLICATIONS

"Technical Manual"; "TM#384" In: AMP-Glo TM Assay Instructions for Use of Products V5011, V5012 and V5013, Oct. 1, 2012, Promega, USA.

Berndsen et al., "A spectrophotometric assay for conjugation of ubiquitin and ubiquitin-like proteins," (2011) Anal. Biochem. 318: 102-110.

Boisclair et al., "Development of a Ubiquitin Transfer Assay for High Throughput Screening by Fluorescence Resonance Energy Transfer," (2000) J. Biomolec. Screen. 5: 319-328.

Branchini, B.R. et al., "Chemical synthesis of firefly luciferase analogs and inhibitors," Meth. Enzymol. (2000) 305:188-195.

Branchini, B.R. et al., "Naphthyl- and quinolylluciferin: green and red light emitting firefly luciferin analogues," Phohtochem. Photobiol. (1989) 49(5):689-695.

(Continued)

*Primary Examiner* — Ralph Gitomer

(74) *Attorney, Agent, or Firm* — Michael Best & Friedrich LLP

(57) ABSTRACT

Provided herein are methods for detecting and quantifying succinate in a sample. Also provided are methods for detecting and quantifying 2-oxoglutarate oxygenase enzyme and/or 2-oxoglutarate oxygenase activity in a sample and methods for screening for modulators of 2-oxoglutarate oxygenase activity.

12 Claims, 19 Drawing Sheets

(56) References Cited

FOREIGN PATENT DOCUMENTS

WO  WO 2013/063563  5/2013

OTHER PUBLICATIONS

Branchini, B.R. et al., "Yellow-green and red firefly bioluminescence from 5,5-dimethyloxyluciferin," J. Am. Chem. Soc. (2002) 124:2112-2113.

Brotz-Oesterhelt, et al., "Specific and Potent Inhibition of NAD+-dependent DNA Ligase by Pyridochromanones," (2003) J. Biol. Chem. 278: 39435-39442.

Carlson et al., "A Toolbox Approach to High-Throughput TR-FRET-Based SUMOylation and DeSUMOylation Assays," (2009) Assay and Drug Dev. Technol., 7: 348-355.

Chen, JJ et al., "Mechanistic Studies of Substrate-assisted Inhibition of Ubiquitin-activating Enzyme by Adenosine Sulfa mate Analogues," (2011) J. Biol. Chem., pp. 40867-40877.

Gietzen, K. et al., "A model for the regulation of the calmodulin-dependent enzymes erythrocyte Ca2+-transport ATPase and brain phosphodiesterase by activators and inhibitors," Biochem. J. (1982a) 207:541-548.

Gietzen, K. et al., "Compound 48/80: a powerful and specific inhibitor of calmodulin-dependent Ca2+-transport ATPase," IRCS Med. Sci. (1983) 11:12-13.

Gietzen, K. et al., "Effects of microtubular inhibitors on plasma membrane calcodulin-dependent Ca2+-transport ATPase," Mol. Pharmacol. (1982b) 22:413-420.

Gietzen, K. et al., "Effects of vinblastine and colchicine on calmodulin-dependent Ca2+-transport ATPase of human erythrocytes," IRCS Med. Sci. (1980) 8:396-397.

Gietzen, K. et al., "Inhibition of human erythrocyte Ca++-tmnsport ATPase by phenothiazines and butyrophenones," Biochem. Biophys. Res. Commun. (1980) 94:674-681.

Gietzen, K. et al., "R 24571: a new powerful inhibitor of red blood cell Ca++-transport ATPase and of calmodulin-regulated functions," Biochem. Biophys. Res. Commun. (1981) 101:418-425.

Gietzen, K., "Comparison of the calmodulin antagonists compound 48/80 and calmidazolium," Biochem. J. (1983) 216(3):611-616.

Glaser, P. et al., "The calmodulin-sensitive adenylate cyclase of Bordetella pertussis: cloning and expression in *Escherichia coli*," Mol. Microbiol. (1988) 2(1):19-30.

Golinska, M et al., "Adaptation to HIF-1 deficiency by upregulation of the AMP/ATP ratio and phosphofructokinase activation in hepatomas," 2011, BMC Cancer 11: 198, pp. 1-13.

Goueli, S. et al., "Abstract 164: High Throughput Homogenous Bioluminescent Assays for Monitoring the Concentrations of AMP ADP and ATP," American Association for Cancer Research, Annual Meeting, Mar. 31-Apr. 4, 2012, Chicago, Presented at the poster section 6, board 18, on Apr. 1, 2012, Retrieved from Internet <URL:http://www.promega.de/~media/Files/Resources/Posters/High%20Throughput%20Homogeneous%20Bioluminescent%20Assays%20for%20Monitoring%20AMP%20ADP%20and%20ATP%20Poster.pdf>.

Gururaja et al, "A Homogeneous FRET Assay System for Multiubiquitin Chain Assembly and Disassembly," (2005) Meth. Enzymol. 399: 663-682.

Haas, et al., "The Mechanism of Ubiquitin Activating Enzyme, A Kinetic and Equilibrium Analysis," (1982) J. Biol. Chem. 257: 10329-10337.

Hendricks et al., "An enzyme-coupled colorimetric assay for S-adenosylmethionine-dependent methyltransferases," (2004) Anal Biochem. 326: 100-105.

Hong, J. et al., "Anthrax edema factor potency depends on mode of cell entry," Biochem. Biophys. Res. Commun. (2005) 335(3):850-857.

Kim et al., "Aminoacyl-tRNA synthetases and tumorigenesis: more than housekeeping," (2011) Nature Rev Cancer, 11: 708-718.

Kim et al., "Analysis of in vitro SUMOylation using bioluminescence resonance energy transfer (BRET)," (2009) Biochem. Biophys. Res. Commun.382: 530-534.

Kobayashi, R. et al., "Ca2+-regulated modulator protein interacting agents: inhibitors of Ca2+-Mg2+-ATPase of human erythrocyte ghost," Biochem. Biophys. Res. Commun. (1979) 88:1037-1045.

Komander, D, "The emerging complexity of protein ubiquitination," 2009, Biochem. Soc.Trans. 37: 937-953.

Ladant, D. et al., "Characterization of the calmodulin-binding and of the catalytic domains of bordetella pertussis adenylate cyclase," J. Biol. Chem. (1989) 264(7):4015-4020.

Lee, R.T. et al., "Substrate-binding properties of firefly luciferase. II. ATP-binding site," Arch. Biochem. Biophys. (1970) 141:38-52.

Levin, R. et al., "Mechanism by which psychotropic drugs inhibits adenosine cyclic 3'-5'-monophosphate phosphodiesterase of brain,"Mol. Pharmacol. (1976) 12:581-589.

Lust, W. et al., "The enzymatic measurement of adenine nucleotides and P-creatine in picomole amounts," Analytical Biochemistry, vol. 110, No. 1, Jan. 1, 1981, pp. 258-266.

Marblestone, "Novel Approach for Characterizing Ubiquitin E3 Ligase Function," (2010) J. Biomol. Screening, 15: 1220-1228.

Perrett, D, "Comparative Performance of Ion Exchange and Ion-paired Reversed Phase High Performance Liquid Chromatography for the Determination of Nucleotides in Biological Samples," (1991) Biomed Chromatography 5: 207-211.

Resnick, S. et al., "In Vitro ATP Regeneration from Polyphosphate and AMP by Polyphosphate: AMP Phosphatransferase and Adenylate Kinase from Acinetobacter JohnsonII 210A," Applied and Environmental Microbiology, vol. 66, No. 5, May 1, 2000, pp. 2045-2051.

Ronner, P. et al., "Luminometric Assays of ATP, Phosphocreatine, and Creatine for Estimation of Free ADP and Free AMP," Analytical Biochemistry, vol. 275, No. 2, Nov. 15, 1999, pp. 208-216.

Rose et al., "A specific endpoint assay for ubiquitin (ubiquitin-activating enzyme)," (1987) Proc. Natl. Acad. Sci. USA 84: 1477-1481.

Sala-Newby, G. et al., "Engineering firefly luciferase as an indicator of cyclic AMP-dependent protein kinase in living cells," FEBS Lett. (1992) 30:241-244.

Schmutz, D. et al., "Rapid-simple measurement of ATP-sulfulylase activity in crude plant extracts using an ATP meter for bioluminescence determination," Anal. Biochem. (1982) 121:151-155.

Schultz, V. et al., "Bioluminometric assay of ADP and ATP at high ATP/ADP ratios: assay of ADP after enzymatic removal of ATP," Anal. Biochem. (1993) 215(2):302-304.

Shapiro et al., "High-Throughput Fluorescence Resonance Energy Transfer-Based Assay for DNA Ligase," 2011, 16: 486-493.

Steghens, J-P. et al., "Firefly luciferase has two nucleotide binding sites: effect of nucleoside monophosphate and CoA on the light-emission spectra," Biochem. J. (1998) 336:109-113.

Tanaka, S. et al., "A sensitive method for detecting AMP by utilizing polyphosphate-dependent ATP regeneration and bioluminescence reactions," Biomedical Engineering Journal, vol. 9 , No. 3, Dec. 1, 2001, pp. 193-197.

Taylor MR et al., "Kinetic Mechanism of Human DNA Ligase I Reveals Magnesium-dependent Changes in the Rate-limiting Step That Compromise Ligation Efficiency," (2011) J. Biol. Chem. 286: 23054-23062.

Tofaris, GK et al., "Ubiquitin ligase Nedd4 promotes α-synuclein degradation by the endosomal-lysosomal pathway," (2011) PNAS, 108: 17004-9.

Volpi, M. et al., "Antagonism of calmodulin by local anesthetics. Inhibition of calmodulin-stimulated calcium transport of erythrocyte inside-out membrane vesicles," Mol. Pharmacol. (1981) 20:363-370.

Wang, R et al., "Formulating a fluorogenic assay to evaluate S-adenosyl-L-methionine analogues as protein methyltransferase cofactors," Mol. BioSyst., 2011, 7, 2970-2981.

Watanabe, K. et al. "Specific inhibitor of a calcium dependent activation of brain cyclic AMP phosphodiesterase activity by vinblastine,"Experientia (1979) 35:1487-1489.

Wee, "Steady-State Kinetic Analysis of Human Ubiquitin-Activating Enzyme (E1) Using a Fluorescently Labeled Ubiquitin Substrate," (2000) J Protein Chem., 19: 489-498.

Weiss, B. et al., "Pharmacological regulation of calmodulin,"Ann. N.Y. Acad. Sci. (1980) 356:319-345.

(56) References Cited

OTHER PUBLICATIONS

Weiss, B. et al., "Rapid microassay of adenosine 3',5'-monophosphate phosphodiesterase activity," Analytical Biochemistry, vol. 45, No. 1, Jan. 1, 1972, pp. 222-235.
Weissman et al., "The predator becomes the prey: regulating the ubiquitin system by ubiquitylation and degradation," 2011, Nature Rev Mol Cell Biology 12:605-620.
Wilkie and Plater, "Novel Assays Harness the Drug Discovery Potential of Complex Ubiquitination Pathways," (2011) Millipore Corp., 8 pages.
Wolff, D.J. et al., "Calcium-dependent cyclic nucleotide phosphodesterase from brain: identification of phospholipids as calcium-independent activators," Arch. Biochem. Biophys. (1976) 173:720-731.
Yu, M. et al., "Rat liver ATP-sulfurylase: purification, kinetic characteristics, and interaction with arsenate, selenate, phosphate, and other inorganic oxyanions," Anal. Biochem. (1989) 269:156-174.
Ibanez, G. et al., "An enzyme-coupled ultrasensitive luminescence assay for protein methyltransferases", Analytical Biochemestry (2010) 401:203-210.
Sgaramella, V. et al., "Use of the T4 Polynucleotide Ligase in the Joining of Flush-Ended DNA Segments Generated by Restriction Endonucleases", European Journal of Biochemistry (1978) 86:531-537.
Staeben, M. et al., "Development and Validation of a Transcreener Assay for Detection of AMP- and GMP-Producing Enzymes", Assay and Drug Development Technologies (2010) vol. 8, No. 3, p. 339-350.
Biochemistry Dictionary (3rd Edition) pp. 40 and 772 (2002) edited by Imabori and Yamakawa.
NCBI Reference Sequences: NP_999574.1, 2015.
NCBI Reference Sequence XP_003132357.3, 2015.
NCBI Reference Sequence: NP_001152884.1, 2016.
NCBI Reference Sequence: NP_001152885.1, 2016.
Luo et al., "An assay for Fe(II)/2-oxoglutarate-dependent dioxygenases by enzyme-coupled detection of succinate formation" Analytical Biochemistry, vol. 353, No. 1, Jun. 1, 2006, pp. 69-74.
Wibom et al., "A sensitive method for measuring ATP-formation in rat muscle mitochondria" Scandinavian Journal of Clinical and Laboratory Investigation, vol. 50, No. 2, Apr. 1990, pp. 143-152.
United States Patent Office Action for U.S. Appl. No. 12/460,573 dated Oct. 13, 2011 (7 pages).
United States Patent Office Action for U.S. Appl. No. 13/455,587 dated May 10, 2013 (12 pages).
United States Patent Office Action for U.S. Appl. No. 13/455,587 dated Aug. 31, 2012 (9 pages).
United States Patent Office Notice of Allowance for U.S. Appl. No. 12/460,573 dated Feb. 9, 2012 (5 pages).
International Search Report and Written Opinion for Application No. PCT/US2009/051170 dated Oct. 28, 2009 (9 pages).
International Search Report and Written Opinion for Application No. PCT/US2012/062397 dated Jun. 5, 2013.
United States Patent Office Action for U.S. Appl. No. 13/662,923 dated Mar. 24, 2014 (29 pages).
United States Patent Notice of Allowance for U.S. Appl. No. 13/455,587 dated Mar. 31, 2014 (5 pages).
United States Patent Office Final Rejection for U.S. Appl. No. 13/662,923 dated Jan. 12, 2015 (33 pages).
International Search Report and Written Opinion for Application No. PCT/US2015/031445 dated Jul. 30, 2015 (12 pages).

\* cited by examiner

BIOLUMINESCENT SUCCINATE DETECTION ASSAY

This application claims priority to provisional application No. 62/061,635, filed on Oct. 8, 2014.

FIELD OF THE INVENTION

The present invention relates to methods for detecting and quantifying succinate and methods for detecting and quantifying 2-oxoglutarate oxygenases, such as JumonjiC domain-containing histone lysine demethylases and 2-oxoglutarate-dependent dioxygenases.

BACKGROUND

Post translational modifications (PTMs) of proteins are important in determining the epigenetic status of the genome. These modifications include phosphorylation, methylation, acetylation, glycosylation, ubiquitination, nitrosylation, and lipidation and influence many aspects of normal cell biology and pathogenesis. More specifically, histone related PTMs are of great importance as covalent modifications of histones have been implicated in transcriptional regulation via chromatin modulation. Examples of post translational modifying enzymes include, but are not limited to, Kinases/Phosphatases, Methyltransferases/Demethylases, Acetyltransferases/Histone Deacetylases, Glycosyltransferases/Glucanases and ADP-Ribosyl Transferases. Under normal physiological conditions, the regulation of PTM enzymes is tightly regulated. However, under pathological conditions, the activity of these enzymes can be dysregulated, and the disruption of the intracellular networks governed by these enzymes leads to many diseases including cancer and inflammation. Consequently, PTM enzymes have become an important target for drug discovery creating a need for technological development to monitor their activities. These assays can be applied not only to High-Throughput Screening (HTS) to search for drug candidates against these diseases, but also to understand the role of these post-translational modifications in regulating cellular processes.

JumonjiC domain-containing histone lysine demethylases ("JMJC demethylases") play a role in determining the epigenetic status of the genome by counteracting the activities of histone lysine methyltransferases. These enzymes act as erasers by catalyzing the removal of methyl marks from specific lysine sites in histones, leading to either transcriptional repression or activation of target genes. JMJC demethylases are widely studied and, because of their implication in cancer, they have become validated drug targets. Thus, assays that monitor JMJC demethylase activities are desirable as basic research tools to elucidate their mode of regulation as well as to facilitate the identification of selective and potent inhibitors for drug discovery. Traditional JMJC demethylase assays use antibodies, enzyme-coupled assays, HPLC-based assays, or mass spectrometry to detect the substrates that have been demethylated by JMJC demethylases. These assays are not easily configured for rapid demethylase activity detection because they rely on the use of colorimetric, radioactive or fluorimetric non-homogenous antibody-based assays. Colorimetric assays are usually not desirable for drug discovery applications since they are prone to compound interference, low sensitivity, and higher rate of false hits. Radioactivity and mass spectrometry-based methods require sample processing. The use of radiolabeled materials requires waste management or cumbersome regulatory procedures. Because of the importance of these classes of enzymes, there is a need in developing enzymatic assays to monitor their activities, their regulation or identify novel inhibitors.

SUMMARY OF THE INVENTION

The present invention is directed to a method for luminescent detection or determination of succinate in a sample. The method comprises: (a) contacting the sample with a first detection reagent to form a first reaction mixture; (b) contacting the first reaction mixture with a second detection reagent to form a second reaction mixture; and (c) detecting luminescence in the second reaction mixture, thereby detecting or determining the presence or amount of succinate in the sample; wherein if succinate is present in the sample, the first detection reagent and the second detection reagent converts the succinate to ATP. Contacting the first reaction mixture with a second detection reagent may generate ATP. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for detecting or determining the presence or amount of succinate in a sample. The method comprises: (a) contacting the sample with a first detection reagent to form a first reaction mixture; (b) contacting the first reaction mixture with a second detection reagent to form a second reaction mixture; and (c) detecting luminescence in the second reaction mixture, thereby detecting or determining the presence or amount of succinate in the sample; wherein: (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate; (ii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iii) the first detection reagent comprises ADP forming succinyl-CoA ligase (SCS-ADP), ATP, and coenzyme A and the second detection reagent comprises an ATP depletion reagent and subsequently an ADP to ATP conversion/detection reagent, wherein the first reaction mixture is contacted sequentially with the ATP depletion reagent and the ADP to ATP conversion/detection reagent, and wherein the ATP depletion reagent comprises adenylate cyclase and pyrophosphatase and the ADP to ATP conversion/detection reagent comprises pyruvate kinase, phosphoenolpyruvate, a bioluminescent enzyme, and a luciferin substrate. The first detection reagent may comprise 3-oxoacid CoA-transferase (SCOT), inorganic phosphate, and acetoacetyl-CoA and the second detection reagent may comprise succinyl-CoA ligase (SCS), ADP, a thermostable firefly luciferase, and D-luciferin. The first detection reagent may comprise GDP forming succinyl-CoA ligase (SCS-GDP), GTP, and coenzyme A and the second detection reagent may comprise guanylate kinase (GMPK), ADP, a thermostable firefly luciferase, and D-luciferin. The first detection reagent may comprise ADP forming succinyl-CoA ligase (SCS-ADP), ATP, and coenzyme A and the second detection reagent may comprise an ATP depletion reagent and subsequently an ADP to ATP conversion/detection reagent, wherein the first reaction mixture is contacted sequentially with the ATP depletion reagent and the ADP to ATP conversion/detection reagent, and wherein the ATP depletion reagent comprises adenylate cyclase and pyrophosphatase and the ADP to ATP conversion/detection reagent comprises pyruvate kinase, phosphoenolpyruvate, a thermostable firefly luciferase, and D-luciferin. Contacting the first reaction mixture with a second detection reagent may generate ATP. The succinate forming enzyme may be a 2-oxoglutarate oxygenase. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for detecting or determining the presence or amount of a succinate forming enzyme in a sample or the activity of a succinate forming enzyme. The method comprises: (a) contacting the sample with a peptide, protein, or non-protein substrate, 2-oxoglutarate, Fe (II), and ascorbate to form a succinate reaction mixture, wherein succinate is formed if the sample comprises a succinate forming enzyme; (b) contacting the succinate reaction mixture with a first detection reagent to form a first reaction mixture, wherein the succinate formed in step (a) is converted to succinyl-CoA; (c) contacting the first reaction mixture with a second detection reagent to form a second reaction mixture; and (d) detecting luminescence in the second reaction mixture, thereby detecting or determining the presence or amount of succinate forming enzyme or succinate forming enzyme activity in the sample, wherein: (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate; (ii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iii) the first detection reagent comprises ADP forming succinyl-CoA ligase (SCS-ADP), ATP, and coenzyme A and the second detection reagent comprises an ATP depletion reagent and an ADP to ATP conversion/detection reagent, wherein the first reaction mixture is contacted sequentially with the ATP depletion reagent and the ADP to ATP conversion/detection reagent, wherein the ATP depletion reagent comprises adenylate cyclase and pyrophosphatase, and wherein the ADP to ATP conversion/detection reagent comprises pyruvate kinase, phosphoenolpyruvate, a bioluminescent enzyme, and a luciferin substrate. Contacting the first reaction mixture with a second detection reagent may generate ATP. The succinate forming enzyme may be a 2-oxoglutarate oxygenase. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The sample may be contacted with a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for determining whether a compound modulates 2-oxoglutarate oxygenase activity in a sample. The method comprises: (a) contacting the sample with the compound to form a test sample, wherein the sample comprises a 2-oxoglutarate oxygenase; (b) contacting the test sample with a peptide, protein, or non-protein substrate, 2-oxoglutarate, Fe (II), and ascorbate to form a succinate reaction mixture; (c) contacting the succinate reaction mixture with 3-oxoacid CoA-transferase (SCOT), inorganic phosphate, and acetoacetyl-CoA to form a first reaction mixture, whereby the succinate formed in step (a) is converted to succinyl-CoA; (d) contacting the first reaction mixture with an ATP detection reagent to form a second reaction mixture, wherein the ATP detection reagent comprises succinyl-CoA ligase (SCS), ADP, a bioluminescent enzyme, and a luciferin substrate; (e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The sample may be contacted with a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for determining whether a compound modulates 2-oxoglutarate oxygenase activity in a sample. The method comprises: (a) contacting the sample with the compound to form a test sample, wherein the sample comprises a 2-oxoglutarate oxygenase; (b) contacting the test sample with a peptide, protein, or non-protein substrate, 2-oxoglutarate, Fe (II), and ascorbate to form a succinate reaction mixture; (c) contacting the succinate reaction mixture with GDP forming succinyl-CoA ligase (SCS-GDP), GTP, and coenzyme A; to form a first reaction mixture, whereby the succinate formed in step (a) is converted to succinyl-CoA and GDP; (d) contacting the first reaction mixture with an ATP detection reagent to form a second reaction mixture, wherein the ATP detection reagent comprises guanylate kinase (GMPK), ADP, a bioluminescent enzyme, and a luciferin substrate; (e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The sample may be contacted with a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for determining whether a compound modulates 2-oxoglutarate oxygenase activity in a sample. The method comprises: (a) contacting the sample with the compound to form a test sample, wherein the sample comprises a 2-oxoglutarate oxygenase; (b) contacting the test sample with a peptide, protein, or non-protein substrate, 2-oxoglutarate, Fe (II), and ascorbate to form a succinate reaction mixture; (c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP; (d) contacting the first reaction mixture with an ATP depletion reagent to form a second reaction mixture, wherein the ATP depletion reagent comprises adenylate cyclase and pyrophosphatase (e) contacting the second reaction mixture with an ADP to ATP conversion/detection reagent to form a third reaction mixture, wherein the ADP to ATP conversion/detection reagent comprises pyruvate kinase, phosphoenolpyruvate, a bioluminescent enzyme, and a luciferin substrate; (f) detecting luminescence in the third reaction mixture; and (g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The sample may be contacted with a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting succinate in a sample. The kit comprises: (i) 3-oxoacid CoA-transfer (SCOT); (ii) inorganic phosphate; (iii) acetoacetyl-CoA; (iv) succinyl-CoA ligase (SCS); (v) ADP; (vi) a bioluminescent enzyme; and (vii) a luciferin substrate, wherein (i)-(vii) are in one or more containers. The kit may comprise a first detection reagent comprising: (i) 3-oxoacid CoA-transfer (SCOT); (ii) inorganic phosphate; and (iii) acetoacetyl-CoA; and a second detection reagent comprising: (iv) succinyl-CoA ligase (SCS); (v) ADP; (vi) a bioluminescent enzyme; and (vii) a luciferin substrate. The bioluminescent enzyme may be a thermostable firefly luciferase and the luciferin substrate may be D-luciferin. The kit may further comprise instructions for using the kit to detect or determine the presence or amount of succinate in the sample. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting succinate in a sample. The kit comprises: (i) GDP forming succinyl-CoA ligase (SCS-GDP); (ii) GTP; (iii) coenzyme A; (iv) guanylate kinase (GMPK); (v) ADP; (vi) a bioluminescent enzyme; and (vii) a luciferin substrate, wherein (i)-(vii) are in one or more containers. The kit may comprise a first detection reagent comprising: (i) GDP forming succinyl-CoA ligase (SCS-GDP); (ii) GTP; and (iii) coenzyme A; and a second detection reagent comprising: (iv) guanylate kinase (GMPK); (v) ADP; (vi) a bioluminescent enzyme; and (vii) a luciferin substrate. The kit may further comprise instructions for using the kit to detect or determine the presence or amount of succinate in the sample. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting succinate in a sample. The kit comprises: (i) ADP forming succinyl-CoA ligase (SCS-ADP); (ii) ATP; (iii) coenzyme A; (iv) adenylate cyclase; (v) pyrophosphatase; (vi) pyruvate kinase; (vii) phosphoenolpyruvate; (viii) a bioluminescent enzyme; and (ix) a luciferin substrate, wherein (i)-(ix) are in one or more containers. The first detection reagent may comprise: (i) ADP forming succinyl-CoA ligase (SCS-ADP); (ii) ATP; and (iii) coenzyme A; and the second detection reagent may comprise an ATP depletion reagent and an ADP to ATP conversion/detection reagent, wherein the ATP depletion reagent may comprise: (iv) adenylate cyclase; and (v) pyrophosphatase; and the ADP to ATP conversion/detection reagent may comprise: (vi) pyruvate kinase; (vii) phosphoenolpyruvate; (viii) a bioluminescent enzyme; and (ix) a luciferin substrate. The kit may further comprise instructions for using the kit to detect or determine the presence or amount of succinate in the sample. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting or determining 2-oxoglutarate oxygenase activity in a sample. The kit comprises: (i) a peptide, protein, or non-protein substrate; (ii) 2-oxoglutarate; (iii) Fe (II); (iv) ascorbate; (v) 3-oxoacid CoA-transfer (SCOT); (vi) inorganic phosphate; (vii) acetoacetyl-CoA; (viii) succinyl-CoA ligase (SCS); (ix)

ADP; (x) a bioluminescent enzyme; and (xi) a luciferin substrate, wherein (i)-(xi) are in one or more containers. The kit may comprise a first detection reagent comprising: (v) 3-oxoacid CoA-transfer (SCOT); (vi) inorganic phosphate; and (vii) acetoacetyl-CoA; and a second detection reagent comprising: (viii) succinyl-CoA ligase (SCS); (ix) ADP; (x) a bioluminescent enzyme; and (xi) a luciferin substrate. The kit may further comprise instructions for using the kit to detect or determine 2-oxoglutarate oxygenase activity in a sample. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The kit may comprise a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting or determining 2-oxoglutarate oxygenase activity in a sample. The kit comprises: (i) a peptide, protein, or non-protein substrate; (ii) 2-oxoglutarate; (iii) Fe (II); (iv) ascorbate; (v) GDP forming succinyl-CoA ligase (SCS-GDP); (vi) GTP; (vii) coenzyme A; (viii) guanylate kinase (GMPK); (ix) ADP; (x) a bioluminescent enzyme; and (xi) a luciferin substrate, wherein (i)-(xi) are in one or more containers. The kit may comprise a first detection reagent comprising: (v) GDP forming succinyl-CoA ligase (SCS-GDP); (vi) GTP; and (vii) coenzyme A; and a second detection reagent comprising: (viii) guanylate kinase (GMPK); (ix) ADP; (x) a bioluminescent enzyme; and (xi) a luciferin substrate. The kit may further comprise instructions for using the kit to detect or determine 2-oxoglutarate oxygenase activity in a sample. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The kit may comprise a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a kit for detecting or determining 2-oxoglutarate oxygenase activity in a sample. The kit comprises: (i) a peptide, protein, or non-protein substrate; (ii) 2-oxoglutarate; (iii) Fe (II); (iv) ascorbate; (v) ADP forming succinyl-CoA ligase (SCS-ADP); (vi) ATP; (vii) coenzyme A; (viii) adenylate cyclase; (ix) pyrophosphatase; (x) pyruvate kinase; (xi) phosphoenolpyruvate; (xii) a bioluminescent enzyme; and (xiii) a luciferin substrate, wherein (i)-(xiii) are in one or more containers. The kit may comprise a first detection reagent comprising: (v) ADP forming succinyl-CoA ligase (SCS-ADP); (vi) ATP; and (vii) coenzyme A; and a second detection reagent comprising an ATP depletion reagent and an ADP to ATP conversion/detection reagent, wherein the ATP depletion reagent may comprise: (viii) adenylate cyclase; and (ix) pyrophosphatase; and the ADP to ATP conversion/detection reagent may comprise: (x) pyruvate kinase; (xi) phosphoenolpyruvate; (xii) a bioluminescent enzyme; and (xiii) a luciferin substrate. The kit may further comprise instructions for using the kit to detect or determine 2-oxoglutarate oxygenase activity in a sample. The 2-oxoglutarate oxygenase may be a Fe (II) dependent lysine demethylase or a 2-oxoglutarate-dependent dioxygenase. The Fe (II) dependent lysine demethylases may be a JumonjiC domain-containing histone lysine (JMJC) demethylase. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, or JMJD6. The JMJC demethylase may be JMJD2A or JMJD2C. The kit may comprise a peptide, protein, or non-protein substrate. The peptide or protein substrate may be a histone peptide substrate. The histone peptide substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36. The bioluminescent enzyme may be a luciferase. The luciferase may be a recombinant luciferase. The luciferase may be a thermostable and/or a chemostable luciferase. The luciferase may be a thermostable firefly luciferase.

The present invention is directed to a method for luminescent detection or determination of succinate in a sample, the method comprising: (a) contacting the sample with a first detection reagent to form a first reaction mixture; (b) contacting the first reaction mixture with a second detection reagent to form a second reaction mixture; and (c) detecting luminescence in the second reaction mixture, thereby detecting or determining the presence or amount of succinate in the sample; wherein if succinate is present in the sample, the first detection reagent and the second detection reagent converts the succinate to ATP.

The present invention is directed to a method for detecting or determining the presence or amount of succinate in a sample, the method comprising: (a) contacting the sample with a first detection reagent to form a first reaction mixture; (b) contacting the first reaction mixture with a second detection reagent to form a second reaction mixture; and (c) detecting luminescence in the second reaction mixture, thereby detecting or determining the presence or amount of succinate in the sample; wherein: (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate; (ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate; (iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iv) the first detection reagent comprises ADP forming succinyl-CoA ligase (SCS-ADP), ATP, and coenzyme A and the second detection reagent comprises an ATP depletion reagent and subsequently an ADP-to-ATP conversion/detection reagent, wherein the first reaction mixture is contacted sequentially with the ATP depletion reagent and the ADP-to-ATP conversion/detection reagent, and wherein the ATP depletion reagent comprises adenylate cyclase and pyrophosphatase and the ADP-to-ATP conversion/detection reagent comprises pyruvate kinase, phosphoenolpyruvate, a bioluminescent enzyme, and a luciferin substrate.

The present invention is directed to a method for detecting or determining the presence or amount of a succinate forming enzyme in a sample or the activity of a succinate forming enzyme, the method comprising: (a) contacting the sample with a peptide, protein, or non-protein substrate, 2-oxoglutarate, Fe(II), and ascorbate to form a succinate reaction mixture, wherein succinate is formed if the sample comprises a succinate forming enzyme; (b) contacting the succinate reaction mixture with a first detection reagent to form a first reaction mixture, wherein the succinate formed in step (a) is converted to succinyl-CoA; (c) contacting the first reaction mixture with a second detection reagent to form a second reaction mixture; and (d) detecting luminescence in the second reaction mixture, thereby detecting or determining the presence or amount of succinate forming enzyme or succinate forming enzyme activity in the sample, wherein: (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate; (ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate; (iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iv) the first detection reagent comprises ADP forming succinyl-CoA ligase (SCS-ADP), ATP, and coenzyme A and the second detection reagent comprises an ATP depletion reagent and an ADP-to-ATP conversion/detection reagent, wherein the first reaction mixture is contacted sequentially with the ATP depletion reagent and the ADP-to-ATP conversion/detection reagent, wherein the ATP depletion reagent comprises adenylate cyclase and pyrophosphatase, and wherein the ADP-to-ATP conversion/detection reagent comprises pyruvate kinase, phosphoenolpyruvate, a bioluminescent enzyme, and a luciferin substrate.

The present invention is directed to a method for determining whether a compound modulates 2-oxoglutarate oxygenase activity in a sample, the method comprising: (a) contacting the sample with the compound to form a test sample, wherein the sample comprises a 2-oxoglutarate oxygenase; (b) contacting the test sample with a peptide, protein, or non-protein substrate, 2-oxoglutarate, Fe(II), and ascorbate to form a succinate reaction mixture; (c) contacting the succinate reaction mixture with: (i) 3-oxoacid CoA-transferase (SCOT), inorganic phosphate, and acetoacetyl-CoA to form a first reaction mixture, whereby the succinate formed in step (a) is converted to succinyl-CoA; or (ii) 3-oxoacid CoA-transferase (SCOT), inorganic phosphate, acetoacetyl-CoA, succinyl-CoA ligase (SCS), ADP, magnesium chloride to form a first reaction mixture, whereby the succinate formed in step (a) is converted to ATP; (d) contacting the first reaction mixture with an ATP detection reagent to form a second reaction mixture, wherein the ATP detection reagent comprises succinyl-CoA ligase (SCS), ADP, a bioluminescent enzyme, and a luciferin substrate; (e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

The present invention is directed to a method for determining whether a compound modulates 2-oxoglutarate oxygenase activity in a sample, the method comprising: (a) contacting the sample with the compound to form a test sample, wherein the sample comprises a 2-oxoglutarate oxygenase; (b) contacting the test sample with a peptide, protein, or non-protein substrate, 2-oxoglutarate, Fe(II), and ascorbate to form a succinate reaction mixture; (c) contacting the succinate reaction mixture with GDP forming succinyl-CoA ligase (SCS-GDP), GTP, and coenzyme A; to form a first reaction mixture, whereby the succinate formed in step (a) is converted to succinyl-CoA and GDP; (d) contacting the first reaction mixture with an ATP detection reagent to form a second reaction mixture, wherein the ATP detection reagent comprises guanylate kinase (GMPK), ADP, a bioluminescent enzyme, and a luciferin substrate; (e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

The present invention is directed to a method for determining whether a compound modulates 2-oxoglutarate oxygenase activity in a sample, the method comprising: (a) contacting the sample with the compound to form a test sample, wherein the sample comprises a 2-oxoglutarate oxygenase; (b) contacting the test sample with a peptide, protein, or non-protein substrate, 2-oxoglutarate, Fe(II), and ascorbate to form a succinate reaction mixture; (c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP; (d) contacting the first reaction mixture with an ATP depletion reagent to form a second reaction mixture, wherein the ATP depletion reagent comprises adenylate cyclase and pyrophosphatase; (e) contacting the second reaction mixture with an ADP-to-ATP conversion/detection reagent to form a third reaction mixture, wherein the ADP-to-ATP conversion/detection reagent comprises pyruvate kinase, phosphoenolpyruvate, a bioluminescent enzyme, and a luciferin substrate; (f) detecting luminescence in the third reaction mixture; and (g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity.

The present invention is directed to a kit for detecting succinate in a sample, the kit comprising: (i) 3-oxoacid CoA-transferase (SCOT); (ii) inorganic phosphate; (iii) acetoacetyl-CoA; (iv) succinyl-CoA ligase (SCS); (v) ADP; (vi) a bioluminescent enzyme; and (vii) a luciferin substrate, wherein (i)-(vii) are in one or more containers.

The present invention is directed to a kit for detecting succinate in a sample, the kit comprising: (i) GDP forming succinyl-CoA ligase (SCS-GDP); (ii) GTP; (iii) coenzyme A; (iv) guanylate kinase (GMPK); (v) ADP; (vi) a bioluminescent enzyme; and (vii) a luciferin substrate, wherein (i)-(vii) are in one or more containers.

The present invention is directed to a kit for detecting succinate in a sample, the kit comprising: (i) ADP forming succinyl-CoA ligase (SCS-ADP); (ii) ATP; (iii) coenzyme A; (iv) adenylate cyclase; (v) pyrophosphatase; (vi) pyruvate kinase; (vii) phosphoenolpyruvate; (viii) a bioluminescent enzyme; and (ix) a luciferin substrate, wherein (i)-(ix) are in one or more containers.

The present invention is directed to a kit for detecting or determining 2-oxoglutarate oxygenase activity in a sample, the kit comprising: (i) a peptide, protein, or non-protein substrate; (ii) 2-oxoglutarate; (iii) Fe(II); (iv) ascorbate; (v) 3-oxoacid CoA-transferase (SCOT); (vi) inorganic phosphate; (vii) acetoacetyl-CoA; (viii) succinyl-CoA ligase (SCS); (ix) ADP; (x) a bioluminescent enzyme; and (xi) a luciferin substrate, wherein (i)-(xi) are in one or more containers.

The present invention is directed to a kit for detecting or determining 2-oxoglutarate oxygenase activity in a sample, the kit comprising: (i) a peptide, protein, or non-protein substrate; (ii) 2-oxoglutarate; (iii) Fe(II); (iv) ascorbate; (v) GDP forming succinyl-CoA ligase (SCS-GDP); (vi) GTP; (vii) coenzyme A; (viii) guanylate kinase (GMPK); (ix) ADP; (x) a bioluminescent enzyme; and (xi) a luciferin substrate, wherein (i)-(xi) are in one or more containers.

The present invention is directed to a kit for detecting or determining 2-oxoglutarate oxygenase activity in a sample, the kit comprising: (i) a peptide, protein, or non-protein substrate; (ii) 2-oxoglutarate; (iii) Fe(II); (iv) ascorbate; (v) ADP forming succinyl-CoA ligase (SCS-ADP); (vi) ATP; (vii) coenzyme A; (viii) adenylate cyclase; (ix) pyrophosphatase; (x) pyruvate kinase; (xi) phosphoenolpyruvate; (xii) a bioluminescent enzyme; and (xiii) a luciferin substrate, wherein (i)-(xiii) are in one or more containers.

The present invention is directed to a method for detecting or determining the presence or amount of succinate in a sample, the method comprising: (a) contacting the sample with a first detection reagent to form a first reaction mixture; (b) contacting the first reaction mixture with a second detection reagent to form a second reaction mixture; and (c) detecting luminescence in the second reaction mixture, thereby detecting or determining the presence or amount of succinate in the sample; wherein the first detection reagent comprises ADP forming succinyl-CoA ligase (SCS-ADP), ATP, and coenzyme A, and the second detection reagent comprises an ATP depletion reagent and subsequently an ADP-to-ATP conversion/detection reagent, wherein the first reaction mixture is contacted sequentially with the ATP depletion reagent and the ADP-to-ATP conversion/detection reagent; and a bioluminescent enzyme, and a luciferin substrate.

The present invention is directed to a method for determining whether a compound modulates 2-oxoglutarate oxygenase activity in a sample, the method comprising: (a) contacting the sample with the compound to form a test sample, wherein the sample comprises a 2-oxoglutarate oxygenase; (b) contacting the test sample with a peptide, protein, or non-protein substrate, 2-oxoglutarate, Fe(II), and ascorbate to form a succinate reaction mixture; (c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP; (d) contacting the first reaction mixture with an ATP depletion reagent to form a second reaction mixture; (e) contacting the second reaction mixture with an ADP-to-ATP conversion/detection reagent to form a third reaction mixture, wherein the ADP-to-ATP conversion/detection reagent comprises pyruvate kinase, phosphoenolpyruvate, a bioluminescent enzyme, and a luciferin substrate; (f) detecting luminescence in the third reaction mixture; and (g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity.

The present invention is directed to a kit for detecting succinate in a sample, the kit comprising: (i) ADP forming succinyl-CoA ligase (SCS-ADP); (ii) ATP; (iii) coenzyme A; (iv) an ATP depletion reagent; (v) an ADP-to-ATP conversion/detection reagent; (vi) a bioluminescent enzyme; and (vii) a luciferin substrate, wherein (i)-(vii) are in one or more containers.

The present invention is directed to a kit for detecting or determining 2-oxoglutarate oxygenase activity in a sample, the kit comprising: (i) a peptide, protein, or non-protein substrate; (ii) 2-oxoglutarate; (iii) Fe(II); (iv) ascorbate; (v) ADP forming succinyl-CoA ligase (SCS-ADP); (vi) ATP; (vii) coenzyme A; (viii) an ATP depletion reagent; (ix) an ATP-to-ATP conversion/detection reagent; (x) a bioluminescent enzyme; and (xi) a luciferin substrate, wherein (i)-(xi) are in one or more containers.

DETAILED DESCRIPTION

Figure 1:
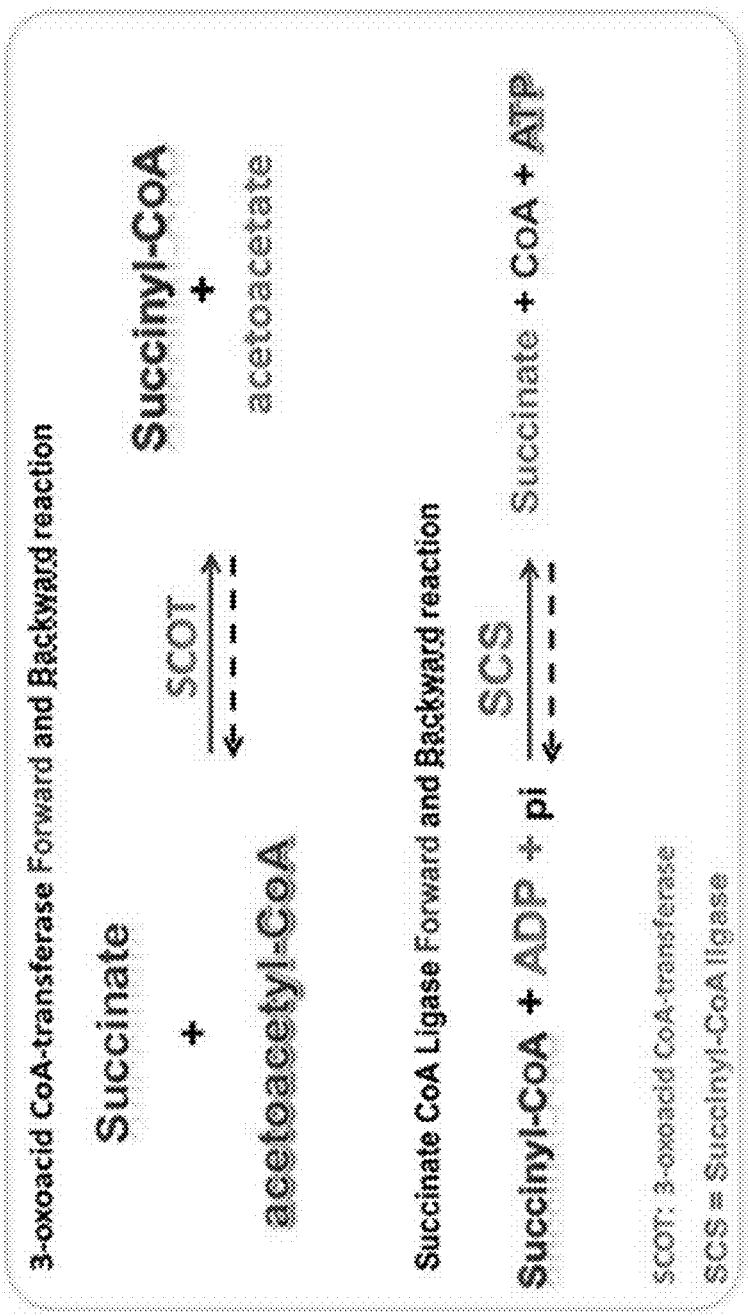
FIG. 1 illustrates a 3-oxoacid CoA-transferase/Succinyl-CoA Ligase Phosphotransferase reaction.

Disclosed herein is a versatile bioluminescent and homogeneous succinate detection assay, which may be adapted to measure 2-oxoglutarate oxygenase activity, such as JMJC demethylase activity. The bioluminescent succinate detection assay involves 3-oxoacid CoA transferase and/or succinyl-CoA ligase reactions (FIG. 1) to detect succinate in a bioluminescence format (see e.g., FIGS. 1, 8, 12, and 16). As the bioluminescent succinate detection assay detects succinate, it may be used with different substrates in diverse enzyme systems. For example, the bioluminescent succinate detection assay may be used with a succinate formation reaction, such as a demethylation reaction, to detect the presence and/or activity of a succinate forming or generating enzyme, such as 2-oxoglutarate oxygenase (e.g., JMJC demethylase and 2-oxoglutarate-dependent (2OG-dependent) dioxygenase). These enzymes are suitable for use in a bioluminescent succinate detection assay because they convert 2-oxoglutarate to succinate. The assay may also be used for monitoring enzymes involved in DNA demethylation, such as Ten-Eleven Translocation (TET) enzymes.

The bioluminescent succinate detection assay has the advantage of detecting 2-oxoglutarate oxygenases and their activities in a two-step assay with short incubation times and a robust and stable signal. This homogeneous assay is fast, sensitive, and simple, and it does not require washing steps. The two-step format assay involves the conversion of the succinate product to ATP, which is measured in a robust luciferase reaction, wherein the light output of the luciferase reaction is proportional to the succinate concentration from low nM to 20 µM. This highly sensitive assay allows the detection of low activity JMJC demethylases or the use of low amounts of purified JMJC demethylase, 2-oxoglutarate, and/or Fe(II). The assay is highly sensitive and robust, which allows for measuring the activity of a majority of JMJC demethylase subfamilies.

The disclosed assays and methods are convenient and may be used with any instrumentation platform without sample processing. The bioluminescent reaction has sufficient sensitivity and steady signal for use in high-throughput screening (HTS). The reagents may be designed with relative ease and may be synthesized readily. The reagents may facilitate measurement of enzymatic activity in many samples in a high throughput format over a long period of time due to the high signal stability generated by a luminogenic reaction, thus eliminating the need for a luminometer with reagent injectors and allowing for batch-mode processing of multiple samples. The present methods may be performed in a single well or in a multi-well plate, making them suitable for use as high throughput screening (HTS) methods for high sample processing or inhibitor screening. The bioluminescent succinate detection assay is a simple-to-use method that allows significant savings of enzyme usage and does not require radioactivity, antibodies, or modified substrates. The bioluminescent succinate detection assay is suitable for studying substrate specificity, evaluating kinetic parameters, and mode of action of JMJC demethylase inhibitors.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The terminology used herein is for the purpose of describing particular embodiments only and is not intended to be limiting. As used in the specification and the appended claims, the singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "2-oxoglutarate", "2OG", or "α-ketoglutarate", as used interchangeably herein, refers to the anion of α-ketoglutaric acid. 2-oxoglutarate is the keto acid produced by deamination of glutamate, and is an intermediate in the Krebs cycle.

The terms "3-oxoacid CoA-transferase" and "SCOT" as used interchangeably herein refer to an enzyme that catalyzes the chemical reaction:

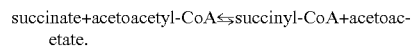

SCOT is also known as succinyl-CoA:3-oxo-acid CoA-transferase, 3-oxoacid coenzyme A-transferase, 3-ketoacid CoA-transferase, 3-ketoacid coenzyme A transferase, 3-oxoacid CoA dehydrogenase, acetoacetate succinyl-CoA transferase, acetoacetyl coenzyme A-succinic thiophorase, succinyl coenzyme A-acetoacetyl coenzyme A-transferase, and succinyl-CoA transferase. SCOT participates in 3 metabolic pathways: synthesis and degradation of ketone bodies, valine, leucine and isoleucine degradation, and butanoate metabolism. SCOT belongs to the family of CoA-transferases.

The term "luminescent" as used herein includes bioluminescence (i.e., light produced by a living organism). When the enzyme involved has evolved in an organism by natural selection for the purpose of generating light, or the enzyme involved is a mutated derivative of such an enzyme, the luminescent reactions are also called "bioluminescent reactions" and the enzyme involved is also called a "bioluminescent enzyme." Examples of bioluminescent enzymes include, without limitation, beetle luciferase, e.g., firefly luciferase, and the like.

The term "luciferin substrate" as used herein refers to a molecule capable of creating light via a chemical or biochemical reaction (e.g., luciferin, luciferin derivative, or a functional analog thereof). The luciferin substrate may be a molecule capable of creating light generated by a luciferase. Suitable luciferin substrates for luciferase enzymes include luciferin, luciferin derivatives, and functional analogs of luciferins. In some embodiments, functional analogs of luciferins include modified luciferins including derivatives of these compounds. Exemplary compounds include those disclosed in US Patent Publication No. 2009/0075309.

The term "luciferin derivative" as used herein refers to a type of luminogenic molecule or compound or luciferin substrate having a substantial structure of D-luciferin and is a luciferase substrate, e.g., aminoluciferin or fluoroluciferin, or luciferase substrates disclosed in U.S. Patent Publication No. 2007/0015790, Branchini et al. (1989), e.g., naphthyl and quinolyl derivatives, Branchini et al. (2002), and Branchini (2000), the disclosures of which are incorporated by reference herein.

"Modulate" as used herein may mean any altering of activity, such as regulate, down regulate, upregulate, reduce, inhibit, increase, decrease, deactivate, or activate.

"Series of calibrating compositions" refers to a plurality of compositions comprising a known concentration of succinate, wherein each of the compositions differs from the other compositions in the series by the concentration of succinate.

"Small molecules" as used herein may mean a molecule usually less than about 10 kDa molecular weight. Small molecules may be synthetic organic or inorganic compounds, peptides, (poly)nucleotides, (oligo)saccharides and the like. Small molecules specifically include small non-polymeric (i.e., not peptide or polypeptide) organic and inorganic molecules. Many pharmaceutical companies have extensive libraries of such molecules, which may be conveniently screened by using the herein described methods. Small molecules may have molecular weights of less than about 1000 Da, about 750 Da, or about 500 Da.

The terms "succinyl-CoA synthase," "succinyl-CoA ligase", and "SCS" as used interchangeably herein refer to an enzyme that catalyzes the reaction:

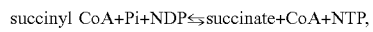

where Pi denotes inorganic phosphate, NDP denotes nucleoside diphosphate (e.g., GDP or ADP), and NTP denotes nucleoside triphosphate (e.g., GTP or ATP). The NDP may also denote CDP, TDP, or UDP. The NTP may also denote CTP, TTP, or UTP. Succinyl-CoA synthase facilitates the coupling of the conversion of succinyl CoA to succinate with the formation of a nucleoside triphosphate molecule, e.g., GTP or ATP, from an inorganic phosphate molecule and a nucleoside diphosphate molecule, e.g., GDP or ADP. SCS is also known as succinyl-CoA synthetase, succinate-CoA ligase, SUCL, succinic thiokinase, A-STK, G-STK, A-SCS, G-SCS, SCACT, VEG239, VEG63, Vegetative protein 239, Vegetative protein 63, CG11963 and succinate thiokinase.

SCS is one of the catalysts involved in the citric acid cycle, a central pathway in cellular metabolism, and it is located within the mitochondrial matrix of a cell. The terms "ADP-forming succinyl-CoA synthase," "SCS (ADP forming)," and "SCS-ADP" as used interchangeably herein refer to a SCS that catalyzes the reaction:

The terms "GDP-forming succinyl-CoA synthase," "SCS (GDP forming)," and "SCS-GDP" as used interchangeably herein refer to a SCS that catalyzes the reaction:

"Variant" is used herein to describe a peptide or polypeptide that differs in amino acid sequence by the insertion, deletion, or conservative substitution of amino acids, but retain at least one biological activity. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. "Variant" also can be used to describe a polypeptide or a fragment thereof that has been differentially processed, such as by proteolysis, phosphorylation, or other post-translational modification, yet retains its biological activity.

2. BIOLUMINESCENT SUCCINATE DETECTION ASSAY

The present disclosure provides a bioluminescent succinate detection assay for detecting succinate in a sample. The succinate detection assay involves the conversion of succinate in the sample to succinyl-CoA using 3-oxoacid CoA-transferase ("SCOT") and/or succinyl-CoA synthase ("SCS"), such as ADP-forming succinyl-CoA synthase ("SCS-ADP") and GDP-forming succinyl-CoA synthase ("SCS-GDP"). The conversion of succinate to succinyl-CoA is linked to the generation of ATP. The amount of ATP generated is detected using a luciferase/luciferin reaction and is proportional to the amount of succinate present in the sample.

a. SCOT/SCS (ADP Forming) Assay (ADP to ATP Conversion)

The enzyme SCOT catalyzes the conversion of succinate and acetoacetyl-CoA into acetoacetate and succinyl-CoA (see FIG. 1). The intermediate succinyl-CoA, in the presence of ADP and inorganic phosphate, is converted into succinate, CoA, and ATP by the enzyme SCS-ADP in a second reaction (see FIG. 1). The ATP that is generated is simultaneously converted into a bioluminescent signal, e.g., bioluminescence using an ATP detection reagent, e.g., a luciferin-luciferase reaction (See FIG. 2).

In the SCOT/SCS (ADP forming) assay method, the conversion of succinate to succinyl-CoA is performed using a reagent that contains SCOT, acetoacetyl-CoA, potassium phosphate (monobasic/dibasic), and a buffer such as MOPS, Tris or HEPES. The conversion of ADP to ATP is performed separately using a reagent, e.g., an ADP-to-ATP conversion reagent, such as Bioluminescent Succinate Detection Reagent II, which contains SCS (ADP forming), ADP, and magnesium sulfate or other divalent cation (such as magnesium chloride). The ATP may then be measured by the addition of an ATP detection reagent, e.g., a luciferin-luciferase assay reagent, e.g., the Kinase-Glo® assay reagent (Promega Corp.). The amount of luminescence generated is proportional to the amount of succinate present in the sample.

(1) First Detection Reagent—SCOT Reaction

The first detection reagent may include SCOT, inorganic phosphate, such as potassium phosphate (monobasic/dibasic), acetoacetyl-CoA (also known as 3-oxoacyl-CoA), and a buffer, such as MOPS, Tris or HEPES. The SCOT enzyme may be a SCOT enzyme from a eukaryote or a prokaryote. For example, the SCOT enzyme may be a SCOT enzyme from Sus scrofa. The SCOT enzyme may be encoded by a 3-oxoacid CoA-transferase gene sequence from a eukaryote or a prokaryote. For example, the SCOT enzyme may be encoded by a 3-oxoacid CoA-transferase gene sequence from Sus scrofa.

The first detection reagent may include from about 0.001 ng/µL to about 500.00 ng/µL, about 0.010 ng/µL to about 500.00 ng/µL, about 0.10 ng/µL to about 500.00 ng/µL, about 1.0 ng/µL to about 500.00 ng/µL, about 10.0 ng/µL to about 500.00 ng/µL, about 100.00 ng/µL to about 500.00 ng/µL, about 0.001 ng/µL to about 400.00 ng/µL, about 0.010 ng/µL to about 400.00 ng/µL, about 0.10 ng/µL to about 400.00 ng/µL, about 1.0 ng/µL to about 400.00 ng/µL, about 10.0 ng/µL to about 400.00 ng/µL, about 100.00 ng/µL to about 400.00 ng/µL, about 0.001 ng/µL to about 300.00 ng/µL, about 0.010 ng/µL to about 300.00 ng/µL, about 0.10 ng/µL to about 300.00 ng/µL, about 1.0 ng/µL to about 300.00 ng/µL, about 10.0 ng/µL to about 300.00 ng/µL, about 100.00 ng/µL to about 300.00 ng/µL, about 0.001 ng/µL to about 250.00 ng/µL, about 0.010 ng/µL to about 250.00 ng/µL, about 0.10 ng/µL to about 250.00 ng/µL, about 1.0 ng/µL to about 250.00 ng/µL, about 10.0 ng/µL to about 250.00 ng/µL, about 100.00 ng/µL to about 250.00 ng/µL, or at least about 0.001 ng/µL, at least about 0.003 ng/µL, at least about 0.006 ng/µL, at least about 0.012 ng/µL, at least about 0.020 ng/µL, at least about 0.050 ng/µL, at least about 0.090 ng/µL, at least about 0.100 ng/µL, at least about 0.150 ng/µL, at least about 0.190 ng/µL, at least about 0.200 ng/µL, at least about 0.250 ng/µL, at least about 0.300 ng/µL, at least about 0.350 ng/µL, at least about 0.370 ng/µL, at least about 0.400 ng/µL, at least about 0.500 ng/µL, at least about 0.740 ng/µL, at least about 1.00 ng/µL, at least about 1.50 ng/µL, at least about 2.00 ng/µL, at least about 2.50 ng/µL, at least about 2.97 ng/µL, at least about 3.00 ng/µL, at least about 4.00 ng/µL, at least about 5.00 ng/µL, at least about 5.94 ng/µL, at least about 7.50 ng/µL, at least about 10.00 ng/µL, at least about 11.88 ng/µL, at least about 15.00 ng/µL, at least about 20.00 ng/µL, at least about 23.75 ng/µL, at least about 30.00 ng/µL, at least about 40.00 ng/µL, at least about 47.50 ng/µL, at least about 50.00 ng/µL, at least about 60.00 ng/µL, at least about 70.00 ng/µL, at least about 80.00 ng/µL, at least about 90.00 ng/µL, at least about 95.0 ng/µL, at least about 100.00 ng/µL, at least about 150.00 ng/µL, at least about 190.0 ng/µL, at least about 200.00 ng/µL, at least about 250.00 ng/µL, at least about 300.00 ng/µL, at least about 350.00 ng/µL, at least about 380.0 ng/µL, at least about 400.00 ng/µL, or at least about 500.00 ng/µL of SCOT.

The first detection reagent may include from about 50 mM to about 1000 mM, from about 50 mM to about 750 mM, from about 50 mM to about 500 mM, from about 50 mM to about 250 mM, about 100 mM to about 1000 mM, from about 100 mM to about 750 mM, from about 100 mM to about 500 mM, from about 100 mM to about 250 mM, about 250 mM to about 1000 mM, from about 250 mM to about 750 mM, from about 250 mM to about 500 mM, about 500 mM to about 1000 mM, or from about 500 mM to about 750 mM, or at least about 50 mM, at least about 100 mM, at least about 150 mM, at least about 200 mM, at least about 250 mM, at least about 300 mM, at least about 350 mM, at least about 400 mM, at least about 450 mM, at least about 500 mM, at least about 550 mM, at least about 600 mM, at least about 650 mM, at least about 700 mM, at least about 750 mM, at least about 800 mM, at least about 850 mM, at least about 900 mM, at least about 950 mM, or at least about 1000 mM of potassium phosphate (monobasic/dibasic).

The first detection reagent may include from about 1 µM to about 1000 µM, about 1 µM to about 900 µM, about 1 µM to about 800 µM, about 1 µM to about 700 µM, about 1 µM to about 600 µM, about 1 µM to about 500 µM, about 1 µM to about 400 µM, about 1 µM to about 300 µM, about 1 µM to about 200 µM, about 1 µM to about 100 µM, about 10 µM to about 1000 µM, about 10 µM to about 900 µM, about 10 µM to about 800 µM, about 10 µM to about 700 µM, about 10 µM to about 600 µM, about 10 µM to about 500 µM, about 10 µM to about 400 µM, about 10 µM to about 300 µM, about 10 µM to about 200 µM, about 10 µM to about 100 µM, about 100 µM to about 1000 µM, about 100 µM to about 900 µM, about 100 µM to about 800 µM, about 100 µM to about 700 µM, about 100 µM to about 600 µM, about 100 µM to about 500 µM, about 100 µM to about 400 µM, about 100 µM to about 300 µM, about 100 µM to about 200 µM, about 250 µM to about 1000 µM, about 250 µM to about 900 µM, about 250 µM to about 800 µM, about 250 µM to about 700 µM, about 250 µM to about 600 µM, about 250 µM to about 500 µM, about 250 µM to about 400 µM, about 250 µM to about 300 µM, about 500 µM to about 1000 µM, about 500 µM to about 900 µM, about 500 µM to about 800 µM, about 500 µM to about 700 µM, about 500 µM to about 600 µM, about 750 µM to about 1000 µM, about 750 µM to about 900 µM, or about 750 µM to about 800 µM, or at least about 1 µM, at least about 2 µM, at least about 4 µM, at least about 5 µM, at least about 8 µM, at least about 10 µM, at least about 16 µM, at least about 20 µM, at least about 30 µM, at least about 32 µM, at least about 40 µM, at least about 50 µM, at least about 60 µM, at least about 64 µM, at least about 70 µM, at least about 80 µM, at least about 90 µM, at least about 100 µM, at least about 110 µM, at least about 120 µM, at least about 125 µM, at least about 130 µM, at least about 140 µM, at least about 150 µM, at least about 200 µM, at least about 250 µM, at least about 300 µM, at least about 350 µM, at least about 400 µM, at least about 450 µM, at least about 500 µM, at least about 550 µM, at least about 600 µM, at least about 650 µM, at least about 700 µM, at least about 750 µM, at least about 800 µM, at least about 850 µM, at least about 900 µM, at least about 950 µM, or at least about 1000 µM of acetoacetyl-CoA.

(2) Second Detection Reagent—SCS Reaction

The second detection reagent may include SCS (ADP forming), ADP, a bioluminescent enzyme, a luciferin substrate, and a buffer, such as MOPS, Tris or HEPES. The SCS (ADP forming) enzyme may be a SCS (ADP forming) enzyme from a eukaryote or a prokaryote. For example, the SCS (ADP forming) enzyme may be a SCS (ADP forming) enzyme from Sus scrofa or from E. coli. The SCS (ADP forming) enzyme may be encoded by a succinyl-CoA synthase alpha and beta subunit gene sequences from a eukaryote or a prokaryote. For example, the SCS (ADP forming) enzyme may be encoded by a succinyl-CoA synthase alpha and beta subunit gene sequences from Sus scrofa or from E. coli.

The second detection reagent may include from about 0.0001 U/μL, to about 0.1500 U/μL, about 0.0010 U/μL to about 0.1500 U/μL, about 0.0100 U/μL, to about 0.1500 U/μL, about 0.1000 U/μL, to about 0.1500 U/μL, 0.0001 U/μL, to about 0.1000 U/μL, about 0.0010 U/μL to about 0.1000 U/μL, about 0.0100 U/μL, to about 0.1000 U/μL, 0.0001 U/μL, to about 0.0100 U/μL, or about 0.0010 U/μL, to about 0.0100 U/μL, or at least about 0.0001 U/μL, at least about 0.0002 U/μL, at least about 0.0003 U/μL, at least about 0.0004 U/μL, at least about 0.0005 U/μL, at least about 0.0006 U/μL, at least about 0.0010 U/μL, at least about 0.0013 U/μL, at least about 0.0015 U/μL, at least about 0.0020 U/μL, at least about 0.0025 U/μL, at least about 0.0050 U/μL, at least about 0.0100 U/μL, at least about 0.0200 U/μL, at least about 0.0300 U/μL, at least about 0.0410 U/μL, at least about 0.0500 U/μL, at least about 0.0750 U/μL, at least about 0.0800 U/μL, at least about 0.0900 U/μL, at least about 0.1000 U/μL, at least about 0.1500 U/μL, at least about 0.1620 U/μL, or at least about 0.2000 U/μL, of SCS-ADP.

The second detection reagent may include at least about 0.5 μM, at least about 1.0 μM, at least about 1.5 μM, at least about 2.0 μM, at least about 2.1 μM, at least about 2.2 μM, at least about 2.3 μM, at least about 2.4 μM, at least about 2.5 μM, at least about 2.6 μM, at least about 2.7 μM, at least about 2.8 μM, at least about 2.9 μM, at least about 3.0 μM, at least about 3.5 μM, at least about 4.0 μM, or at least about 5.0 μM of ADP.

b. Modified SCOT/SCS (ADP Forming) Assay (ADP-to-ATP Conversion)

The enzyme SCOT catalyzes the conversion of succinate and acetoacetyl-CoA into acetoacetate and succinyl-CoA (see FIG. 1). The intermediate succinyl-CoA, in the presence of ADP and inorganic phosphate, is converted into succinate, CoA, and ATP by the enzyme SCS-ADP in a second reaction (see FIG. 1). The ATP that is generated is subsequently converted into a bioluminescent signal, e.g., bioluminescence using an ATP detection reagent, e.g., a luciferin-luciferase reaction (See FIG. 16).

In the modified SCOT/SCS (ADP forming) assay method, the conversion of succinate to ATP is performed using a reagent that contains SCOT, acetoacetyl-CoA, potassium phosphate (monobasic/dibasic), succinyl-CoA ligase (ADP forming)(SCS-ADP), ADP, magnesium sulfate or other divalent cation (such as magnesium chloride), and a buffer such as MOPS, Tris, or HEPES. The ATP may then be measured by the addition of an ATP detection reagent, e.g., a luciferin-luciferase assay reagent, e.g., the Kinase-Glo® assay reagent (Promega Corp.). Magnesium is required for SCS-ADP activity as an absence of magnesium causes a 10-fold decrease in activity for this assay. The amount of luminescence generated is proportional to the amount of succinate present in the sample.

(1) First Detection Reagent—SCOT/SCS-ADP Reaction

The first detection reagent may include SCOT, inorganic phosphate, such as potassium phosphate (monobasic/dibasic), acetoacetyl-CoA (also known as 3-oxoacyl-CoA), SCS (ADP forming; SCS-ADP), ADP, magnesium sulfate or other divalent cation (such as magnesium chloride), and a buffer, such as MOPS, Tris, or HEPES. The SCOT enzyme may be a SCOT enzyme from a eukaryote or a prokaryote. For example, the SCOT enzyme may be a SCOT enzyme from *Sus scrofa*. The SCOT enzyme may be encoded by a 3-oxoacid CoA-transferase gene sequence from a eukaryote or a prokaryote. For example, the SCOT enzyme may be encoded by a 3-oxoacid CoA-transferase gene sequence from *Sus scrofa*.

The first detection reagent may include from about 0.001 ng/μL to about 500.00 ng/μL, about 0.010 ng/μL to about 500.00 ng/μL, about 0.10 ng/μL to about 500.00 ng/μL, about 1.0 ng/μL to about 500.00 ng/μL, about 10.0 ng/μL to about 500.00 ng/μL, about 100.00 ng/μL to about 500.00 ng/μL, about 0.001 ng/μL to about 400.00 ng/μL, about 0.010 ng/μL to about 400.00 ng/μL, about 0.10 ng/μL to about 400.00 ng/μL, about 1.0 ng/μL to about 400.00 ng/μL, about 10.0 ng/μL to about 400.00 ng/μL, about 100.00 ng/μL to about 400.00 ng/μL, about 0.001 ng/μL to about 300.00 ng/μL, about 0.010 ng/μL to about 300.00 ng/μL, about 0.10 ng/μL to about 300.00 ng/μL, about 1.0 ng/μL to about 300.00 ng/μL, about 10.0 ng/μL to about 300.00 ng/μL, about 100.00 ng/μL to about 300.00 ng/μL, about 0.001 ng/μL to about 250.00 ng/μL, about 0.010 ng/μL to about 250.00 ng/μL, about 0.10 ng/μL to about 250.00 ng/μL, about 1.0 ng/μL to about 250.00 ng/μL, about 10.0 ng/μL to about 250.00 ng/μL, about 100.00 ng/μL to about 250.00 ng/μL, or at least about 0.001 ng/μL, at least about 0.003 ng/μL, at least about 0.006 ng/μL, at least about 0.012 ng/μL, at least about 0.020 ng/μL, at least about 0.050 ng/μL, at least about 0.090 ng/μL, at least about 0.100 ng/μL, at least about 0.150 ng/μL, at least about 0.190 ng/μL, at least about 0.200 ng/μL, at least about 0.250 ng/μL, at least about 0.300 ng/μL, at least about 0.350 ng/μL, at least about 0.370 ng/μL, at least about 0.400 ng/μL, at least about 0.500 ng/μL, at least about 0.740 ng/μL, at least about 1.00 ng/μL, at least about 1.50 ng/μL, at least about 2.00 ng/μL, at least about 2.50 ng/μL, at least about 2.97 ng/μL, at least about 3.00 ng/μL, at least about 4.00 ng/μL, at least about 5.00 ng/μL, at least about 5.94 ng/μL, at least about 7.50 ng/μL, at least about 10.00 ng/μL, at least about 11.88 ng/μL, at least about 15.00 ng/μL, at least about 20.00 ng/μL, at least about 23.75 ng/μL, at least about 30.00 ng/μL, at least about 40.00 ng/μL, at least about 47.50 ng/μL, at least about 50.00 ng/μL, at least about 60.00 ng/μL, at least about 70.00 ng/μL, at least about 80.00 ng/μL, at least about 90.00 ng/μL, at least about 95.0 ng/μL, at least about 100.00 ng/μL, at least about 150.00 ng/μL, at least about 190.0 ng/μL, at least about 200.00 ng/μL, at least about 250.00 ng/μL, at least about 300.00 ng/μL, at least about 350.00 ng/μL, at least about 380.0 ng/μL, at least about 400.00 ng/μL, or at least about 500.00 ng/μL of SCOT.

The first detection reagent may include from about 50 mM to about 1000 mM, from about 50 mM to about 750 mM, from about 50 mM to about 500 mM, from about 50 mM to about 250 mM, about 100 mM to about 1000 mM, from about 100 mM to about 750 mM, from about 100 mM to about 500 mM, from about 100 mM to about 250 mM, about 250 mM to about 1000 mM, from about 250 mM to about 750 mM, from about 250 mM to about 500 mM, about 500 mM to about 1000 mM, or from about 500 mM to about 750 mM, or at least about 50 mM, at least about 100 mM, at least about 150 mM, at least about 200 mM, at least about 250 mM, at least about 300 mM, at least about 350 mM, at least about 400 mM, at least about 450 mM, at least about 500 mM, at least about 550 mM, at least about 600 mM, at least about 650 mM, at least about 700 mM, at least about 750 mM, at least about 800 mM, at least about 850 mM, at least about 900 mM, at least about 950 mM, or at least about 1000 mM of potassium phosphate (monobasic/dibasic).

The first detection reagent may include from about 1 μM to about 1000 μM, about 1 μM to about 900 μM, about 1 μM to about 800 μM, about 1 μM to about 700 μM, about 1 μM to about 600 μM, about 1 μM to about 500 μM, about 1 μM to about 400 μM, about 1 μM to about 300 μM, about 1 μM to about 200 μM, about 1 μM to about 100 μM, about 10 μM to about 1000 µM, about 10 µM to about 900 µM, about 10 µM to about 800 µM, about 10 µM to about 700 µM, about 10 µM to about 600 µM, about 10 µM to about 500 µM, about 10 µM to about 400 µM, about 10 µM to about 300 µM, about 10 µM to about 200 µM, about 10 µM to about 100 µM, about 100 µM to about 1000 µM, about 100 µM to about 900 µM, about 100 µM to about 800 µM, about 100 µM to about 700 µM, about 100 µM to about 600 µM, about 100 µM to about 500 µM, about 100 µM to about 400 µM, about 100 µM to about 300 µM, about 100 µM to about 200 µM, about 250 µM to about 1000 µM, about 250 µM to about 900 µM, about 250 µM to about 800 µM, about 250 µM to about 700 µM, about 250 µM to about 600 µM, about 250 µM to about 500 µM, about 250 µM to about 400 µM, about 250 µM to about 300 µM, about 500 µM to about 1000 µM, about 500 µM to about 900 µM, about 500 µM to about 800 µM, about 500 µM to about 700 µM, about 500 µM to about 600 µM, about 750 µM to about 1000 µM, about 750 µM to about 900 µM, or about 750 µM to about 800 µM, or at least about 1 µM, at least about 2 µM, at least about 4 µM, at least about 5 µM, at least about 8 µM, at least about 10 µM, at least about 16 µM, at least about 20 µM, at least about 30 µM, at least about 32 µM, at least about 40 µM, at least about 50 µM, at least about 60 µM, at least about 64 µM, at least about 70 µM, at least about 80 µM, at least about 90 µM, at least about 100 µM, at least about 110 µM, at least about 120 µM, at least about 125 µM, at least about 130 µM, at least about 140 µM, at least about 150 µM, at least about 200 µM, at least about 250 µM, at least about 300 µM, at least about 350 µM, at least about 400 µM, at least about 450 µM, at least about 500 µM, at least about 550 µM, at least about 600 µM, at least about 650 µM, at least about 700 µM, at least about 750 µM, at least about 800 µM, at least about 850 µM, at least about 900 µM, at least about 950 µM, or at least about 1000 µM of acetoacetyl-CoA.

The first detection reagent may include from about 0.0001 U/µL to about 0.1500 U/µL, about 0.0010 U/µL to about 0.1500 U/µL, about 0.0100 U/µL to about 0.1500 U/µL, about 0.1000 U/µL to about 0.1500 U/µL, 0.0001 U/µL to about 0.1000 U/µL, about 0.0010 U/µL to about 0.1000 U/µL, about 0.0100 U/µL to about 0.1000 U/µL, 0.0001 U/µL to about 0.0100 U/µL, or about 0.0010 U/µL to about 0.0100 U/µL, or at least about 0.0001 U/µL, at least about 0.0002 U/µL, at least about 0.0003 U/µL, at least about 0.0004 U/µL, at least about 0.0005 U/µL, at least about 0.0006 U/µL, at least about 0.0010 U/µL, at least about 0.0013 U/µL, at least about 0.0015 U/µL, at least about 0.0020 U/µL, at least about 0.0025 U/µL, at least about 0.0050 U/µL, at least about 0.0100 U/µL, at least about 0.0200 U/µL, at least about 0.0300 U/µL, at least about 0.0410 U/µL, at least about 0.0500 U/µL, at least about 0.0750 U/µL, at least about 0.0800 U/µL, at least about 0.0900 U/µL, at least about 0.1000 U/µL, at least about 0.1500 U/µL, at least about 0.1620 U/µL, or at least about 0.2000 U/µL of SCS-ADP.

The first detection reagent may include at least about 0.5 µM, at least about 1.0 µM, at least about 1.5 µM, at least about 2.0 µM, at least about 2.1 µM, at least about 2.2 µM, at least about 2.3 µM, at least about 2.4 µM, at least about 2.5 µM, at least about 2.6 µL, at least about 2.7 µM, at least about 2.8 µM, at least about 2.9 µM, at least about 3.0 µL, at least about 3.5 µM, at least about 4.0 µM, or at least about 5.0 µM of ADP.

The first detection reagent may include from about 0.05 mM to about 50 mM, about 0.05 mM to about 25 mM, about 0.05 mM to about 12.5 mM, about 0.05 mM to about 6.25 mM, about 0.05 mM to about 3.13 mM, about 0.05 mM to about 1.56 mM, about 0.05 mM to about 0.78 mM, about 0.05 mM to about 0.39 mM, about 0.05 mM to about 0.19 mM, about 0.05 mM to about 0.10 mM, about 0.10 mM to about 50 mM, about 0.10 mM to about 25 mM, about 0.10 mM to about 12.5 mM, about 0.10 mM to about 6.25 mM, about 0.10 mM to about 3.13 mM, about 0.10 mM to about 1.56 mM, about 0.10 mM to about 0.78 mM, about 0.10 mM to about 0.39 mM, about 0.10 mM to about 0.20 mM, about 0.20 mM to about 50 mM, about 0.20 mM to about 25 mM, about 0.20 mM to about 12.5 mM, about 0.20 mM to about 6.25 mM, about 0.20 mM to about 3.13 mM, about 0.20 mM to about 1.56 mM, about 0.20 mM to about 0.78 mM, about 0.20 mM to about 0.40 mM, about 0.40 mM to about 50 mM, about 0.40 mM to about 25 mM, about 0.40 mM to about 12.5 mM, about 0.40 mM to about 6.25 mM, about 0.40 mM to about 3.13 mM, about 0.40 mM to about 1.56 mM, about 0.40 mM to about 0.80 mM, about 0.80 mM to about 50 mM, about 0.80 mM to about 25 mM, about 0.80 mM to about 12.5 mM, about 0.80 mM to about 6.25 mM, about 0.80 mM to about 3.13 mM, about 0.80 mM to about 1.56 mM, about 1.56 mM to about 50 mM, about 1.56 mM to about 25 mM, about 1.56 mM to about 12.5 mM, about 1.56 mM to about 6.25 mM, about 1.56 mM to about 3.13 mM, about 3.13 mM to about 50 mM, about 3.13 mM to about 25 mM, about 3.13 mM to about 12.5 mM, about 3.13 mM to about 6.25 mM, about 6.25 mM to about 50 mM, about 6.25 mM to about 25 mM, about 6.25 mM to about 12.5 mM, about 12.5 mM to about 50 mM, about 12.5 mM to about 25 mM, or about 25 mM to about 50 mM, or at least about 0.05 mM, at least about 0.1 mM, at least about 0.2 mM, at least about 0.4 mM, at least about 0.8 mM, at least about 1.56 mM, at least about 3.13 mM, at least about 6.25 mM, at least about 10 mM, at least about 12 mM, at least about 15 mM, at least about 20 mM, at least about 21 mM, at least about 22 mM, at least about 25 mM, at least about 30 mM, at least about 31 mM, at least about 32 mM, at least about 35 mM, at least about 40 mM, at least about 41 mM, at least about 42 mM, at least about 45 mM, or at least about 50 mM of magnesium sulfate or other divalent cation (such as magnesium chloride).

(2) Second Detection Reagent—Luciferase Reaction

The second detection reagent may include a bioluminescent enzyme, a luciferin substrate, and a buffer, such as MOPS, Tris, or HEPES.

c. SCS-GDP/GMPK Assay

The enzyme GDP-forming succinyl-CoA synthase catalyzes the conversion of succinate, CoA, and GTP to succinyl-CoA, GDP, and Pi. In the SCS-GDP/GMPK assay method, the conversion of succinate to succinyl-CoA is performed using a reagent that contains GDP-forming succinyl-CoA synthase ("SCS-GDP"), GTP, magnesium sulfate or other divalent cation (such as magnesium chloride), and coenzyme A. The conversion of GDP to ATP may be performed separately using a reagent containing guanylate kinase and ADP. The ATP may then be measured by the addition of an ATP detection reagent, e.g., a luciferin-luciferase assay reagent, e.g., the Kinase-Glo® assay reagent (Promega Corp.). Magnesium is required for both SDS-GDP and GMPK activity in this assay. The amount of luminescence generated is proportional to the amount of succinate present in the sample (see FIG. 8).

(1) First Detection Reagent—SCS-GDP

The first detection reagent includes SCS-GDP, GTP, coenzyme A, and a buffer, such as MOPS, Tris or HEPES. The SCS-GDP enzyme may be a SCS-GDP enzyme from a eukaryote or a prokaryote. For example, the SCS-GDP enzyme may be a SCS-GDP enzyme from *Sus scrofa*. The SCS-GDP enzyme may be encoded by a succinate-CoA ligase, alpha and beta subunit gene sequences from a eukaryote or a prokaryote. For example, the SCS-GDP enzyme may be encoded by a succinate-CoA ligase, alpha and beta subunit gene sequences from *Sus scrofa*.

The first detection reagent may include from about 0.50 µg/mL to about 100 µg/mL, about 0.50 µg/mL to about 50 µg/mL, about 0.50 µg/mL to about 25 µg/mL, about 0.50 µg/mL to about 10 µg/mL, about 5.0 µg/mL to about 100 µg/mL, about 5.0 µg/mL to about 50 µg/mL, about 5.0 µg/mL to about 25 µg/mL, about 5.0 µg/mL to about 10 µg/mL, about 10.0 µg/mL to about 100 µg/mL, about 10.0 µg/mL to about 50 µg/mL, or about 10.0 µg/mL to about 25 µg/mL, or at least about 0.50 µg/mL, at least about 0.78 µg/mL, at least about 1 µg/mL, at least about 1.5 µg/mL, at least about 2 µg/mL, at least about 2.5 µg/mL, at least about 3 µg/mL, at least about 5 µg/mL, at least about 6 µg/mL, at least about 10 µg/mL, at least about 12 µg/mL, at least about 15 µg/mL, at least about 20 µg/mL, at least about 25 µg/mL, at least about 50 µg/mL, or at least about 100 µg/mL of SCS-GDP.

The first detection reagent may include from about 1 µM to about 30 µM, about 1 µM to about 20 µM, about 1 µM to about 10 µM, about 5 µM to about 30 µM, about 5 µM to about 20 µM, or about 5 µM to about 10 µM, or at least about 1 µM, at least about 5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 25 µM, or at least about 30 µM of GTP.

The first detection reagent may include from about 1 µM to about 25 µM, about 1 µM to about 20 µM, about 1 µM to about 10 µM, about 5 µM to about 25 µM, about 5 µM to about 20 µM, or about 5 µM to about 10 µM, or at least about 1 µM, at least about 5 µM, at least about 10 µM, at least about 11 µM, at least about 12 µM, at least about 13 µM, at least about 14 µM, at least about 15 µM, at least about 16 µM, at least about 17 µM, at least about 110 µM, at least about 18 µM, at least about 19 µM, at least about 20 µM, or at least about 25 µM of coenzyme A.

The first detection reagent may include from about 0.05 mM to about 50 mM, about 0.05 mM to about 25 mM, about 0.05 mM to about 12.5 mM, about 0.05 mM to about 6.25 mM, about 0.05 mM to about 3.13 mM, about 0.05 mM to about 1.56 mM, about 0.05 mM to about 0.78 mM, about 0.05 mM to about 0.39 mM, about 0.05 mM to about 0.19 mM, about 0.05 mM to about 0.10 mM, about 0.10 mM to about 50 mM, about 0.10 mM to about 25 mM, about 0.10 mM to about 12.5 mM, about 0.10 mM to about 6.25 mM, about 0.10 mM to about 3.13 mM, about 0.10 mM to about 1.56 mM, about 0.10 mM to about 0.78 mM, about 0.10 mM to about 0.39 mM, about 0.10 mM to about 0.20 mM, about 0.20 mM to about 50 mM, about 0.20 mM to about 25 mM, about 0.20 mM to about 12.5 mM, about 0.20 mM to about 6.25 mM, about 0.20 mM to about 3.13 mM, about 0.20 mM to about 1.56 mM, about 0.20 mM to about 0.78 mM, about 0.20 mM to about 0.40 mM, about 0.40 mM to about 50 mM, about 0.40 mM to about 25 mM, about 0.40 mM to about 12.5 mM, about 0.40 mM to about 6.25 mM, about 0.40 mM to about 3.13 mM, about 0.40 mM to about 1.56 mM, about 0.40 mM to about 0.80 mM, about 0.80 mM to about 50 mM, about 0.80 mM to about 25 mM, about 0.80 mM to about 12.5 mM, about 0.80 mM to about 6.25 mM, about 0.80 mM to about 3.13 mM, about 0.80 mM to about 1.56 mM, about 1.56 mM to about 50 mM, about 1.56 mM to about 25 mM, about 1.56 mM to about 12.5 mM, about 1.56 mM to about 6.25 mM, about 1.56 mM to about 3.13 mM, about 3.13 mM to about 50 mM, about 3.13 mM to about 25 mM, about 3.13 mM to about 12.5 mM, about 3.13 mM to about 6.25 mM, about 6.25 mM to about 50 mM, about 6.25 mM to about 25 mM, about 6.25 mM to about 12.5 mM, about 12.5 mM to about 50 mM, about 12.5 mM to about 25 mM, or about 25 mM to about 50 mM, or at least about 0.05 mM, at least about 0.1 mM, at least about 0.2 mM, at least about 0.4 mM, at least about 0.8 mM, at least about 1.56 mM, at least about 3.13 mM, at least about 6.25 mM, at least about 10 mM, at least about 12 mM, at least about 15 mM, at least about 20 mM, at least about 21 mM, at least about 22 mM, at least about 25 mM, at least about 30 mM, at least about 31 mM, at least about 32 mM, at least about 35 mM, at least about 40 mM, at least about 41 mM, at least about 42 mM, at least about 45 mM, or at least about 50 mM of magnesium sulfate or other divalent cation (such as magnesium chloride).

(2) Second Detection Reagent—GMPK

The second detection reagent may include guanylate kinase (GMPK), ADP, a bioluminescent enzyme, a luciferin substrate, and a buffer, such as MOPS, Tris or HEPES. The GMPK enzyme may be a GMPK enzyme from a eukaryote or a prokaryote. For example, the GMPK enzyme may be a GMPK enzyme from *Bos taurus*. The GMPK enzyme may be encoded by a guanylate kinase 1 gene sequence from a eukaryote or a prokaryote. For example, the GMPK enzyme may be encoded by a guanylate kinase 1 gene sequence from *Bos taurus*.

The second detection reagent may include from about 0.01 µg/mL to about 300 µg/mL, about 0.01 µg/mL to about 200 µg/mL, about 0.01 µg/mL to about 100 µg/mL, about 0.01 µg/mL to about 50 µg/mL, about 0.10 µg/mL to about 300 µg/mL, about 0.10 µg/mL to about 200 µg/mL, about 0.10 µg/mL to about 100 µg/mL, about 0.10 µg/mL to about 50 µg/mL, about 1.0 µg/mL to about 300 µg/mL, about 1.0 µg/mL to about 200 µg/mL, about 1.0 µg/mL to about 100 µg/mL, about 1.0 µg/mL to about 50 µg/mL, about 10 µg/mL to about 300 µg/mL, about 10 µg/mL to about 200 µg/mL, about 10 µg/mL to about 100 µg/mL, about 10 µg/mL to about 50 µg/mL, about 50 µg/mL to about 300 µg/mL, about 50 µg/mL to about 200 µg/mL, about 50 µg/mL to about 100 µg/mL, or at least about 0.01 µg/mL, at least about 0.02 µg/mL, at least about 0.04 µg/mL, at least about 0.08 µg/mL, at least about 0.10 µg/mL, at least about 0.16 µg/mL, at least about 0.20 µg/mL, at least about 0.31 µg/mL, at least about 0.50 µg/mL, at least about 0.63 µg/mL, at least about 1.00 µg/mL, at least about 1.25 µg/mL, at least about 1.50 µg/mL, at least about 2.0 µg/mL, at least about 2.5 µg/mL, at least about 5 µg/mL, at least about 10 µg/mL, at least about 20 µg/mL, at least about 40 µg/mL, at least about 60 µg/mL, at least about 70 µg/mL, at least about 100 µg/mL, at least about 150 µg/mL, at least about 200 µg/mL, at least about 280 µg/mL, or at least about 300 µg/mL of GMPK.

The second detection reagent may include from about 0.5 µM to about 5.0 µM, about 0.5 µM to about 4.0 µM, about 0.5 µM to about 3.0 µM, about 0.5 µM to about 2.0 µM, about 1.0 µM to about 5.0 µM, about 1.0 µM to about 4.0 µM, about 1.0 µM to about 3.0 µM, about 1.0 µM to about 2.0 µM, about 2.0 µM to about 5.0 µM, about 2.0 µM to about 4.0 µM, about 2.0 µM to about 3.0 µM, about 3.0 µM to about 5.0 µM, about 3.0 µM to about 4.0 µM, or about 4.0 µM to about 5.0 µM, or at least about 0.5 µM, at least about 1.0 µM, at least about 1.5 µM, at least about 2.0 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3.0 µM, at least about 3.5 µM, at least about 4.0 µM, or at least about 5.0 µM of ADP.

d. Modified SCS-GDP/GMPK Assay

The enzyme GDP-forming succinyl-CoA synthase catalyzes the conversion of succinate, CoA, and GTP to succinyl-CoA, GDP, and Pi. In the SCS-GDP/GMPK assay method, the conversion of succinate to succinyl-CoA is performed using a reagent that contains GDP-forming succinyl-CoA synthase ("SCS-GDP"), GTP, magnesium sulfate or other divalent cation (such as magnesium chloride), and coenzyme A. The conversion of GDP to ATP may be performed simultaneously using a reagent containing guanylate kinase and ADP. The ATP that is generated may then be measured by the addition of an ATP detection reagent, e.g., a luciferin-luciferase assay reagent, e.g., the Kinase-Glo® assay reagent (Promega Corp.). The amount of luminescence generated is proportional to the amount of succinate present in the sample (1) First Detection Reagent—SCS-GDP/GMPK Reaction The first detection reagent includes SCS-GDP, GTP, coenzyme A, guanylate kinase (GMPK), ADP, and a buffer, such as MOPS, Tris or HEPES. The SCS-GDP enzyme may be a SCS-GDP enzyme from a eukaryote or a prokaryote. For example, the SCS-GDP enzyme may be a SCS-GDP enzyme from Sus scrofa. The SCS-GDP enzyme may be encoded by a succinate-CoA ligase, alpha and beta subunit gene sequences from a eukaryote or a prokaryote. For example, the SCS-GDP enzyme may be encoded by a succinate-CoA ligase, alpha and beta subunit gene sequences from Sus scrofa. The GMPK enzyme may be a GMPK enzyme from a eukaryote or a prokaryote. For example, the GMPK enzyme may be a GMPK enzyme from Bos taurus. The GMPK enzyme may be encoded by a guanylate kinase 1 gene sequence from a eukaryote or a prokaryote. For example, the GMPK enzyme may be encoded by a guanylate kinase 1 gene sequence from Bos taurus.

The first detection reagent may include from about 0.50 µg/mL to about 100 µg/mL, about 0.50 µg/mL to about 50 µg/mL, about 0.50 µg/mL to about 25 µg/mL, about 0.50 µg/mL to about 10 µg/mL, about 5.0 µg/mL to about 100 µg/mL, about 5.0 µg/mL to about 50 µg/mL, about 5.0 µg/mL to about 25 µg/mL, about 5.0 µg/mL to about 10 µg/mL, about 10.0 µg/mL to about 100 µg/mL, about 10.0 µg/mL to about 50 µg/mL, or about 10.0 µg/mL to about 25 µg/mL, or at least about 0.50 µg/mL, at least about 0.78 µg/mL, at least about 1 µg/mL, at least about 1.5 µg/mL, at least about 2 µg/mL, at least about 2.5 µg/mL, at least about 3 µg/mL, at least about 5 µg/mL, at least about 6 µg/mL, at least about 10 µg/mL, at least about 12 µg/mL, at least about 15 µg/mL, at least about 20 µg/mL, at least about 25 µg/mL, at least about 50 µg/mL, or at least about 100 µg/mL of SCS-GDP.

The first detection reagent may include from about 1 µM to about 30 µM, about 1 µM to about 20 µM, about 1 µM to about 10 µM, about 5 µM to about 30 µM, about 5 µM to about 20 µM, or about 5 µM to about 10 µM, or at least about 1 µM, at least about 5 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 25 µM, or at least about 30 µM of GTP.

The first detection reagent may include from about 1 µM to about 25 µM, about 1 µM to about 20 µM, about 1 µM to about 10 µM, about 5 µM to about 25 µM, about 5 µM to about 20 µM, or about 5 µM to about 10 µM, or at least about 1 µM, at least about 5 µM, at least about 10 µM, at least about 11 µM, at least about 12 µM, at least about 13 µM, at least about 14 µM, at least about 15 µM, at least about 16 µM, at least about 17 µM, at least about 110 µM, at least about 18 µM, at least about 19 µM, at least about 20 µM, or at least about 25 µM of coenzyme A.

The first detection reagent may include from about 0.01 µg/mL to about 300 µg/mL, about 0.01 µg/mL to about 200 µg/mL, about 0.01 µg/mL to about 100 µg/mL, about 0.01 µg/mL to about 50 µg/mL, about 0.10 µg/mL to about 300 µg/mL, about 0.10 µg/mL to about 200 µg/mL, about 0.10 µg/mL to about 100 µg/mL, about 0.10 µg/mL to about 50 µg/mL, about 1.0 µg/mL to about 300 µg/mL, about 1.0 µg/mL to about 200 µg/mL, about 1.0 µg/mL to about 100 µg/mL, about 1.0 µg/mL to about 50 µg/mL, about 10 µg/mL to about 300 µg/mL, about 10 µg/mL to about 200 µg/mL, about 10 µg/mL to about 100 µg/mL, about 10 µg/mL to about 50 µg/mL, about 50 µg/mL to about 300 µg/mL, about 50 µg/mL to about 200 µg/mL, about 50 µg/mL to about 100 µg/mL, or at least about 0.01 µg/mL, at least about 0.02 µg/mL, at least about 0.04 µg/mL, at least about 0.08 µg/mL, at least about 0.10 µg/mL, least about 0.16 µg/mL, at least about 0.20 µg/mL, at least about 0.31 µg/mL, at least about 0.50 µg/mL, at least about 0.63 µg/mL, at least about 1.00 µg/mL, at least about 1.25 µg/mL, at least about 1.50 µg/mL, at least about 2.0 µg/mL, at least about 2.5 µg/mL, at least about 5 µg/mL, at least about 10 µg/mL, at least about 20 µg/mL, at least about 40 µg/mL, at least about 60 µg/mL, at least about 70 µg/mL, at least about 100 µg/mL, at least about 150 µg/mL, at least about 200 µg/mL, at least about 280 µg/mL, or at least about 300 µg/mL, of GMPK.

The first detection reagent may include from about 0.5 µM to about 5.0 µM, about 0.5 µM to about 4.0 µM, about 0.5 µM to about 3.0 µM, about 0.5 µM to about 2.0 µM, about 1.0 µM to about 5.0 µM, about 1.0 µM to about 4.0 µM, about 1.0 µM to about 3.0 µM, about 1.0 µM to about 2.0 µM, about 2.0 µM to about 5.0 µM, about 2.0 µM to about 4.0 µM, about 2.0 µM to about 3.0 µM, about 3.0 µM to about 5.0 µM, about 3.0 µM to about 4.0 µM, or about 4.0 µM to about 5.0 µM, or at least about 0.5 µM, at least about 1.0 µM, at least about 1.5 µM, at least about 2.0 µM, at least about 2.1 µM, at least about 2.2 µM, at least about 2.3 µM, at least about 2.4 µM, at least about 2.5 µM, at least about 2.6 µM, at least about 2.7 µM, at least about 2.8 µM, at least about 2.9 µM, at least about 3.0 µM, at least about 3.5 µM, at least about 4.0 µM, or at least about 5.0 µM of ADP.

The first detection reagent may include from about 0.05 mM to about 50 mM, about 0.05 mM to about 25 mM, about 0.05 mM to about 12.5 mM, about 0.05 mM to about 6.25 mM, about 0.05 mM to about 3.13 mM, about 0.05 mM to about 1.56 mM, about 0.05 mM to about 0.78 mM, about 0.05 mM to about 0.39 mM, about 0.05 mM to about 0.19 mM, about 0.05 mM to about 0.10 mM, about 0.10 mM to about 50 mM, about 0.10 mM to about 25 mM, about 0.10 mM to about 12.5 mM, about 0.10 mM to about 6.25 mM, about 0.10 mM to about 3.13 mM, about 0.10 mM to about 1.56 mM, about 0.10 mM to about 0.78 mM, about 0.10 mM to about 0.39 mM, about 0.10 mM to about 0.20 mM, about 0.20 mM to about 50 mM, about 0.20 mM to about 25 mM, about 0.20 mM to about 12.5 mM, about 0.20 mM to about 6.25 mM, about 0.20 mM to about 3.13 mM, about 0.20 mM to about 1.56 mM, about 0.20 mM to about 0.78 mM, about 0.20 mM to about 0.40 mM, about 0.40 mM to about 50 mM, about 0.40 mM to about 25 mM, about 0.40 mM to about 12.5 mM, about 0.40 mM to about 6.25 mM, about 0.40 mM to about 3.13 mM, about 0.40 mM to about 1.56 mM, about 0.40 mM to about 0.80 mM, about 0.80 mM to about 50 mM, about 0.80 mM to about 25 mM, about 0.80 mM to about 12.5 mM, about 0.80 mM to about 6.25 mM, about 0.80 mM to about 3.13 mM, about 0.80 mM to about 1.56 mM, about 1.56 mM to about 50 mM, about 1.56 mM to about 25 mM, about 1.56 mM to about 12.5 mM, about 1.56 mM to about 6.25 mM, about 1.56 mM to about 3.13 mM, about 3.13 mM to about 50 mM, about 3.13 mM to about 25 mM, about 3.13 mM to about 12.5 mM, about 3.13 mM to about 6.25 mM, about 6.25 mM to about 50 mM, about 6.25 mM to about 25 mM, about 6.25 mM to about 12.5 mM, about 12.5 mM to about 50 mM, about 12.5 mM to about 25 mM, or about 25 mM to about 50 mM, or at least about 0.05 mM, at least about 0.1 mM, at least about 0.2 mM, at least about 0.4 mM, at least about 0.8 mM, at least about 1.56 mM, at least about 3.13 mM, at least about 6.25 mM, at least about 10 mM, at least about 12 mM, at least about 15 mM, at least about 20 mM, at least about 21 mM, at least about 22 mM, at least about 25 mM, at least about 30 mM, at least about 31 mM, at least about 32 mM, at least about 35 mM, at least about 40 mM, at least about 41 mM, at least about 42 mM, at least about 45 mM, or at least about 50 mM of magnesium sulfate or other divalent cation (such as magnesium chloride).

(2) Second Detection Reagent—Luciferase Reaction

The second detection reagent may include a bioluminescent enzyme, a luciferin substrate, and a buffer, such as MOPS, Tris or HEPES.

e. SCS-ADP/ADP-Glo™ Assay

The enzyme ADP-forming succinyl-CoA synthase catalyzes the conversion of succinate, CoA, and ATP to succinyl-CoA, ADP, and Pi. In the SCS-ADP/ADP-Glo™ assay method, the conversion of succinate to succinyl-CoA is performed using a reagent that contains SCS-ADP, ATP, magnesium sulfate or other divalent cation (such as magnesium chloride), and coenzyme A. The ATP present or remaining after the conversion of succinate to succinyl-CoA is depleted using a reagent, such as ADP-Glo™ Reagent (Promega Corp) containing adenylate cyclase and pyrophosphatase. The conversion of ADP to ATP may be performed separately using a reagent that contains pyruvate kinase and phosphoenolpyruvate. The converted ATP may be measured by luminescence using an ATP detection reagent, e.g., a luciferin-luciferase reagent, e.g., Kinase-Glo (Promega Corp). The conversion of ADP to ATP and the generation of luminescence may be performed simultaneously using a reagent such as ADP-Glo™ Kinase Detection Reagent (Promega Corp).

(1) First Detection Reagent—SCS-ADP

The first detection reagent includes SCS-ADP, ATP, coenzyme A, and a buffer, such as MOPS, Tris, or HEPES. The SCS (ADP forming) enzyme may be a SCS (ADP forming) enzyme from a eukaryote or a prokaryote. For example, the SCS (ADP forming) enzyme may be a SCS (ADP forming) enzyme from *Sus scrofa* or *E. coli*. The SCS (ADP forming) enzyme may be encoded by a succinyl-CoA synthase alpha and beta subunit gene sequences from a eukaryote or a prokaryote. For example, the SCS (ADP forming) enzyme may be encoded by a succinyl-CoA synthase alpha and beta subunit gene sequences from *Sus scrofa* or *E. coli*.

The first detection reagent may include from about 0.05 Units/mL to about 1.0 Units/mL, about 0.10 Units/mL to about 1.0 Units/mL, about 0.25 Units/mL to about 1.0 Units/mL, or about 0.50 Units/mL to about 1.0 Units/mL, or at least about 0.05 Units/mL, at least about 0.10 Units/mL, at least about 0.15 Units/mL, at least about 0.20 Units/mL, at least about 0.21 Units/mL, at least about 0.22 Units/mL, at least about 0.23 Units/mL, at least about 0.24 Units/mL, at least about 0.25 Units/mL, at least about 0.26 Units/mL, at least about 0.27 Units/mL, at least about 0.28 Units/mL, at least about 0.29 Units/mL, at least about 0.30 Units/mL, at least about 0.35 Units/mL, at least about 0.40 Units/mL, at least about 0.45 Units/mL, at least about 0.50 Units/mL, or at least about 1.0 Unit/mL of SCS-ADP.

The first detection reagent may include from about 5 μM to about 100 μM, about 5 μM to about 70 μM, about 5 μM to about 50 μM, about 5 μM to about 25 μM, about 10 μM to about 100 μM, about 10 μM to about 70 μM, about 10 μM to about 50 μM, about 10 μM to about 25 μM, about 25 μM to about 100 μM, about 25 μM to about 70 μM, about 25 μM to about 50 μM, about 50 μM to about 100 μM, or about 50 μM to about 70 μM, or at least about 5 μM, at least about 10 μM, at least about 15 μM, at least about 20 μM, at least about 25 μM, at least about 26 μM, at least about 27 μM, at least about 28 μM, at least about 29 μM, at least about 30 μM, at least about 31 μM, at least about 32 μM, at least about 33 μM, at least about 34 μM, at least about 35 μM, at least about 40 μM, at least about 45 μM, at least about 50 μM, at least about 60 μM, at least about 70 μM, at least about 80 μM, at least about 90 μM, or at least about 100 μM of ATP.

The first detection reagent may include from about 5 μM to about 100 μM, about 5 μM to about 70 μM, about 5 μM to about 50 μM, about 5 μM to about 25 μM, about 10 μM to about 100 μM, about 10 μM to about 70 μM, about 10 μM to about 50 μM, about 10 μM to about 25 μM, about 25 μM to about 100 μM, about 25 μM to about 70 μM, about 25 μM to about 50 μM, about 50 μM to about 100 μM, or about 50 μM to about 70 μM, or at least about 5 μM, at least about 10 μM, at least about 15 μM, at least about 20 μM, at least about 25 μM, at least about 26 μM, at least about 27 μM, at least about 28 μM, at least about 29 μM, at least about 30 μM, at least about 31 μM, at least about 32 μM, at least about 33 μM, at least about 34 μM, at least about 35 μM, at least about 40 μM, at least about 45 μM, at least about 50 μM, or at least about 100 μM of coenzyme A.

The first detection reagent may include from about 0.05 mM to about 50 mM, about 0.05 mM to about 25 mM, about 0.05 mM to about 12.5 mM, about 0.05 mM to about 6.25 mM, about 0.05 mM to about 3.13 mM, about 0.05 mM to about 1.56 mM, about 0.05 mM to about 0.78 mM, about 0.05 mM to about 0.39 mM, about 0.05 mM to about 0.19 mM, about 0.05 mM to about 0.10 mM, about 0.10 mM to about 50 mM, about 0.10 mM to about 25 mM, about 0.10 mM to about 12.5 mM, about 0.10 mM to about 6.25 mM, about 0.10 mM to about 3.13 mM, about 0.10 mM to about 1.56 mM, about 0.10 mM to about 0.78 mM, about 0.10 mM to about 0.39 mM, about 0.10 mM to about 0.20 mM, about 0.20 mM to about 50 mM, about 0.20 mM to about 25 mM, about 0.20 mM to about 12.5 mM, about 0.20 mM to about 6.25 mM, about 0.20 mM to about 3.13 mM, about 0.20 mM to about 1.56 mM, about 0.20 mM to about 0.78 mM, about 0.20 mM to about 0.40 mM, about 0.40 mM to about 50 mM, about 0.40 mM to about 25 mM, about 0.40 mM to about 12.5 mM, about 0.40 mM to about 6.25 mM, about 0.40 mM to about 3.13 mM, about 0.40 mM to about 1.56 mM, about 0.40 mM to about 0.80 mM, about 0.80 mM to about 50 mM, about 0.80 mM to about 25 mM, about 0.80 mM to about 12.5 mM, about 0.80 mM to about 6.25 mM, about 0.80 mM to about 3.13 mM, about 0.80 mM to about 1.56 mM, about 1.56 mM to about 50 mM, about 1.56 mM to about 25 mM, about 1.56 mM to about 12.5 mM, about 1.56 mM to about 6.25 mM, about 1.56 mM to about 3.13 mM, about 3.13 mM to about 50 mM, about 3.13 mM to about 25 mM, about 3.13 mM to about 12.5 mM, about 3.13 mM to about 6.25 mM, about 6.25 mM to about 50 mM, about 6.25 mM to about 25 mM, about 6.25 mM to about 12.5 mM, about 12.5 mM to about 50 mM, about 12.5 mM to about 25 mM, or about 25 mM to about 50 mM, or at least about 0.05 mM, at least about 0.1 mM, at least about 0.2 mM, at least about 0.4 mM, at least about 0.8 mM, at least about 1.56 mM, at least about 3.13 mM, at least about 6.25 mM, at least about 10 mM, at least about 12 mM, at least about 15 mM, at least about 20 mM, at least about 21 mM, at least about 22 mM, at least about 25 mM, at least about 30 mM, at least about 31 mM, at least about 32 mM, at least about 35 mM, at least about 40 mM, at least about 41 mM, at least about 42 mM, at least about 45 mM, or at least about 50 mM of magnesium sulfate or other divalent cation (such as magnesium chloride).

(2) Second Detection Reagent—ATP Depletion and ADP Conversion

The second detection reagent may include an ATP depletion reagent and an ADP-to-ATP conversion/detection reagent. The ATP depletion reagent may include an enzyme that depletes ATP from the sample, i.e., the enzyme that depletes ATP from the sample may hydrolyze or convert the ATP in the sample. For example, the enzyme may include an adenylate cyclase and ATP sulfurylase. In some embodiments, the ATP depletion reagent may include adenylate cyclase, pyrophosphatase, magnesium, calmodulin, and a buffer, such as Tris or HEPES buffer pH 7.5. The adenylate cyclase enzyme may be an adenylate cyclase enzyme from a eukaryote or a prokaryote. For example, the adenylate cyclase enzyme may be an adenylate cyclase enzyme from *Bordetella pertussis* toxin. The adenylate cyclase enzyme may be encoded by an adenylate cyclase gene sequence from a eukaryote or a prokaryote. For example, the adenylate cyclase enzyme may be encoded by an adenylate cyclase gene sequence from *Bordetella pertussis* toxin.

The adenylate cyclase enzyme may be encoded by an adenylate cyclase gene sequence from *Bordetella pertussis* toxin. The ATP depletion reagent may include from about 100 µg/mL to about 200 µg/mL, about 125 µg/mL to about 200 µg/mL, about 150 µg/mL to about 200 µg/mL, about 175 µg/mL to about 200 µg/mL, about 100 µg/mL to about 175 µg/mL, about 125 µg/mL to about 175 µg/mL, about 150 µg/mL to about 175 µg/mL, about 100 µg/mL to about 150 µg/mL, about 125 µg/mL to about 200 µg/mL, about 125 µg/mL to about 175 µg/mL, or about 125 µg/mL to about 150 µg/mL, or at least about 100 µg/mL, at least about 105 µg/mL, at least about 110 µg/mL, at least about 115 µg/mL, at least about 120 µg/mL, at least about 125 µg/mL, at least about 130 µg/mL, at least about 135 µg/mL, at least about 140 µg/mL, at least about 145 µg/mL, at least about 150 µg/mL, at least about 155 µg/mL, at least about 160 µg/mL, at least about 165 µg/mL, at least about 170 µg/mL, at least about 175 µg/mL, at least about 180 µg/mL, at least about 185 µg/mL, at least about 190 µg/mL, at least about 195 µg/mL, or at least about 200 µg/mL of adenylate cyclase.

The ATP depletion reagent may be added separately before the ADP-to-ATP conversion/detection reagent. The ATP depletion reaction may be carried out at a temperature for a sufficient time to ensure the complete depletion of ATP, i.e., the complete conversion of all ATP to cAMP.

When all of the ATP is converted to cAMP, the ADP-to-ATP conversion/detection reagent may be added to simultaneously convert ADP to generate ATP and generate luminescence using the generated ATP. The ADP-to-ATP conversion/detection reagent may include pyruvate kinase (PK), phosphoenolpyruvate, magnesium chloride or other divalent cations, a bioluminescent enzyme, a luciferin substrate, and a buffer, such as MOPS, Tris or HEPES. In some embodiments, the ATP-to-ATP conversion/detection reagent may be included in the second reagent. In some embodiments, the ATP-to-ATP conversion/detection reagent may be in a third reagent f. Bioluminescent Enzyme and a Corresponding Substrate Luciferase enzymes produce catalytic products that provide a detectable light product, sensitivity, and allow easy measurement of ATP. However, any bioluminescence generating-enzyme that is ATP-dependent may be used in the methods and compositions of the present invention. At their most basic level, luciferases are defined by their ability to produce luminescence. More specifically, a luciferase is an enzyme that catalyzes the oxidation of a luciferin substrate to produce oxyluciferin and photons.

To date, several classes of luciferases have been identified. Of these, beetle luciferases, such as that of the common firefly (family Lampyridae), form a distinct class with unique evolutionary origins. Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art.

Beetle luciferases, particularly firefly luciferase from the North American firefly *Photinus pyralis*, are well known in the art. The *P. pyralis* luciferase (LucPpy) consists of approximately 550 amino acids of $M_r$ 61 kDa as calculated by the protein encoded by the nucleotide sequence of the gene. However, other firefly luciferases are known, such as *Photuris pennsylvanica* firefly luciferase (LucPpe2; 545 amino acid residues; GenBank 2190534). Thermostable and/or chemostable mutant luciferases derived from LucPpe2 (e.g., LucPpe2m78 (also known as 78-0B10); LucPpe2m90 (also known as 90-1B5); LucPpe2m133 (also known as 133-1B2); LucPpe2m146 (also known as 146-1H2) may be employed, however, any luciferase that meets the limitations set forth herein may be used in the composition, method and kits of the invention. The method of making mutant luciferases from LucPpe is disclosed in PCT/US99/30925.

Isolated and/or purified luciferases are typically used in the present invention. Luciferases that may be used in the methods, compositions and kits described herein include those found in WO 1999/14336, WO 2001/20002, EP 1 124 944, EP 1 224 294, U.S. Pat. Nos. 6,171,808, 6,132,983, and 6,265,177.

Luciferases can be isolated from biological specimens that produce luciferase or from a cell that expresses an exogenous polynucleotide encoding a desired luciferase. Such techniques are well known to those of skill in the art (see U.S. Pat. No. 6,602,677).

The naturally-occurring substrate for beetle luciferases is firefly luciferin, a polytherocyclic organic acid, D-(−)-2-(6'-hydroxy-2'-benzoth-iazolyl)-$\Delta^2$-thiazolin-4-carboxylic acid (D-luciferin). Luciferin may be isolated from nature (e.g., from fireflies) or synthesized. Synthetic luciferin can have the same structure as the naturally occurring luciferin or can be derivatized, so long as it functions analogously. Examples of derivatives of luciferin include D-luciferin methyl ester and other esters of luciferin that are hydrolyzed or acted upon by esterases in a sample to yield luciferin, and naphthyl- and quinolyl-luciferin (Branchini et al., 1989). There are multiple commercial sources for luciferin (e.g., Promega Corp. Madison, Wis.).

The beetle luciferase-catalyzed reaction that yields luminescence (the luciferase-luciferin reaction) involves firefly luciferin, adenosine triphosphate (ATP), magnesium, and molecular oxygen. In the initial reaction, the firefly luciferin and ATP react to form luciferyl adenylate with the elimination of inorganic pyrophosphate. The luciferyl adenylate remains tightly bound to the catalytic site of luciferase. When this form of the enzyme is exposed to molecular oxygen, the enzyme-bound luciferyl adenylate is oxidized to yield oxyluciferin in an electronically excited state. The excited oxidized luciferin emits light on returning to the ground state.

3. METHODS OF DETECTING AND QUANTIFYING SUCCINATE

The present disclosure provides methods for detecting and quantifying succinate. In some embodiments, the methods involve contacting the sample with a first detection reagent to form a first reaction mixture, contacting the first reaction mixture with a second detection reagent to form a second reaction mixture, and detecting luminescence in the second reaction mixture, thereby detecting or determining the presence or amount of succinate in the sample. In some embodiments, the first detection reagent comprises 3-oxoacid CoA-transferase (SCOT), inorganic phosphate, and acetoacetyl-CoA and the second detection reagent comprises succinyl-CoA ligase (SCS) (e.g., SCS-ADP), ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, and the second detection reagent comprises an ATP depletion reagent and an ADP-to-ATP conversion/detection reagent, wherein the first reaction mixture is contacted sequentially with the ATP depletion reagent and subsequently the ADP-to-ATP conversion/detection reagent, wherein the ATP depletion reagent comprises adenylate cyclase and pyrophosphatase, and wherein the ADP-to-ATP conversion/detection reagent comprises pyruvate kinase, phosphoenolpyruvate, a bioluminescent enzyme, and a luciferin substrate. Exemplary ATP depletion reagents and/or ADP-to-ATP conversion/detection reagents are described in U.S. Pat. No. 8,183,007, the disclosure of which is incorporated by reference herein in its entirety.

Any one of the reactions involving any of the enzymes may be restricted or limited by time, enzyme concentration, and/or substrate concentration. Reaction conditions may be adjusted so that the reaction is carried out under conditions that result in about, at least about, or at most about 1, 5, 10, 15, 20, 30, 40, 50, 60, 70, 80, 90, 95, 96, 97, 98, 99 or 100% completion, or any range derivable therein.

For example, any of the reactions described above may be carried out at a temperature between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The reactions described above may be carried out at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

For example, the formation of succinyl-CoA by SCOT, SCS-ADP, and/or SCS-GDP may be carried out at a temperature between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The formation of succinyl-CoA by SCOT, SCS-ADP, and/or SCS-GDP may be carried out at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

For example, the conversion of GDP to ATP by guanylate kinase may be carried out at a temperature between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The conversion of GDP to ATP by guanylate kinase may be carried out at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

For example, the depletion of ATP by adenylate cyclase and pyrophosphatase may be carried out at a temperature between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The depletion of ATP by adenylate cyclase may be carried out at 15° C., 16° C., 17° C., 18° C., 19° C., 20° C., 21° C., 22° C., 23° C., 24° C., 25° C., 26°

C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

For example, the conversion of ADP to ATP by pyruvate kinase may be carried out at a temperature between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The conversion of ADP to ATP by pyruvate kinase and phosphoenolpyruvate may be carried out at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

These temperature conditions and/or the reactions may be maintained for 1 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, or more.

Exemplary ATP depletion and/or ADP to ATP conversion/detection reaction temperatures and conditions are described in U.S. Pat. No. 8,183,007, the disclosure of which is incorporated by reference herein in its entirety.

The amount of ATP generated is determined using a luciferase/luciferin reaction. The ATP is utilized by the luciferase, along with luciferin and sufficient molecular oxygen ($O_2$) to drive the detection of ATP, thereby generating AMP, PPi, oxyluciferin, $CO_2$, and light. The herein described assay generates measurable luminescence. Quantifying the amount of luminescence quantifies the amount of ATP, and thus the amount of succinate in a sample. The luminescence (relative light units; RLUs) measured is proportional to the level of succinate present in the sample. Quantitative ATP values are realized, for example, when the luminescence generated from a test sample, is compared to the luminescence generated from a control sample or to a standard curve determined by using known amounts of ATP and/or succinate, and the same luciferase and reaction conditions (i.e., temperature, pH, etc.). It is understood that quantification involves subtraction of background values or calculating the signal above background. Qualitative ATP values are realized when the luminescence generated from one sample is compared to the luminescence generated from another sample without a need to know the absolute amount of succinate present in the samples. Alternatively, the sample may be depleted of any intrinsic ATP that could interfere with the read out of the detection of ATP.

The herein described method may involve comparing the luminescence results to a control or a comparative sample. For example, the control or comparative sample may contain a known amount of succinate. A standard curve of succinate using a series of calibrating compositions may be performed to correlate the luminescence (RLUs) with the amount of succinate present in the sample.

4. METHODS FOR DETECTING AND QUANTIFYING SUCCINATE FORMING OR GENERATING ENZYMES

The present disclosure also provides methods for detecting and quantifying succinate forming or generating enzymes and/or their activities. The method generates measurable luminescence, which is proportional to the level of succinate that is formed by the succinate forming or generating enzymes in a succinate forming or generating reaction, such as a demethylation reaction, in the sample. For example, the succinate forming or generating reaction may involve contacting the sample, which contains the succinate forming or generating enzyme, with a peptide or protein substrate, such as a histone or peptide substrate, 2-oxoglutarate, Fe(II), and ascorbate to form a succinate reaction mixture. The succinate reaction mixture is then contacted with the first detection reagent and the second detection reagent, as described above. Succinate is formed in the first reaction mixture, i.e., the succinate forming or generating reaction, if the sample contains a succinate forming or generating enzyme, such as 2-oxoglutarate oxygenase, such as a JMJC demethylase or 2OG-dependent dioxygenase.

2-oxoglutarate oxygenases catalyze two electron oxidation reactions by coupling the oxidation of a substrate to the oxidative decarboxylation of 2OG, giving succinate and carbon dioxide co-products. The succinate that is formed in the succinate reaction mixture is converted to succinyl-CoA in the first reaction mixture. Changes in succinate are used to determine the activity of the 2-oxoglutarate oxygenase, such as the activity of JMJC demethylases and/or 2OG-dependent dioxygenase. The succinyl-CoA is converted to ATP, and the amount of ATP generated is determined using a luciferase/luciferin reaction, and the light produced is proportional to the succinate forming or generating enzyme or succinate forming or generating enzyme activity present in the sample.

The methods for detecting and quantifying succinate forming or generating enzymes and/or their activities involve contacting the sample with a peptide, protein, or non-protein substrate, 2-oxoglutarate, Fe(II), and ascorbate to form a succinate reaction mixture, wherein succinate is formed if the sample comprises a succinate forming or generating enzyme; contacting the succinate reaction mixture with a first detection reagent to form a first reaction mixture, and wherein the succinate formed in the previous step is converted to succinyl-CoA; contacting the first reaction mixture with a second detection reagent to form a second reaction mixture, and detecting luminescence in the second reaction mixture, thereby detecting or determining the presence or amount of succinate forming or generating enzyme or succinate forming or generating enzyme activity in the sample. In some embodiments, the succinate formed in the previous step is converted to ATP. In some embodiments, the first detection reagent comprises 3-oxoacid CoA-transferase (SCOT), inorganic phosphate, and acetoacetyl-CoA and the second detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third detection reagent comprising an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate. The 2-oxoglutarate oxygenase may be a Fe(II)-dependent lysine demethylase, such as a JMJC demethylase or a 2OG-dependent dioxygenase.

Quantifying the amount of luminescence quantifies the amount of ATP, and thus the amount of succinate produced by the 2-oxoglutarate oxygenase in a sample. The amount of succinate produced is directly proportional to the 2-oxoglutarate oxygenase and/or 2-oxoglutarate oxygenase activity. Thus, quantitation of ATP allows for quantitation of 2-oxoglutarate oxygenase and/or 2-oxoglutarate oxygenase activity. Quantitative ATP values are realized when the luminescence generated from a test sample, in which succinate is generated by the 2-oxoglutarate oxygenase present in the sample, is compared to the luminescence generated from a control sample or to a standard curve determined by using known amounts of succinate and/or 2-oxoglutarate oxygenase and the same luciferase and reaction conditions (i.e., temperature, pH, etc.). It is understood that quantification involves subtraction of background values or calculating the signal above background. Qualitative ATP values are realized when the luminescence generated from one sample is compared to the luminescence generated from another sample without a need to know the absolute amount of 2-oxoglutarate oxygenase present in the samples.

The herein described method may involve comparing the luminescence results to a control or a comparative sample. For example, the control or comparative sample may contain a known amount of succinate and/or 2-oxoglutarate oxygenase. A standard curve of succinate and/or 2-oxoglutarate oxygenase may be generated to correlate the luminescence (RLUs) with the amount of 2-oxoglutarate oxygenase or 2-oxoglutarate oxygenase activity present in the sample.

Any one of the reactions involving any of the enzymes may be restricted or limited by time, enzyme concentration, and/or substrate concentration. Reaction conditions may be adjusted so that the reaction is carried out under conditions that result in about, at least about, or at most about 1, 5, 10, 15, 20, 30, 40, 50, 60, 70, 80, 90, 95, 96, 97, 98, 99 or 100% completion, or any range derivable therein. For example, the formation of succinate by a 2-oxoglutarate oxygenase, such as JMJC demethylase or 2OG-dependent dioxygenase, may be carried out at between about 15° C. and about 45° C., about 15° C. and about 40° C., about 15° C. and about 35° C., about 15° C. and about 30° C., about 15° C. and about 25° C., about 15° C. and about 20° C., about 20° C. and about 45° C., about 20° C. and about 40° C., about 20° C. and about 35° C., about 20° C. and about 30° C., about 20° C. and about 25° C., between about 25° C. and about 45° C., about 25° C. and about 40° C., about 25° C. and about 35° C., about 25° C. and about 30° C., between about 30° C. and about 45° C., about 30° C. and about 40° C., about 30° C. and about 35° C., between about 35° C. and about 45° C., or between about 35° C. and about 40° C. The formation of succinate by a 2-oxoglutarate oxygenase, such as JMJC demethylase or 2OG-dependent dioxygenase, may be carried out at 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. These temperature conditions may be maintained for 1 min, 5 min, 10 min, 15 min, 20 min, 25 min, 30 min, 35 min, 40 min, 45 min, 50 min, 55 min, 60 min, 65 min, 70 min, 75 min, 80 min, 85 min, 90 min, or more.

(1) Fe(II) Dependent Lysine Demethylases

The 2-oxoglutarate oxygenase may be a Fe(II)-dependent lysine demethylase, such as a histone demethylase. There are several families of histone demethylases, which act on different substrates and play different roles in cellular function. The Fe(II)-dependent lysine demethylases may be a JMJC demethylase. A JMJC demethylase is a histone demethylase containing a JumonjiC (JmjC) domain. The JMJC demethylase may be a member of the KDM3, KDM4, KDM5, or KDM6 family of histone demethylases. The JMJC demethylase may be JMJD1A, JMJD1B, JMJD1C, JMJD2A, JMJD2B, JMJD2C, JMJD2D, JMJD3, JMJD4, JMJD5, JMJD6, JARID1A, JARID1B, JARID1C, JARID1D, UTX, or FBXL11.

(a) KDM3

The KDM3 family includes KDM3A, KDM3B and JMJD1C. KDM3A (also referred to as JHDM2A/JMJD1A/TSGA) can act on mono- and dimethylated H3K9. The KDM3A has roles in spermatogenesis and metabolic functions. Knockdown studies of KDM3A in mice, where the mouse produces reduced levels of KDM3A, resulted in male infertility and adult onset-obesity. Additional studies have indicated that KDM3A may play a role in regulation of androgen receptor-dependent genes as well as genes involved in pluripotency, indicating a potential role for KDM3A in tumorigenesis.

(b) KDM4

The KDM4 family includes KDM4A, KDM4B, KDM4C, and KDM4D, which are also referred to as JMDM3A/JMJD2A, JMDM3B/JMJD2B, JMDM3C/JMJD2C, and JMDM3D/JMJD2D, respectively. These enzymes can act on di- and trimethylated H3K9, H3K36, H1K26. KDM4B and KDM4C have roles in tumorigenesis. The KDM4 family of proteins has been linked to malignant transformation. Specifically, KDM4C amplification has been documented in oesophageal squamous carcinomas, medulloblastomas and breast cancers; amplification of KDM4B has also been found in medulloblastomas. Other gene expression data has also suggested KDM4A, KDM4B, and KDM4C are overexpressed in prostate cancer.

i. JMJD2C

JMJD2C, lysine-specific demethylase 4C, is an enzyme that is encoded by the KDM4C gene in humans. This gene is a member of the Jumonji domain 2 (JMJD2) family and encodes a protein with one JmjC domain, one JumonjiN (JmjN) domain, two PHD-type zinc fingers, and two Tudor domains. This nuclear protein functions as a trimethylation-specific demethylase, converting specific trimethylated histone residues to the dimethylated form. Chromosomal aberrations and increased transcriptional expression of this gene are associated with esophageal squamous cell carcinoma.

ii. JMJD2A

JMJD2A, lysine-specific demethylase 4A, is an enzyme that is encoded by the KDM4A gene in humans. This gene is a member of the Jumonji domain 2 (JMJD2) family and encodes a protein with a JmjN domain, a JmjC domain, a JD2H domain, two TUDOR domains, and two PHD-type zinc fingers. This nuclear protein functions as a trimethylation-specific demethylase, converting specific trimethylated histone residues to the dimethylated form, and as a transcriptional repressor.

(c) KDM5

The KDM5 family includes KDM5A, KDM5B, KDM5C, and KDM5D, which are also referred to as JARID1A/RBP2, JARID1B/PLU-1, JARID1C/SMCX, and JARID1D/SMCY, respectively. These enzymes can act on di- and trimethylated H3K4. The KDM5 protein family may have developmental functions. KDM5A in cell culture systems have been linked to regulation of differentiation, mitochondrial function, cell cycle progression. KDM5B and KDM5C may interact with PcG proteins, which are involved in transcriptional repression.

i. JARID1A

JARID1A, lysine-specific demethylase 5A, is an enzyme that is encoded by the KDM5A gene in humans. The protein is a ubiquitously expressed nuclear protein and binds directly, with several other proteins, to retinoblastoma protein which regulates cell proliferation. It was formally known as Retinoblastoma Binding Protein 2 (RBP2) and also interacts with rhombotin-2 which functions distinctly in erythropoiesis and in T-cell leukemogenesis. Rhombotin-2 is thought to either directly affect the activity of the encoded protein or may indirectly modulate the functions of the retinoblastoma protein by binding to this protein. Alternatively spliced transcript variants encoding distinct isoforms have been found for this gene.

(d) KDM6

The KDM6 family includes KDM6A, KDM6B, and UTY. KDM6A (also referred to as UTX) and KDM6B (also referred to as JMJD3) act on di- and trimethylated H3K27 and have roles in development. Both KDM6A and KDM6B possess tumor-suppressive characteristics. KDM6A knockdowns in fibroblasts lead to an immediate increase in fibroblast population, while KDM6B expressed in fibroblasts induces oncogenes of the RAS_RAF pathway. Deletions and point mutations of KDM6A have been identified as one cause of Kabuki Syndrome, a congenital disorder resulting in intellectual disability. Mutating homologs of KDM6B disrupted gonadal development in *C. elegans*. KDM6B expression is up-regulated in activated macrophages and dynamically expressed during differentiation of stem cells. Depletion of homologs of KDM6A in *D. rerio* have shown decreased expression of HOX genes, which play a role in regulating body patterning during development. In mammalian studies, KDM6A has been shown to regulate HOX genes as well.

(2) 2-Oxoglutarate-Dependent Dioxygenase

The 2-oxoglutarate oxygenase may be a 2-oxoglutarate (2OG)-dependent dioxygenase. In 2OG-dependent dioxygenases, ferrous iron (Fe(II)) is coordinated by a (His)2(Glu/Asp)1 "facial triad" motif. Bidentate coordination of 2OG and water completes a pseudo-octahedral coordination sphere. Following substrate binding, the water ligand is released, yielding an open coordination site for oxygen activation. Upon oxygen binding, a transformation occurs during which 2OG is oxidatively decarboxylated to succinate and the O—O bond is cleaved to form a Fe(IV)-oxo (ferryl) intermediate. This powerful oxidant is then utilized to carry out various reactions, including hydroxylation, halogenation, and demethylation. The 2OG-dependent dioxygenases includes enzymes involved with protein modification (e.g., prolyl 4-hydroxylase, prolyl 3-hydroxylase, lysyl hydroxylase, aspartyl-aspariginyl β-hydroxylase), ribosomal protein hydroxylation (e.g., ribosomal oxygenases YcfD, MINA53 and nucleolar protein 66), oxygen sensing (e.g., PHDs (such as Hypoxia-inducible factor prolyl hydroxylase 2 (also known as"HIF-PH2", "EGLN1", and "PHD2") and Egl nine homolog 2 (EGLN2)), HIFα-specific prolyl 4-hydroxylase, factor-inhibiting HIF (FIH)), DNA and RNA demethylation (e.g., AlkB, ALKBH2/3, FTO), DNA and tRNA hydroxylation (e.g., TET1, ALKBH8), RNA splicing (e.g., JMJD6), carnitine biosynthesis (e.g., $N^\epsilon$ trimethyllysine hydroxylase, γ-butyrobetaine hydroxylase), lipid metabolism (e.g., phytanoyl-CoA hydroxylase, LpxO), thymidine salvage pathway (e.g., thymine hydroxylase), biosynthesis of antibiotics (e.g., clavaminate synthase (CAS), deacetoxycephalosporin C synthase (e.g., DAOCS), deacetylcephalosporin C synthase (e.g., DACS), carbapenem synthase (e.g., CarC), proline 3-hydroxylase, proline 4-hydroxylase), flavonoid biosynthesis (e.g., flavanone 3β-hydroxylase, flavone synthase I, flavonol synthase, anthocyanidin synthase (e.g., ANS), gibberellin biosynthesis (e.g., gibberellin 7-oxidase, gibberellin 20-oxidase, gibberellin 2-oxidase), alkaloid biosynthesis (e.g., desacetoxyvindoline-4-hydroxylase, hyoscyamine 6β-hydroxylase), sulfur metabolism (e.g., taurine/αKG dioxygenase (TauD), alkyl sulfatase (AtsK)), and other activities (e.g., hypophosphite/αKG dioxygenase, 2,4-D/αKG dioxygenase (TfdA), ethylene-forming enzyme). Other enzymes that generate succinate may also be tested, for example succinate dehydrogenase and fumarate reductase.

(a) Tet Enzymes

Ten-eleven translocation methylcytosine dioxygenase 1 (TET1) is a member of the TET family of enzymes that in humans is encoded by the TET1 gene. TET1 catalyzes the conversion of the modified DNA base 5-methylcytosine (5-mC) to 5-hydroxymethylcytosine (5-hmC) coupled with the oxidation of alpha-ketoglutarate (the co-substrate) into succinate and $CO_2$. TET 1 produces 5-hmC by oxidation of 5-mC in an iron and alpha-ketoglutarate dependent manner. The conversion of 5-mC to 5-hmC may be the initial step of active DNA demethylation in mammals.

(b) Hydroxylating Enzymes Involved with HIF1-Alpha Hydroxylation

The 2-oxoglutarate oxygenase may be a hydroxylating enzymes involved with HIF-1α hydroxylation. Hypoxia-inducible factors (HIFs) are transcription factors that respond to changes in available oxygen in the cellular environment, to be specific, to decreases in oxygen, or hypoxia. HIF-1α is a subunit of a heterodimeric transcription factor hypoxia-inducible factor 1 (HIF-1) that is encoded by the HIF1A gene. It is a basic helix-loop-helix PAS domain containing protein, and is considered as the master transcriptional regulator of cellular and developmental response to hypoxia. The dysregulation and overexpression of HIF-1α by either hypoxia or genetic alternations have been heavily implicated in cancer biology, as well as a number of other pathophysiologies, specifically in areas of vascularization and angiogenesis, energy metabolism, cell survival, and tumor invasion. The hydroxylating enzyme may be Hypoxia-inducible factor prolyl hydroxylase 2 (also known as"HIF-PH2", "EGLN1", and "PHD2") or Egl nine homolog 2 (EGLN2)).

b. Peptide or Protein Substrate

The peptide or protein substrate is a substrate that is used by the succinate forming or generating enzyme. The peptide or protein substrate may be a substrate for a histone demethylase, such as a Fe(II)-dependent lysine demethylase or a protein hydroxylase. A code has been developed to indicate the substrate for a particular histone demethylase. The substrate is first specified by the histone subunit (H1, H2A, H2B, H3, H4) and then the one letter designation and number of the amino acid that is methylated. Lastly, the level of methylation is sometimes noted by the addition of "me#", with the numbers being 1, 2, and 3 for monomethylated, dimethylated, and trimethylated substrates, respectively. For example, H3K9me2 is histone H3 with a dimethylated lysine in the ninth position. The peptide or protein substrate may contain a methylation group that is removed during the formation of succinate. For example, the peptide or protein substrate may be histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

c. Non-Protein Substrate

The non-protein substrate is a substrate that is used by the succinate forming or generating enzyme. The non-protein substrate may be a substrate for a 2OG-dependent dioxygenase. The 2OG-dependent dioxygenases may be a Fe(II)-dependent RNA demethylase, a DNA hydroxylase, a synthase, a hydroxylase, or an oxidase involved with antibiotic biosynthesis or biosynthesis of flavonoids, gibberellins, alkaloids and lipid metabolism. The non-protein substrate may contain a methylation group that is removed during the formation of succinate. Examples of non-protein substrates include oligonucleotides containing cytosine modifications in DNA or RNA sequences (1- and 3-alkyl groups), DNA methylation and hydroxymethylation (5mC, 5hmC, 5fC and 5caC), tRNA (5-methoxycarbonylmethyluridine), $N^\epsilon$ trimethyllysine, phytanoyl-CoA, N-α-acetyl-L-arginine, deoxyamidinoproclavaminate, deoxyguanidinoproclavaminate, dihydroclavaminate, proclavamic acid, 3'-methylcephem, 3-exomethylenecephalosporin, 7-aminodeacetoxycephalosporanic acid, cephalexin, deacetoxycephalosporin C, phenylacetyl-7-aminodeacetoxycephalosporanic acid, ampicillin, penicillin G, penicillin N, (3R,5R)-carbapenam-3-carboxylate, (3S,5S)-carbapen-2-am-3-carboxylate, proline, histidine, arginine, tryptophan, isoleucine, flavanones, flavones, flavonols, methylated flavonols, anthocyanins, gibberellins and others.

c. Methods for Detecting or Determining 2-Oxoglutarate Oxygenase

Another aspect of the present disclosure provides for methods for detecting or determining the presence or amount of 2-oxoglutarate oxygenase and/or 2-oxoglutarate oxygenase activity in a sample. The method includes contacting the sample with a peptide, protein, or non-protein substrate, 2-oxoglutarate, Fe(II), and ascorbate to form a succinate reaction mixture, wherein succinate is formed if the sample comprises 2-oxoglutarate oxygenase; the first detection reagent may be added to the 2OG-dependent oxygenase activity assay in order to prevent succinate inhibition of 2OG-dependent oxygenase; contacting the succinate reaction mixture with a first detection reagent to form a first reaction mixture, wherein the succinate formed in step (a) is converted to succinyl-CoA or ATP; contacting the first reaction mixture with a second detection reagent to form a second reaction mixture; and detecting luminescence in the second reaction mixture, thereby detecting or determining the presence or amount of 2-oxoglutarate oxygenase or 2-oxoglutarate oxygenase activity in the sample. In some embodiments, the first detection reagent comprises 3-oxoacid CoA-transferase (SCOT), inorganic phosphate, and acetoacetyl-CoA and the second detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, and the second detection reagent comprises an ATP depletion reagent. In some embodiments, a third detection reagent comprises an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase and the ADP-to-ATP conversion/detection reagent comprises pyruvate kinase, phosphoenolpyruvate, a bioluminescent enzyme, and a luciferin substrate.

d. Methods for Detecting or Determining JMJC Demethylase

Another aspect of the present disclosure provides for methods for detecting or determining the presence or amount of JMJC demethylase and/or JMJC demethylase activity in a sample. The method includes contacting the sample with a peptide or protein substrate, 2-oxoglutarate, Fe(II), and ascorbate to form a succinate reaction mixture, wherein succinate is formed if the sample comprises JMJC demethylase; the first detection reagent may be added to the JMJC demethylase activity assay in order to prevent succinate inhibition of JMJC demethylase; contacting the succinate reaction mixture with a first detection reagent to form a first reaction mixture, wherein the succinate formed in step (a) is converted to succinyl-CoA or ATP; contacting the first reaction mixture with a second detection reagent to form a second reaction mixture; and detecting luminescence in the second reaction mixture, thereby detecting or determining the presence or amount of JMJC demethylase or JMJC demethylase activity in the sample. In some embodiments, the first detection reagent comprises 3-oxoacid CoA-transferase (SCOT), inorganic phosphate, and acetoacetyl-CoA, and the second detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprises an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase and the ADP-to-ATP conversion/detection reagent comprises pyruvate kinase, phosphoenolpyruvate, a bioluminescent enzyme, and a luciferin substrate.

e. Methods for Detecting or Determining 2OG-Dependent Dioxygenase

Another aspect of the present disclosure provides for methods for detecting or determining the presence or amount of 2OG-dependent dioxygenase and/or 2OG-dependent dioxygenase activity in a sample. The method includes contacting the sample with a peptide, protein, or non-protein substrate, 2-oxoglutarate, Fe(II), and ascorbate to form a succinate reaction mixture, wherein succinate is formed if the sample comprises 2OG-dependent dioxygenase; the first detection reagent may be added to the 2OG-dependent dioxygenase activity assay in order to prevent succinate inhibition of 2OG-dependent dioxygenase; contacting the succinate reaction mixture with a first detection reagent to form a first reaction mixture, wherein the succinate formed in step (a) is converted to succinyl-CoA or ATP; contacting the first reaction mixture with a second detection reagent to form a second reaction mixture; and detecting luminescence in the second reaction mixture, thereby detecting or determining the presence or amount of 2OG-dependent dioxygenase or 2OG-dependent dioxygenase activity in the sample. In some embodiments, the first detection reagent comprises 3-oxoacid CoA-transferase (SCOT), inorganic phosphate, and acetoacetyl-CoA and the second detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprises an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate.

5. METHODS OF DETERMINING SUCCINATE IN CELLULAR AND TISSUE EXTRACTS

Another aspect of the present disclosure provides for methods of detecting and quantifying succinate in cellular and tissue extracts. The methods involve removing any ATP present in the sample and converting the succinate present in the extract to succinyl-CoA, using any of the methods described above. For example, SCOT may be used to convert the succinate to succinyl-CoA. The succinyl-CoA that is generated by the SCOT reaction may be converted by SCS-ADP to ATP, which is detected by luminescence.

6. METHODS FOR DETECTING OR DETERMINING TET AND/OR TET ACTIVITY

Another aspect of the present disclosure provides for methods for detecting or determining the presence or amount of Tet and/or Tet activity in a sample. The method includes contacting the sample with a DNA oligonucleotide containing a 5mC, a 5hmC, a 5fC or a 5caC modification, 2-oxoglutarate, Fe(II), and ascorbate to form a Tet succinate reaction mixture, wherein succinate is formed if the sample comprises Tet; contacting the Tet succinate reaction mixture with a first detection reagent to form a first reaction mixture, wherein the succinate formed in step (a) is converted to succinyl-CoA or ATP; contacting the first reaction mixture with a second detection reagent to form a second reaction mixture; and detecting luminescence in the second reaction mixture, thereby detecting or determining the presence or amount of Tet or Tet activity in the sample. In some embodiments, the first detection reagent may be added to the Tet succinate reaction mixture to prevent succinate inhibition of Tet by high levels of succinate (i.e., mM levels).

In some embodiments, the first detection reagent comprises 3-oxoacid CoA-transferase (SCOT), inorganic phosphate, and acetoacetyl-CoA and the second detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second detection reagent comprises guanylate kinase (GMPK), ADP, a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprises an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate.

7. METHODS OF SCREENING FOR MODULATORS OF 2-OXOGLUTARATE OXYGENASE

The herein described methods for detecting or determining the presence or amount of succinate may be incorporated into methods of screening candidate modulators of 2-oxoglutarate oxygenase activity. The herein described methods of screening for modulators of 2-oxoglutarate oxygenase activity make use of the generation of measurable luminescence, wherein the luminescence (relative light units; RLUs) measured is proportional to the level of succinate in the sample and the 2-oxoglutarate oxygenase activity. The sample may be contacted with a compound of interest.

The methods include contacting the sample with the compound to form a test sample, wherein the sample comprises a 2-oxoglutarate oxygenase; contacting the test sample with a peptide, protein, or non-protein substrate, 2-oxoglutarate, Fe(II), and ascorbate to form a succinate reaction mixture; contacting the succinate reaction mixture with a first detection reagent to form a first reaction mixture, whereby the succinate formed in step (a) is converted to succinyl-CoA or ATP; contacting the first reaction mixture with a second or ATP detection reagent to form a second reaction mixture; detecting luminescence in the second reaction mixture; and comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity. In some embodiments, the first detection reagent comprises 3-oxoacid CoA-transferase (SCOT), inorganic phosphate, and acetoacetyl-CoA, and the second or ATP detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second or ATP detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprises an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate.

a. Methods of Screening for Modulators of JMJC Demethylase Activity

Another aspect of the present disclosure provides for methods for determining whether a compound modulates JMJC demethylase activity in a sample. The methods include contacting the sample with the compound to form a test sample, wherein the sample comprises a JMJC demethylase; contacting the test sample with a peptide or protein substrate, 2-oxoglutarate, Fe(II), and ascorbate to form a succinate reaction mixture; contacting the succinate reaction mixture with a first detection reagent to form a first reaction mixture, whereby the succinate formed in step (a) is converted to succinyl-CoA or ATP; contacting the first reaction mixture with an second or ATP detection reagent to form a second reaction mixture; detecting luminescence in the second reaction mixture; and comparing the luminescence in the second reaction mixture to luminescence in a control sample, wherein if the luminescence in the second reaction mixture is different from the luminescence in a control sample, the compound is identified as being a modulator of JMJC demethylase activity. In some embodiments, the first detection reagent comprises 3-oxoacid CoA-transferase (SCOT), inorganic phosphate, and acetoacetyl-CoA and the second or ATP detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second or ATP detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprising an ADP-to-ATP conversion/detection reagent; wherein the first reaction mixture is contacted sequentially with the ATP depletion reagent, and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate.

b. Methods of Screening for Modulators of 2OG-Dependent Dioxygenase Activity

Another aspect of the present disclosure provides for methods for determining whether a compound modulates 2OG-dependent dioxygenase activity in a sample. The methods include contacting the sample with the compound to form a test sample, wherein the sample comprises a 2OG-dependent dioxygenase; contacting the test sample with a peptide, protein, or non-protein substrate, 2-oxoglutarate, Fe(II), and ascorbate to form a succinate reaction mixture; contacting the succinate reaction mixture with a first detection reagent to form a first reaction mixture, whereby the succinate formed in step (a) is converted to succinyl-CoA or ATP; contacting the first reaction mixture with a second or ATP detection reagent to form a second reaction mixture; detecting luminescence in the second reaction mixture; and comparing the luminescence in the second reaction mixture to luminescence in a control sample, wherein if the luminescence in the second reaction mixture is different from the luminescence in a control sample, the compound is identified as being a modulator of 2OG-dependent dioxygenase activity. In some embodiments, the first detection reagent comprises 3-oxoacid CoA-transferase (SCOT), inorganic phosphate, and acetoacetyl-CoA and the second or ATP detection reagent comprises succinyl-CoA ligase (SCS), e.g., SCS-ADP, ADP, a bioluminescent enzyme, and a luciferin substrate. In some embodiments, the first detection reagent comprises 3-oxoacid CoA-transferase (SCOT), inorganic phosphate, acetoacetyl-CoA, succinyl-CoA ligase (SCS) (e.g., SCS-ADP), ADP, magnesium chloride, and the second detection reagent comprises a bioluminescent enzyme and a luciferin substrate. In some embodiments, the first detection reagent comprises SCS-GDP, GTP, and coenzyme A, and the second or ATP detection reagent comprises guanylate kinase (GMPK), ADP, a bioluminescent enzyme, and a luciferin substrate. In some embodiments, the first detection reagent comprises SCS-GDP, GTP, coenzyme A, guanylate kinase (GMPK), and ADP, and the second detection reagent comprises a bioluminescent enzyme, and a luciferin substrate. In some embodiments, the first detection reagent comprises ADP forming succinyl-CoA ligase (SCS-ADP), ATP, and coenzyme A, the second detection reagent comprises an ATP depletion reagent, and a third reagent comprising an ADP-to-ATP conversion/detection reagent; wherein the first reaction mixture is contacted sequentially with the ATP depletion reagent and the ADP-to-ATP conversion/detection reagent, and wherein the ATP depletion reagent comprises adenylate cyclase and pyrophosphatase, and the ADP-to-ATP conversion/detection reagent comprises pyruvate kinase, phosphoenolpyruvate, a bioluminescent enzyme, and a luciferin substrate.

c. Candidate Modulator

A variety of different types of libraries of candidate modulator compounds can be used and screened in the method of the present invention. A candidate modulator may be an antibody, a small molecule, a drug, a peptide, a nucleic acid, an oligosaccharide, or an inorganic compound. An identified modulator compound may be derived from a library of candidate modulator compounds. A library of compounds may be a combinatorial library. The method may comprise stimulating a host cell to express the candidate modulator compound. The candidate modulators may be compared with selective inhibitors, such as histone demethylase JMJD inhibitors JIB-04 (E)-N-(5-Chloro-pyridin-2-yl)-N'-(phenyl-pyridin-2-yl-methylene)-hydrazine) or IOX 1 (5-carboxy-8HQ; also known as 8-Hydroxy-5-quinolinecarboxylic acid).

Modulators identified by the herein described method, may be compounds showing pharmacological activity or therapeutic activity. Compounds with pharmacological activity are able to enhance or interfere with the activity of a JMJC demethylase or a fragment thereof. The compounds having the desired pharmacological activity may be administered in a physiologically acceptable carrier to a host.

The agents may be administered in a variety of ways, orally, parenterally e.g., subcutaneously, intraperitoneally, intravascularly, etc. Depending upon the manner of introduction, the compounds may be formulated in a variety of ways. The concentration of a therapeutically active compound in the formulation may vary from about 0.1-100 wt %. Modulators of the present invention can be administered at a rate determined by the LD50 of the modulator, and the side-effects of the modulator at various concentrations, as applied to the mass and overall health of the subject. Administration can be accomplished via single or divided doses.

The identified modulators of the invention may be used alone or in conjunction with other agents that are known to be beneficial in treating or preventing human diseases that are mediated by DNA methylation, demethylation, and/or 5-mC hydroxylation. The modulators of the invention and another agent may be co-administered, either in concomitant therapy or in a fixed combination, or they may be administered at separate times.

d. Control

It may be desirable to include a control sample in any of the herein described methods. The control sample may be a sample that has not been contacted with the compound. The control sample may be analyzed concurrently with the test sample, as described above. The results obtained from the test sample may be compared to the results obtained from the control sample. Standard curves may be provided, with which assay results for the test sample may be compared. Such standard curves present levels of marker as a function of assay units, i.e. luminescent signal intensity.

8. LUMINESCENCE DETECTION

The luminescence generated by a luciferase-luciferin reaction is typically detected with a luminometer although other detection means may be used. The presence of light greater than background level indicates the presence of ATP, and thus succinate and/or 2-oxoglutarate oxygenase, in the sample. The background level of luminescence is typically measured in the same matrix, but in the absence of the sample. Suitable control reactions are readily designed by one of skill in the art. Luciferases may allow for multiple analyses of a sample over time or analysis of many samples over time. Optionally, the luciferases used in the compositions and methods of the invention have enhanced thermostability and/or chemostability properties.

9. VARIANT ENZYMES

A full length luciferase, 2-oxoglutarate oxygenase, such as JMJC demethylase or 2OG-dependent dioxygenase, 3-oxoacid CoA-transferase, or succinate-CoA ligase variant will have at least about 80% amino acid sequence identity, at least about 81% amino acid sequence identity, such as at least about 82%, 83%, 84%, 85%, 86%, 87%, 88%, 89%, 90%, 91%, 92%, 93%, 94%, 95%, 96%, 97%, 98%, or 99% amino acid sequence identity with a corresponding full-length native luciferase, 2-oxoglutarate oxygenase, such as JMJC demethylase or 2OG-dependent dioxygenase, SCOT, or SCS. Ordinarily, variant fragments are at least about 50 amino acids in length, often at least about 60 amino acids in length, more often at least about 70, 80, 90, 100, 150, 200, 300, 400, 500 or 550 amino acids in length, or more and retain the ability to generate luminescence, transfer phosphate groups, transfer glucose, and hydroxylate. A full length luciferase, 2-oxoglutarate oxygenase, such as JMJC demethylase or 2OG-dependent dioxygenase, SCOT, SCS, fragment thereof, or variant thereof may be fused to heterologous amino acid sequences and still be functional in the invention.

For example, full length beetle luciferase, 2-oxoglutarate oxygenase, such as JMJC demethylase or 2OG-dependent dioxygenase, SCOT, or SCS, fragments thereof or variants thereof used in the compositions and methods of the present invention may be purified from a native source or prepared by a number of techniques, including (1) chemical synthesis, (2) enzymatic (protease) digestion of luciferase, and (3) recombinant DNA methods. Chemical synthesis methods are well known in the art, as are methods that employ proteases to cleave specific sites. To produce the enzymes, variant enzymes or fragments thereof, DNA encoding the enzymes, variants and fragments may be prepared and then expressed in a host organism, such as *E. coli*. Methods such as endonuclease digestion or polymerase chain reaction (PCR) allow one of skill in the art to generate an unlimited supply of well-defined fragments. The activity of a variant or fragment may vary from that of the native enzyme.

Any type of amino acid substitution, insertion or deletion, or combination thereof may be used to generate a variant luciferase, 2-oxoglutarate oxygenase, such as JMJC demethylase or 2OG-dependent dioxygenase, SCOT, or SCS with a conservative amino acid substitution is more likely to retain activity. Conservative substitutions whereby an amino acid of one class is replaced with another amino acid of the same type fall within the scope of the invention if the substitution does not impair enzyme activity.

Non-conservative substitutions that affect (1) the structure of the polypeptide backbone, such as a β-sheet or a-helical conformation, (2) the charge or (3) hydrophobicity, or (4) the bulk of the side chain of the target site might modify luciferase function. Residues are divided into groups based on common side-chain properties.

Variant luciferase, 2-oxoglutarate oxygenase, such as JMJC demethylase or 2OG-dependent dioxygenase, SCOT, or SCS genes or gene fragments may be made using methods known in the art such as oligonucleotide-mediated (site-directed) mutagenesis, alanine scanning, and PCR mutagenesis (site-directed mutagenesis) cassette mutagenesis, restriction selection mutagenesis, PCR mutagenesis or other known techniques can be performed on the cloned DNA to produce the variant DNA.

10. SAMPLE

The disclosed methods may be used with any sample that is suspected of containing succinate or derivatives thereof. In some embodiments, the disclosed methods may be used with non-biological or biological samples. Succinate and derivatives thereof are used for the manufacturing of various industrial products, such as products made in the pharmaceutical or cosmetic industries. In some embodiments, the disclosed methods may be used in testing in the manufacturing of pharmaceuticals, cosmetics, detergents, surfactants, plastics, polymers, lubricants, and resins (paint). The disclosed methods may be used in food and beverage, such as wine, testing where succinate is used as a quality indicator. The disclosed methods may be used with samples containing biological components. The sample may comprise cells and/or tissue. The sample may comprise heterogeneous mixtures of components (including intact cells, cell extracts, cell lysates, bacteria, viruses, organelles, and mixtures thereof) or a single component or homogeneous group of components (e.g., natural or synthetic amino acid, nucleic acid or carbohydrate polymers, or lipid membrane complexes). The compounds are generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (non-recombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cells may have been genetically modified via recombinant techniques.

The sample may include a succinate forming or generating enzyme. The succinate forming or generating enzyme may be 2-oxoglutarate oxygenase, such as a JMJC demethylase or 2OG-dependent dioxygenase, as described above. In some embodiments, the succinate forming or generating enzyme may be a native or recombinant a succinate forming or generating enzyme. For example, the sample may include a native or recombinant demethylase. In some embodiments, the succinate forming or generating enzyme is purified or isolated. For example, the sample may include a purified or isolated demethylase.

11. COMPONENTS

Methods and compositions may involve a purified, or substantially pure, substrates, such as a peptide, protein, or non-protein substrates, 2-oxoglutarate, Fe(II), ascorbate, inorganic phosphate, acetoacetyl-CoA, ADP, and a luciferin substrate, and/or enzyme, such as bioluminescent enzyme, such as a luciferase, 2-oxoglutarate oxygenase, such as JMJC demethylase or 2OG-dependent dioxygenase, SCOT, and SCS. Such protocols are known to those of skill in the art. In certain embodiments, purification may result in a molecule that is about or at least about 70, 75, 80, 85, 90, 95, 96, 97, 98, 99, 99.1, 99.2, 99.3, 99.4, 99.5, 99.6, 99.7 99.8, 99.9% or more pure, or any range derivable therein, relative to any contaminating components (w/w or w/v).

12. KIT

Kits for analysis of succinate are provided herein. Such kits comprise reagents for analysis of succinate. Such kits may comprise an active SCOT and active SCS-ADP; active SCS-GDP and active guanylate kinase; and/or active SCS-ADP, active adenylate cyclase, active pyrophosphatase, and active pyruvate kinase. Such kits may further comprise one or more reference succinate samples; a buffer, instructions, a bioluminescent enzyme and a luciferin substrate. The kit components, compositions and buffers may also be modified by the addition of suitable components, such as ADP, GDP, ATP, inorganic phosphate, acetoacetyl-CoA, a divalent cation, such as magnesium, for example magnesium chloride, calmodulin, phosphoenolpyruvate, salts, chelators, etc. Suitable kit components, compositions and buffers that may be used in the described methods may also be obtained commercially. The different components may comprise subsets of these parts and may be combined in any way that either facilitates the application of the invention or prolongs storage life.

Kits for analysis of a succinate forming or generating enzyme are provided herein. Such kits comprise reagents for analysis of the succinate forming or generating enzyme. Such kits comprise reagents for analysis of succinate, as described above, a peptide, protein, or non-protein substrate, 2-oxoglutarate, Fe(II), one or more reference succinate samples; a buffer, instructions, a bioluminescent enzyme and a luciferin substrate. The kit components, compositions and buffers may also be modified by the addition of suitable components, such as ADP, inorganic phosphate, acetoacetyl-CoA salts, chelators, etc. Suitable kit components, compositions and buffers that may be used in the described methods, such as peptide, protein, or non-protein substrates, 2-oxoglutarate and Fe(II), may also be obtained commercially. The different components may comprise subsets of these parts and may be combined in any way that either facilitates the application of the invention or prolongs storage life.

In some embodiments, the kit comprises a separate container comprising lyophilized luciferase. In some embodiments, the container comprising lyophilized luciferase further comprises lyophilized luciferin or a derivative thereof that is a luciferase substrate.

One or more reagents may be supplied in a solid form or liquid buffer that is suitable for inventory storage, and later for addition into the reaction medium when the method of using the reagent is performed. Suitable packaging is provided.

(1) Containers/Vessels

The reagents included in the kits may be supplied in containers of any sort such that the life of the different components are preserved and are not adsorbed or altered by the materials of the container. For example, sealed glass ampules may contain lyophilized luciferase or buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port such as a bottle having a stopper that may be pierced by a hypodermic injection needle. Other containers may have two compartments that are separated by a readily removable membrane that upon removal permits the components to mix. Removable membranes may be glass, plastic, rubber, etc.

(2) Instructional Materials

The kits may also be supplied with instructional materials. Instructions may be printed on paper or other substrate and/or may be supplied as an electronic-readable medium such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

13. EXAMPLES

The present invention may be utilized as illustrated by the following non-limiting examples.

Example 1

Materials

The following were used in the Examples described herein: 3-oxoacid CoA-transferase (UniProtKB/Swiss-Prot # Q29551); ADP-forming succinyl-CoA synthase (UniProtKB/Swiss-Prot #O19069 and O97580 for *Sus scrofa* SCS-ADP; UniProtKB/Swiss-Prot # P0A836 and P0AGE9 for *E. coli* SCS-ADP); Acetoacetyl-Coenzyme A sodium salt hydrate (Sigma Catalog number A1625); GDP-forming succinyl-CoA synthase (NCBI Reference Sequences: NP_999574.1 and XP_003132357.3); Sodium succinate dibasic (Sigma Catalog number 14160); α-Ketoglutarate potassium salt (Sigma Catalog number K2000); Ultra pure GTP (Promega); Coenzyme A trilithium salt (Sigma Catalog number C3019); Guanylate kinase (NCBI Reference Sequence: NP_001152884.1 and NP_001152885.1); Pyruvate kinase from rabbit skeletal muscle (Sigma Catalog number P9136); Phosphoenolpyruvate (Sigma Catalog number P7127); and Adenylate Cyclase (AC): a recombinant fragment of *B. pertussis* toxin that contains the active AC portion and demonstrated activity using ATP as substrate (Promega Corporation). ADP-Glo™ Kinase assay (Promega cat # V9101).

The reagents in Table 1 were used in the Examples described herein.

TABLE 1

| Reagent Name | Contents |
| --- | --- |
| Method 1 Bioluminescent Succinate Detection Buffer I | MOPS pH 8.0, 500 mM Potassium phosphate (monobasic/dibasic), and 80 μM acetoacetyl-CoA |
| Bioluminescent Succinate Detection Solution I | 150 ng/μL of SCOT in 20 mM HEPES pH 7.5, 150 mM NaCl, 1 mM DTT, and 50% (v/v) Glycerol |
| Bioluminescent Succinate Detection Reagent I | contains 10 μL of Bioluminescent Succinate Detection Solution I in 1 mL Bioluminescent Succinate Detection Buffer I |
| Bioluminescent Succinate Detection Solution II (ADP-to-ATP Conversion Reagent) | 8.14 U/mL of SCS-ADP in 20 mM HEPES pH 7.5, 150 mM NaCl, 1 mM DTT, and 50% (v/v) Glycerol |
| Kinase Glo ® Reagent (Promega Corp) | Mix Kinase-Glo ® substrate and Nucleotide Detection Buffer |
| Bioluminescent Succinate Detection Reagent II (ADP-to-ATP Conversion Reagent) | 5 μL of Bioluminescent Succinate Detection Solution II in 1 mL of Kinase-Glo ® Reagent |
| Method 2 Bioluminescent Succinate Detection Solution I (SCS-GDP/GMPK method) | 1 μg/μL of SCS-GDP in 20 mM HEPES pH 7.5, 150 mM NaCl, 1 mM DTT, and 50% (v/v) Glycerol. |
| Bioluminescent Succinate Detection Reagent I (SCS-GDP/GMPK method) | 3.2 μL of Bioluminescent Succinate Detection Solution I (SCS-GDP) in 1 mL of 50 mM Tris-HCl, pH 7.5, and 10 mM MgCl₂ |
| Bioluminescent Succinate Detection Solution II (SCS-GDP/GMPK method) | 100 μg/mL of guanylate kinase in water |
| Bioluminescent Succinate Detection Reagent II (SCS-GDP/GMPK method) | 1.6 μL of Bioluminescent Succinate Detection Solution II (GMPK) in 1 mL of Kinase-Glo ® Reagent |
| Method 3 Bioluminescent Succinate Detection Solution I (SCS-ADP/ADP-Glo ™ method) | 220 U/mL of SCS-ADP in ammonium sulfate |
| Bioluminescent Succinate Detection Reagent I (SCS-ADP/ADP-Glo ™ method) | 1.25 μL of Bioluminescent Succinate Detection Solution I (SCS-ADP/ADP-Glo ™ method) in 1 mL of 50 mM Tris-HCl, pH 7.5, 10 mM MgCl₂, 30 μM coenzyme A, and 30 μM ATP |
| Method 4 Bioluminescent Succinate Detection Buffer I | MOPS pH 7.5, 250 mM Potassium phosphate (monobasic/dibasic), 1.5 mM MgCl₂, 10 μM ADP, and 20 μM acetoacetyl-CoA |
| Bioluminescent Succinate Detection Solution I | 230 ng/μL of SCOT and 156 ng/μL SCS-ADP in 20 mM HEPES pH 7.5, 150 mM NaCl, 1 mM DTT, and 50% (v/v) Glycerol |
| Kinase Glo ® Reagent (Promega Corp) | Mix Kinase-Glo ® substrate and Succinate Detection Buffer |

Example 2

Cloning and Expression of 3-Oxoacid CoA-Transferase (SCOT) and Succinyl-CoA Synthetases (SCS-ADP and SCS-GDP)

The 3-Oxoacid CoA-Transferase gene of *Sus scrofa* was cloned as a synthetic codon-optimized sequence from Genscript. The expressed protein ranged from amino acid 40 to 517 and included an 8× His tag on the C-terminus. The protein was expressed in *E. coli* KRX cells (Promega) from the T7 promoter of Flexi vector pF1K (Promega). The KRX strain was grown in Terrific Broth at 25° C. and induced at an $OD_{600}$=~1.5 with 0.1% rhamnose. Growth at 25° C. continued overnight. The SCOT enzyme was purified over HisLink resin (Promega), and the purified eluate was dialyzed into 25 mM HEPES, pH 7.5, 25 mM NaCl, 1 mM DTT, and 50% glycerol. The size of the purified enzyme was verified via SDS-PAGE.

The Succinyl-CoA Synthetase alpha and beta subunit genes of *Sus scrofa* (SCS-ADP and SCS-GDP) were cloned as synthetic codon-optimized sequences from Genscript. The SCS alpha protein includes a 6× His tag on the N-terminus. The proteins were expressed in *E. coli* KRX cells (Promega) from the T7 promoter of Flexi vector pF1K (Promega). The KRX strain was grown in Terrific Broth at 25° C. and induced at an OD600=~1.5 with 0.1% rhamnose. Growth at 25° C. continued overnight. The SCS-ADP and SCS-GDP enzymes were purified over HisLink resin (Promega), and the purified eluates were dialyzed into 25 mM HEPES, pH 7.5, 25 mM NaCl, 1 mM DTT. The size of the purified enzymes was verified via SDS-PAGE.

*E. coli* (SCS-ADP) was cloned directly out of W3110 *E. coli* genomic DNA a single bi-cistronic sequence. The alpha protein includes a 6× His tag on the C-terminus Expression and purification were performed as above.

Example 3

Figure 2:
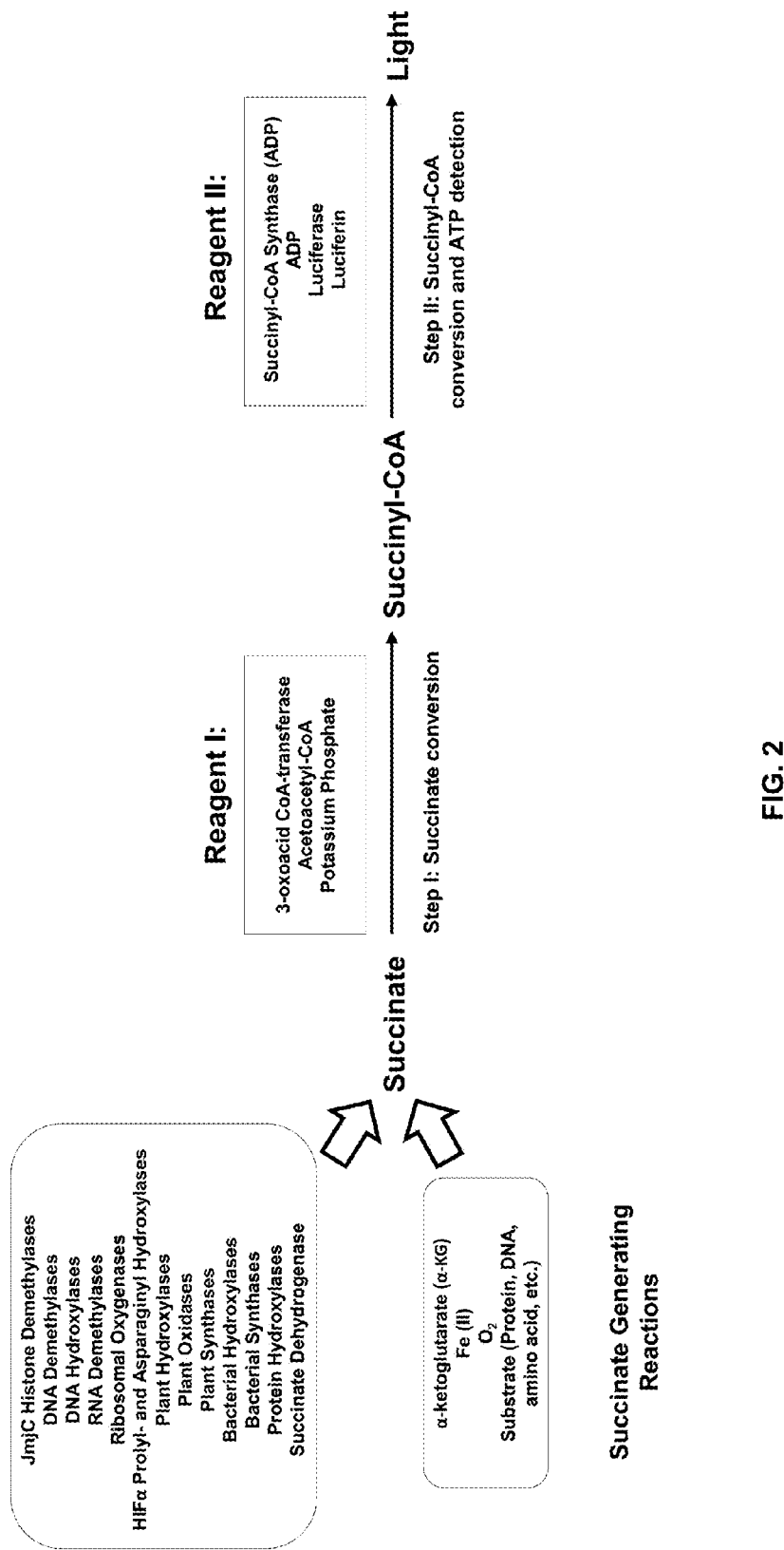
FIG. 2 illustrates a succinate detection assay using 3-oxoacid CoA-transferase/Succinyl-CoA Ligase (Method 1) after a succinate producing enzymatic reaction.
Figure 3:
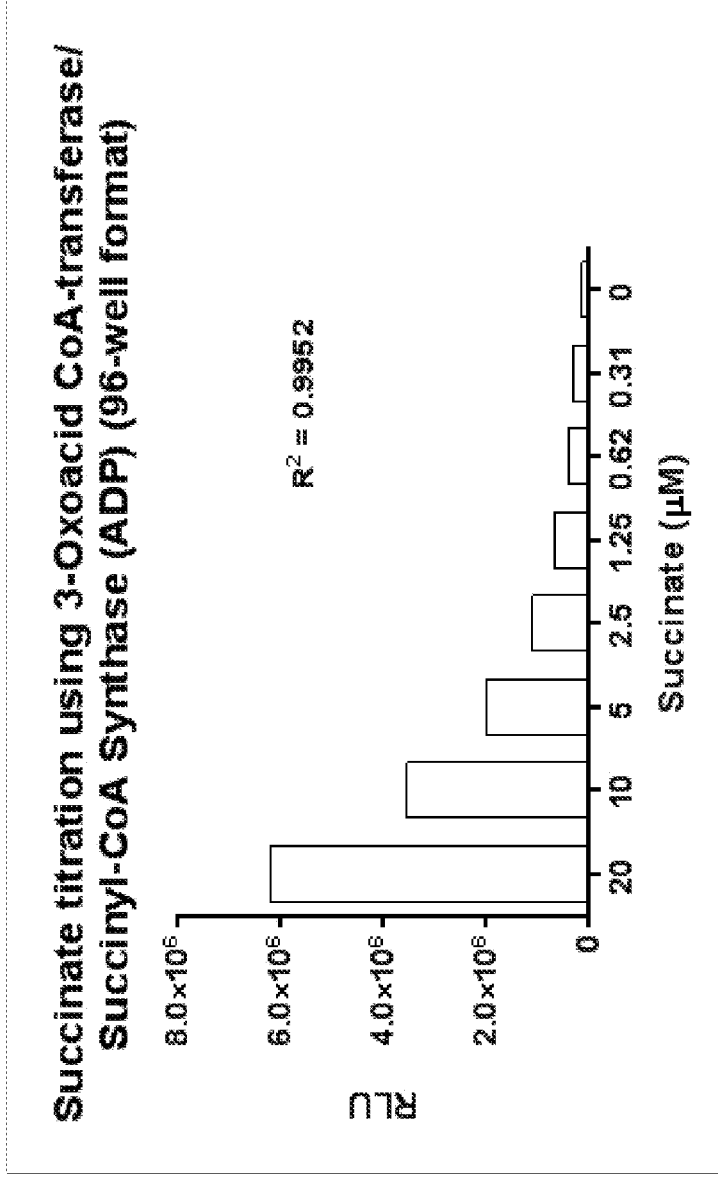
FIG. 3 illustrates a succinate titration curve using Method 1.

Succinate Detection Assay Using 3-Oxoacid CoA Transferase and ADP-Forming Succinyl-CoA Synthase The succinate detection assay in FIG. 2 was performed generally in two steps as follows. The succinate titration was performed in 25 µL containing 1× Demethylase Reaction Buffer (50 mM HEPES, pH 7.5, 0.01% Tween-20, 10 µg/mL BSA, 100 µM ascorbate, 10 µM Fe(II), 10 µM α-ketoglutarate). 25 µL of Bioluminescent Succinate Detection Reagent I was added to the succinate samples, and the mixture was incubated for 60 min at room temperature (~23° C.). To detect succinyl-CoA, 50 µL of Bioluminescent Succinate Detection Reagent II was added, and the mixture was incubated for 60 min at room temperature before luminescence was detected on a luminometer. The succinate titration shown in FIG. 3 was performed in 96-well low volume plates (Corning Costar®, cat#3693).

Example 4

JumonjiC Demethylase System

Figure 4A:
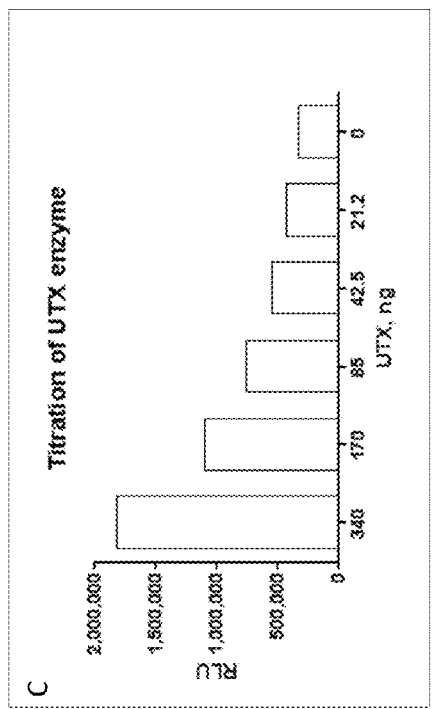
FIGS. 4A-4C illustrate JMJC demethylase titration curves for JMJD2C, JARID1A, and UTX enzymes detected with the succinate detection assay described in FIG. 2.
Figure 4B:
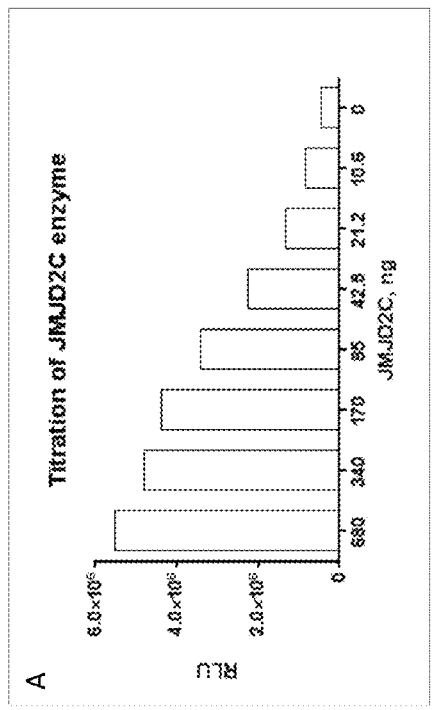
Figure 4C:
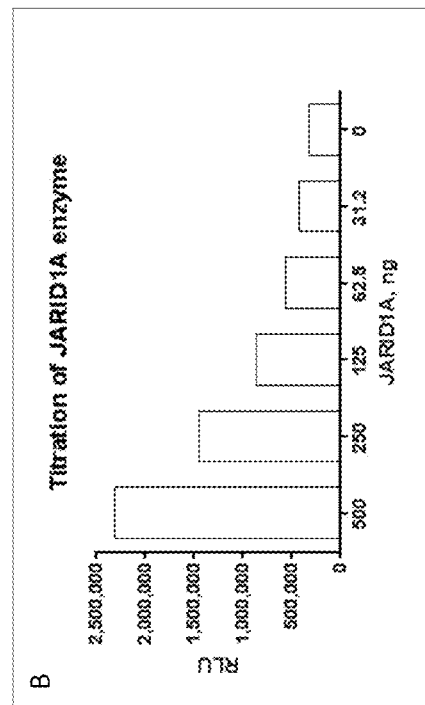

The method of the present invention was used to assay representative demethylating enzymes including, but not limited to, JMJD2C (BPS Bioscience, cat #50105) with substrate Lys(Me3)9-histone H3 (1-21) (Anaspec, cat #64452), JARID1A (BPS Bioscience, cat #50110) with substrate Lys(Me3)4-histone H3 (1-21) (Anaspec, cat #64194) and UTX (Cayman Chemical, cat #10774) with substrate Lys(Me3)27-histone H3 (23-34) (Anaspec, cat #64378). Each enzyme was titrated separately, and the reaction was performed in the Demethylase Reaction Buffer. Succinate was converted using Bioluminescent Succinate Detection Reagent I followed by the conversion of ADP to ATP and the detection of ATP using the Bioluminescent Succinate Detection Reagent II. Briefly, 5 µL of serially diluted JMJC demethylase in 50 mM HEPES, pH 7.5, 0.01% Tween-20 and 10 µg/mL BSA was added to wells of a 96-well low volume plate. The JMJC demethylase reaction was started by adding 5 µL of a mixture containing 2× Demethylase Reaction Buffer and 20 µM trimethylated histone H3 peptide substrate. After incubation of 60 min at room temperature, 10 µL of the succinate to succinyl-CoA conversion reagent (Bioluminescent Succinate Detection Reagent I) was added, mixed for 2 min on an orbital shaker, and then incubated at room temperature for 60 min. To the samples, 20 µL of Bioluminescent Succinate Detection Reagent II was added, and the samples were incubated at room temperature for 60 min. Luminescence was then detected on a luminometer (FIG. 4). It was found that succinate generated in the reaction was proportional to the demethylation and/or enzyme activity. Thus, the method of the present invention may be used to screen for compounds that alter the activity of all enzymes involved in histone demethylation.

Example 5

Determination of Substrate Specificity of JMJC Demethylases

Figure 5:
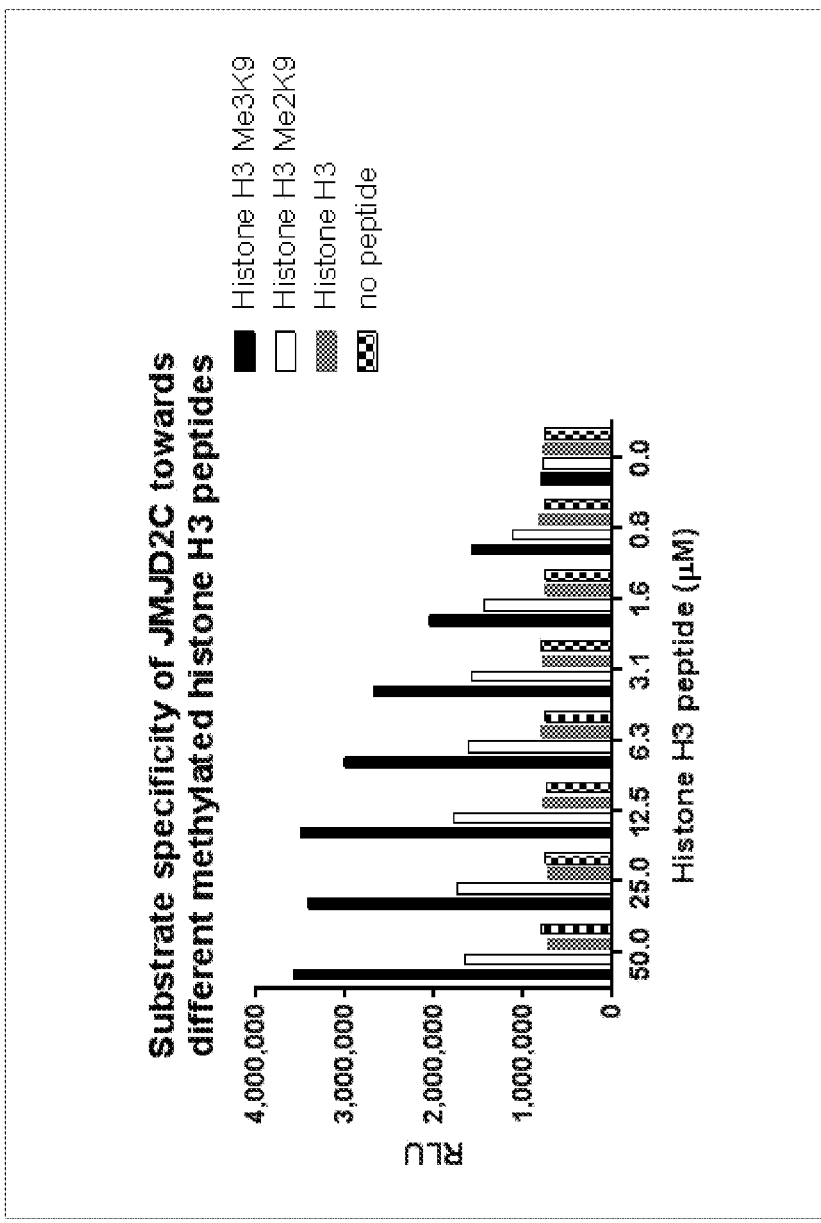
FIG. 5 illustrates the substrate specificity of JMJD2C towards different methylated and non-methylated histone H3 peptides.

In the method of the present invention, reactions with JMJC demethylase enzymes, including but not limited to JMJD2C (BPS Bioscience, cat #50105), were carried out at concentrations up to 50 µM of histone H3 peptide substrates Lys(Me3)9-histone H3 (1-21) (Anaspec, cat #64452), Lys(Me2)9-histone H3 (1-21) (Anaspec, cat #65401), and histone H3 (1-21) (Anaspec, cat #61701). The amount of luminescence generated was proportional to substrate concentration until saturation was reached and was proportional to the amount of enzyme within the linear range of the reaction. Succinate in the samples was converted to succinyl-CoA using a Bioluminescent Succinate Detection Reagent I. The succinyl-CoA generated was then converted to ATP, and the ATP was detected using the Bioluminescent Succinate Detection Reagent II. Briefly, 5 µL of JMJC demethylase in 50 mM HEPES, pH 7.5, 0.01% Tween-20, and 10 µg/mL BSA, was added to wells of a 96-well low volume plate. Titrations of histone H3 peptide substrates with different methylation states (amounts indicated in figures) were performed in a reaction buffer containing 50 mM HEPES, pH 7.5, 0.01% Tween-20, 10 µg/mL BSA, 200 µM ascorbate, 20 µM Fe(II), and 20 µM α-ketoglutarate. JMJC demethylase reactions were carried out in 10 µL for 60 min at room temperature. After incubation, 10 µL of the succinate to succinyl-CoA conversion reagent (Bioluminescent Succinate Detection Reagent I) was added, mixed for 2 min on an orbital shaker, and then incubated at room temperature for 60 min. To the samples, 20 µL of Bioluminescent Succinate Detection Reagent II was added, and the samples were again incubated at room temperature for 60 min. Luminescence was then detected on a luminometer (FIG. 5). The JMJC demethylase reaction and the succinate to succinyl-CoA conversion were performed in one step by mixing the JMJC demethylase, succinate, and the Bioluminescent Succinate Detection Reagent I in 10 µL reaction and incubating at room temperature for 60 min before adding the 10 µL of Bioluminescent Succinate Detection Reagent II. The reaction was performed by in 96-well low volume plates (Corning Costar®, cat#3693).

Figure 6:
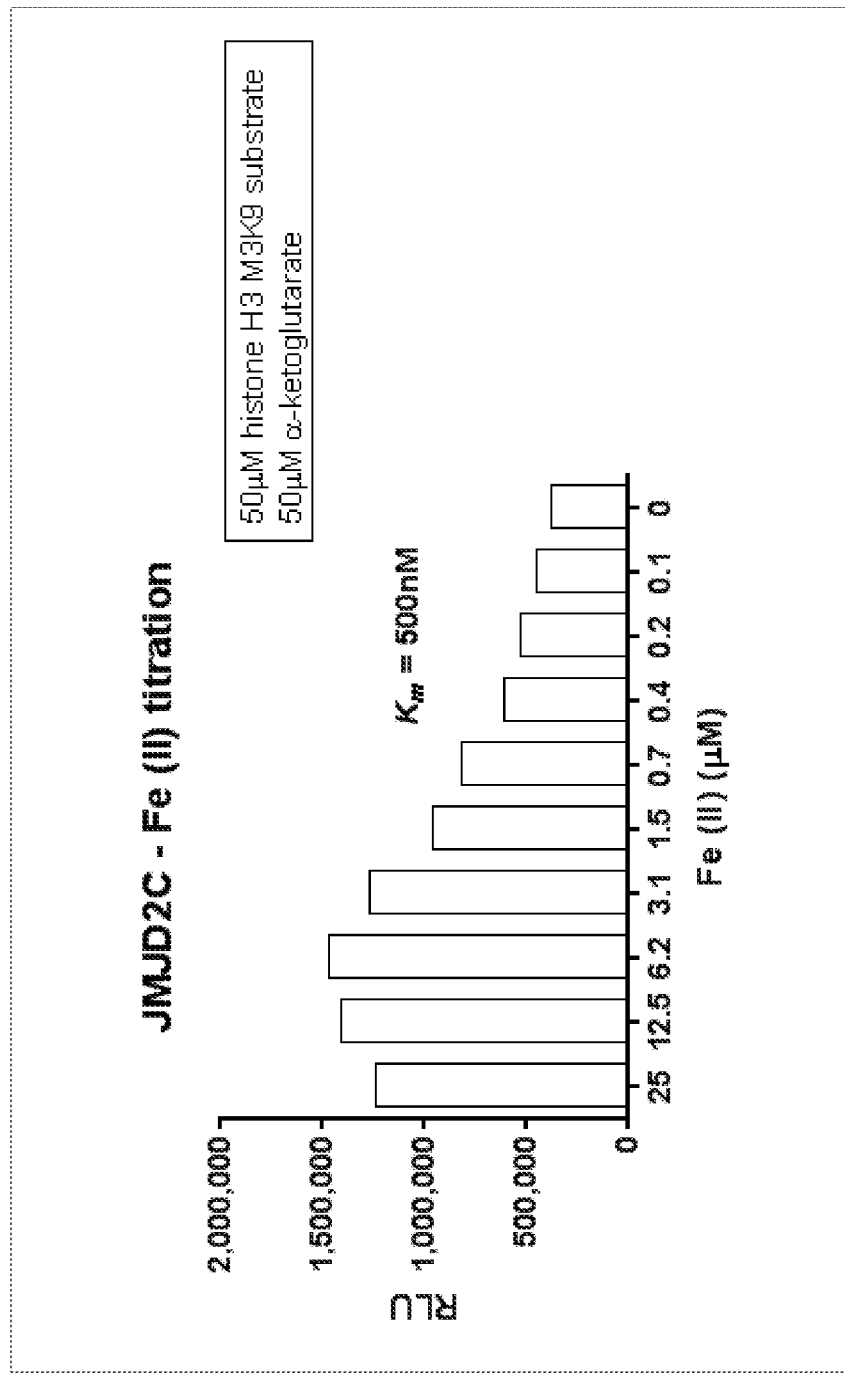
FIG. 6 illustrates the use of Method 1 to determine $Km_{app}$ of JMJD2C for Fe(II).

Reactions including titrations of different JMJC demethylase components were also performed as described above, and the apparent Km values obtained with the method of the present invention was similar to that reported in the literature (0.5-1.6 µM) (FIG. 6).

Example 6

Inhibition Experiments Using JMJC Demethylases

Figures 7A, 7B:
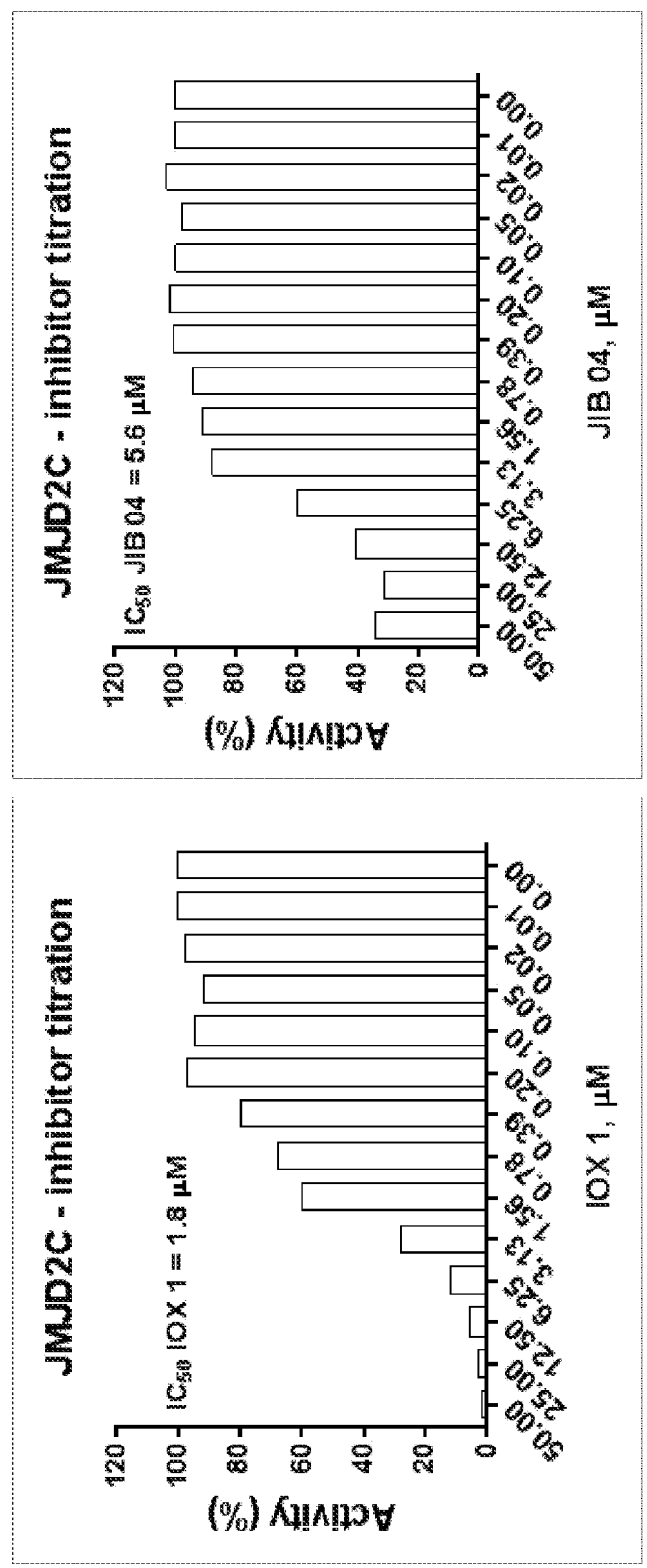
FIGS. 7A-7B illustrate dose response curves of demethylase inhibitors, IOX and JIB 04, for JMJD2C.

In the method of the present invention, reactions with JMJC demethylase enzymes, including but not limited to JMJD2C (BPS Bioscience, cat #50105), were carried out at concentrations up to 10 μM of Lys(Me3)9-histone H3 (1-21) peptide substrate (Anaspec, cat #64452). The amount of luminescence generated was proportional to substrate concentration until saturation was reached and was proportional to the amount of enzyme within the linear range of the reaction. Succinate in the samples was converted to succinyl-CoA using a Bioluminescent Succinate Detection Reagent I. The succinyl-CoA generated was then converted to ATP, and the ATP was detected using the Bioluminescent Succinate Detection Reagent II. Briefly, 5 μL of JMJC demethylase in 50 mM HEPES, pH 7.5, 0.01% Tween-20, and 10 μg/mL BSA was added to wells of a 96-well low volume plate. Titrations of JMJC demethylase inhibitors (amounts indicated on figures) were performed in a reaction buffer containing 50 mM HEPES, pH 7.5, 0.01% Tween-20, 10 μg/mL BSA, and 5% DMSO (v/v) and incubated for 10 min at room temperature. The reaction was initiated with the addition of 4 μL of 25 μM histone H3 Me3K9 peptide substrate diluted in a reaction buffer containing 50 mM HEPES, pH 7.5, 0.01% Tween-20, 10 μg/mL BSA, 250 μM ascorbate, 1.5 μM Fe(II), and 62.5 μM α-ketoglutarate. JMJC demethylase reactions were carried out in 10 μL for 60 min at room temperature. After incubation, 10 μL of the succinate to succinyl-CoA conversion reagent (Bioluminescent Succinate Detection Reagent I) was added, mixed for 2 min on an orbital shaker, and then incubated at room temperature for 60 min. To the samples, 20 μL of Bioluminescent Succinate Detection Reagent II was added, and the samples were again incubated at room temperature for 60 min. Luminescence was then detected on a luminometer (FIG. 7). The reaction was performed in wells of a 96-well low volume plates (Corning Costar®, cat#3693). The assay also showed very minimal false hits when screened against 1280 compounds of the LOPAC library, and it produced high Z' value confirming its robustness (data not shown).

Example 7

Figure 8:
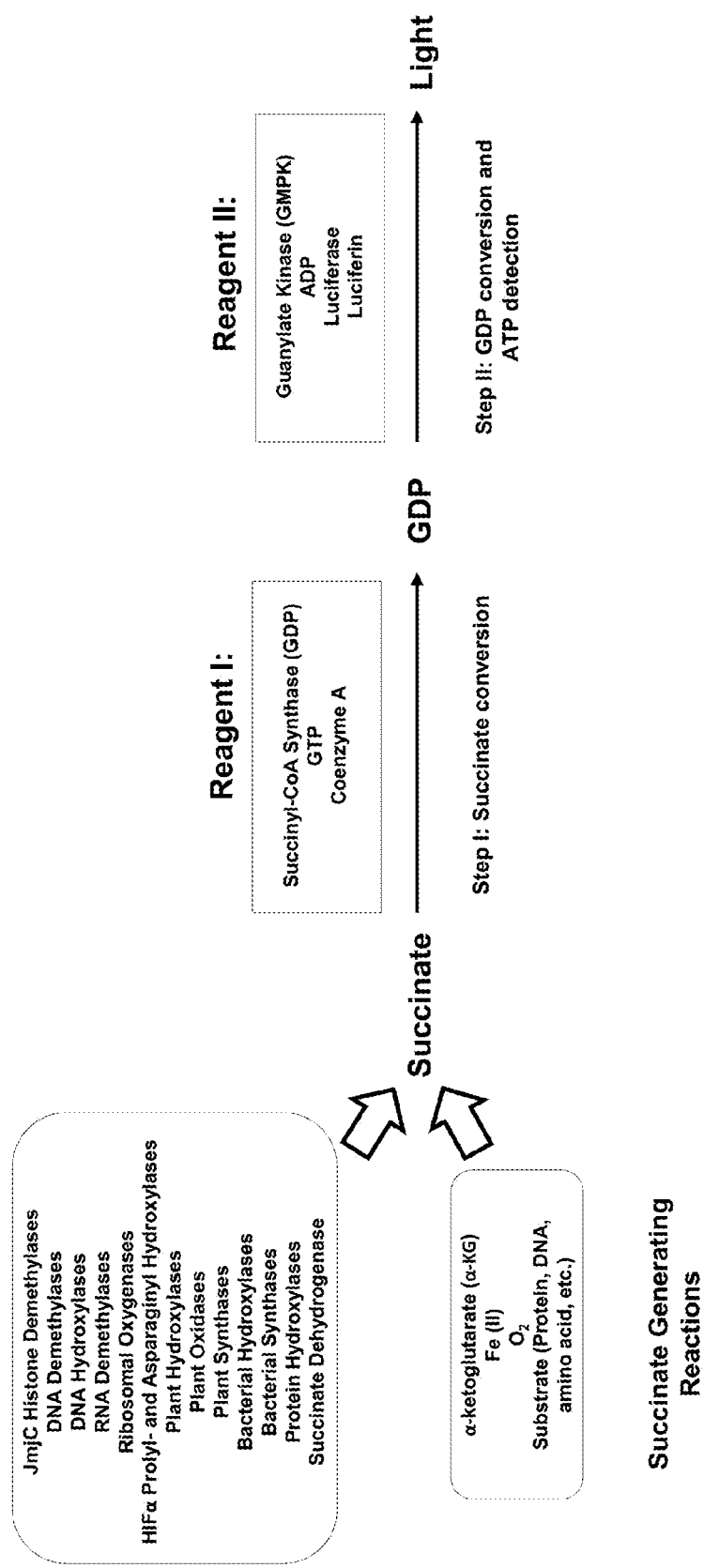
FIG. 8 illustrates a succinate detection assay using SCS (GDP forming)/Guanylate Kinase (Method 2).
Figure 9:
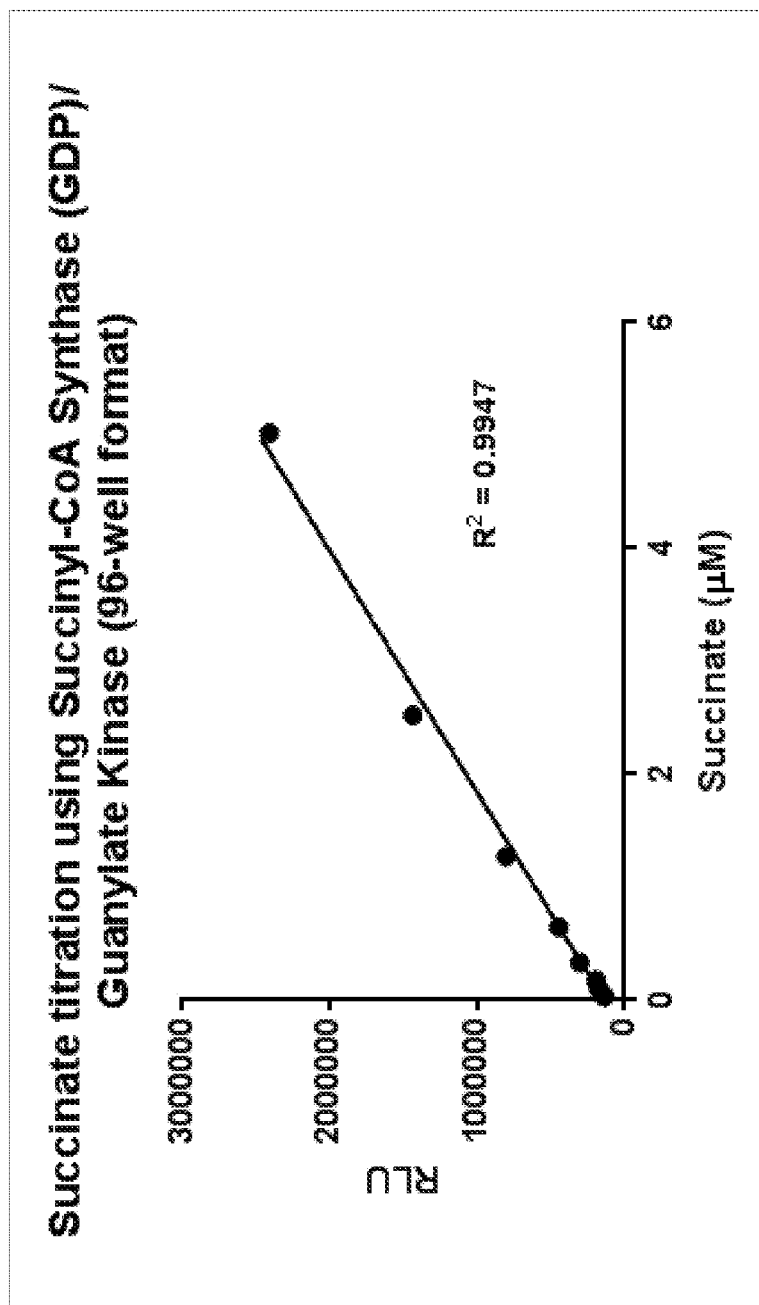
FIG. 9 illustrates succinate titration using Method 2.

Succinate Detection Assay Using GDP-Forming Succinyl-CoA Synthase and Guanylate Kinase The succinate detection assay described in FIG. 8 was performed generally in two steps as follows. The succinate titration was performed in 25 μL containing 50 mM Tris-HCl, pH 7.5, 10 mM $MgCl_2$, 15 μM coenzyme A, and 15 μM GTP. 25 μL of Bioluminescent Succinate Detection Reagent I (SCS-GDP/GMPK method) was added to the succinate samples, and the mixture was incubated for 60 min at room temperature. To detect succinyl-CoA, 50 μl of Bioluminescent Succinate Detection Reagent II (1.6 μL of Bioluminescent Succinate Detection Solution II (GMPK) in 1 mL of Kinase-Glo® reagent) was added, and the mixture was incubated for 60 min at room temperature before luminescence was detected on a luminometer. The succinate titration described in FIG. 9 was performed in wells of 96-well low volume plates (Corning Costar®, cat#3693).

Example 8

Figures 10A, 10B:
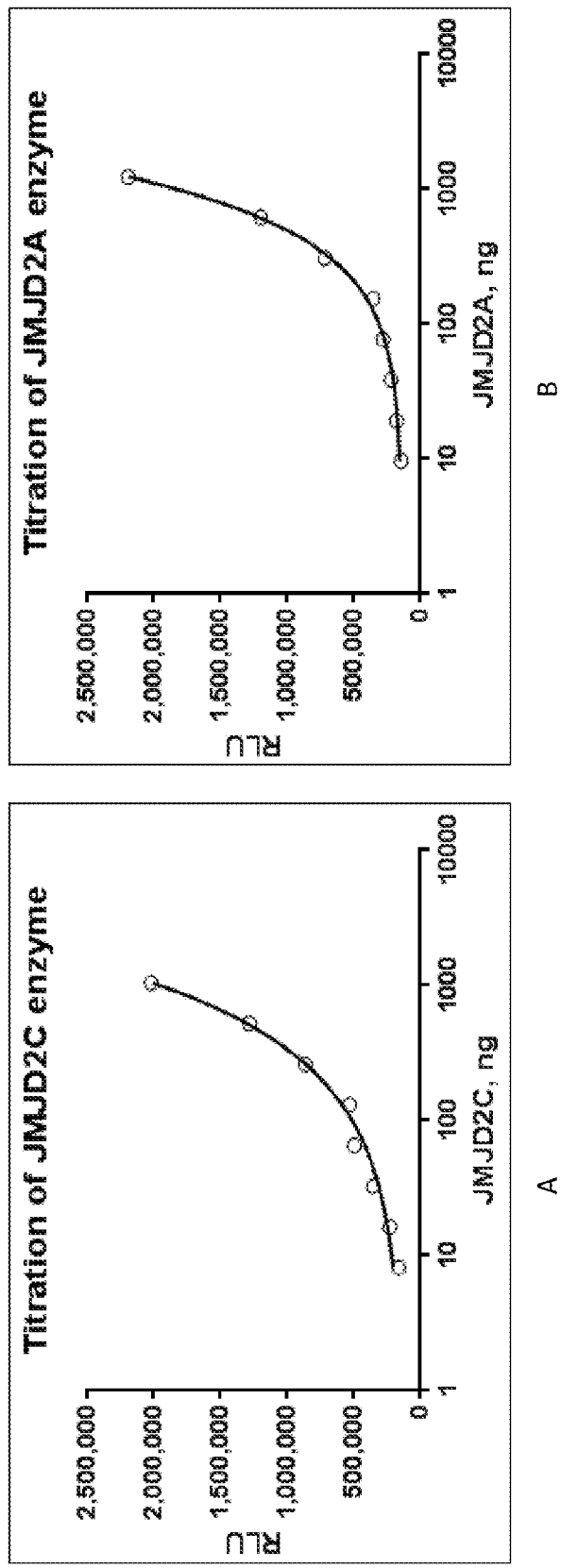
FIGS. 10A-10B illustrate JMJC demethylase titration curves for JMJD2C and JMJD2A enzymes.

Quantitation of the Different JMJC Demethylase Activities Using GDP-Forming Succinyl-CoA Synthase and Guanylate Kinase The method of the present invention was used to assay representative demethylating enzymes including, but not limited to, JMJD2C (BPS Bioscience, cat #50105) and JMJD2A (BPS Bioscience, cat #50123), and peptide Lys (Me3)9-histone H3 (1-21) (Anaspec, cat #64452) used as substrate. Each enzyme was titrated separately, and the reaction performed in Demethylase Reaction Buffer without Tween-20 and BSA (50 mM HEPES, pH 7.5, 100 μM ascorbate, 5 μM Fe(II), and 5 μM α-ketoglutarate). Succinate and GTP were converted to succinyl-CoA and GDP using Bioluminescent Succinate Detection Reagent I (SCS-GDP/GMPK method) followed by the conversion of GDP and ADP to ATP and GMP. ATP was detected using the Bioluminescent Succinate Detection Reagent II (SCS-GDP/GMPK method). Briefly, 6 μL of serially diluted JMJC demethylase in 50 mM HEPES, pH 7.5 was added to wells of a 96-well low volume plate. The JMJC demethylase reaction was started by adding 6 μL of a mixture containing Demethylase Reaction Buffer without Tween-20 and BSA, and 2.5 μM trimethylated histone H3 peptide substrate. After incubation of 60 min at room temperature, 12 μL of the succinate to succinyl-CoA conversion reagent (Bioluminescent Succinate Detection Reagent I (SCS-GDP/GMPK method)) was added, mixed for 2 min on an orbital shaker, and then incubated at room temperature for 60 min. To the samples, 24 μL of Bioluminescent Succinate Detection Reagent II (SCS-GDP/GMPK method) was added, and the samples were incubated at room temperature for 60 min. Luminescence was then detected on a luminometer (FIG. 10). It was found that succinate generated in the reaction was proportional to the demethylation and/or enzyme activity. Thus, the method of the present invention may be used to screen for compounds that alter the activity of the all enzymes involved in histone demethylation.

Example 9

Figure 11:
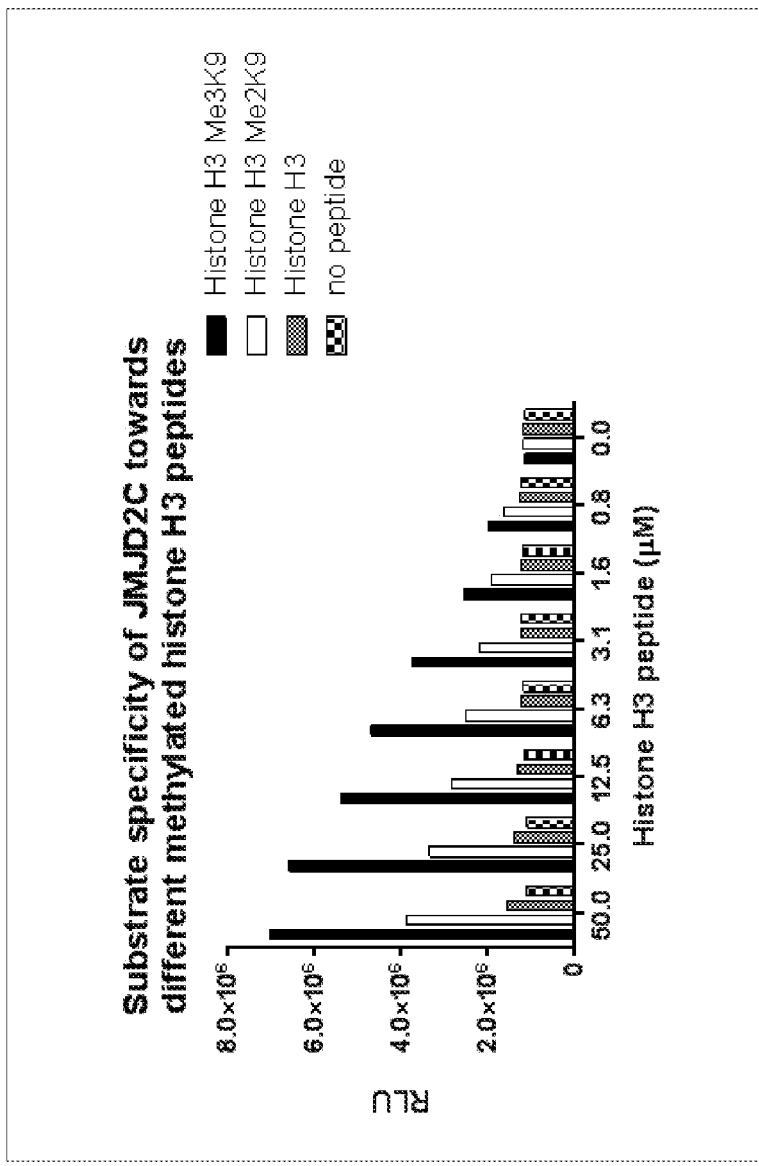
FIG. 11 illustrates substrate specificity of JMJD2C towards different methylated histone H3 peptides using Method 2.

Determination of Substrate Specificity of JMJC Demethylases Using GDP-Forming Succinyl-CoA Synthase and Guanylate Kinase In the method of the present invention, reactions with JMJC demethylase enzymes, including, but not limited to JMJD2C (BPS Bioscience, cat #50105), were carried out at concentrations up to 50 μM of histone H3 peptide substrates Lys(Me3)9-histone H3 (1-21) (Anaspec, cat #64452), Lys (Me2)9-histone H3 (1-21) (Anaspec, cat #65401), and histone H3 (1-21) (Anaspec, cat #61701), and the amount of luminescence generated was proportional to substrate concentration until saturation was reached and was proportional to the amount of enzyme within the linear range of the reaction. Succinate in the samples was converted to succinyl-CoA and GDP using a Bioluminescent Succinate Detection Reagent I (SCS-GDP/GMPK method). The GDP generated was then converted to ATP and GMP, and the ATP detected using the Bioluminescent Succinate Detection Reagent II (SCS-GDP/GMPK method). Briefly, 12 μL of JMJC demethylase in 50 mM HEPES, pH 7.5, was added to wells of a 96-well low volume plate. Titrations of histone H3 peptide substrates with different methylation states (amounts indicated on figures) were performed in a reaction buffer containing Demethylase Reaction Buffer without Tween-20 and BSA (50 mM HEPES, pH 7.5, 200 μM ascorbate, 20 μM Fe(II), and 20 μM α-ketoglutarate). JMJC demethylase reactions were carried out in 24 μL for 60 min at room temperature. After incubation, 24 μL of the succinate to succinyl-CoA conversion reagent (Bioluminescent Succinate Detection Reagent I (SCS-GDP/GMPK method)) was added, mixed for 2 min on an orbital shaker, and then incubated at room temperature for 60 min. To the samples, 48 μL of Bioluminescent Succinate Detection Reagent II (SCS-GDP/GMPK method) was added, and the samples again incubated at room temperature for 60 min. Luminescence was then detected on a luminometer (FIG. 11). The reaction was performed in wells of a 96-well low volume plates (Corning Costar®, cat#3693).

Example 10

Figure 12:
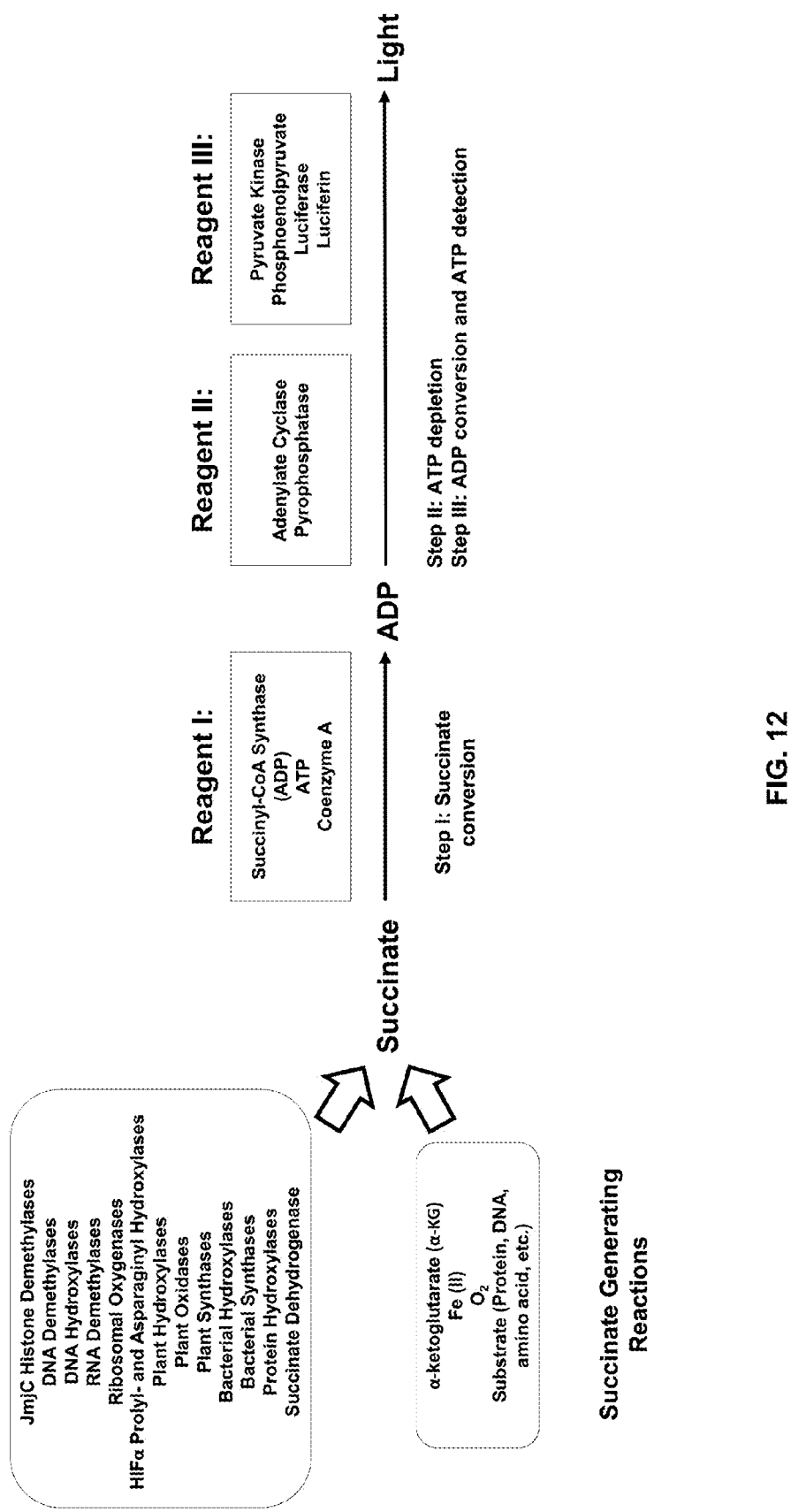
FIG. 12 illustrates a succinate detection assay using SCS (ADP forming)/ADP detection reagents (Method 3).
Figure 13:
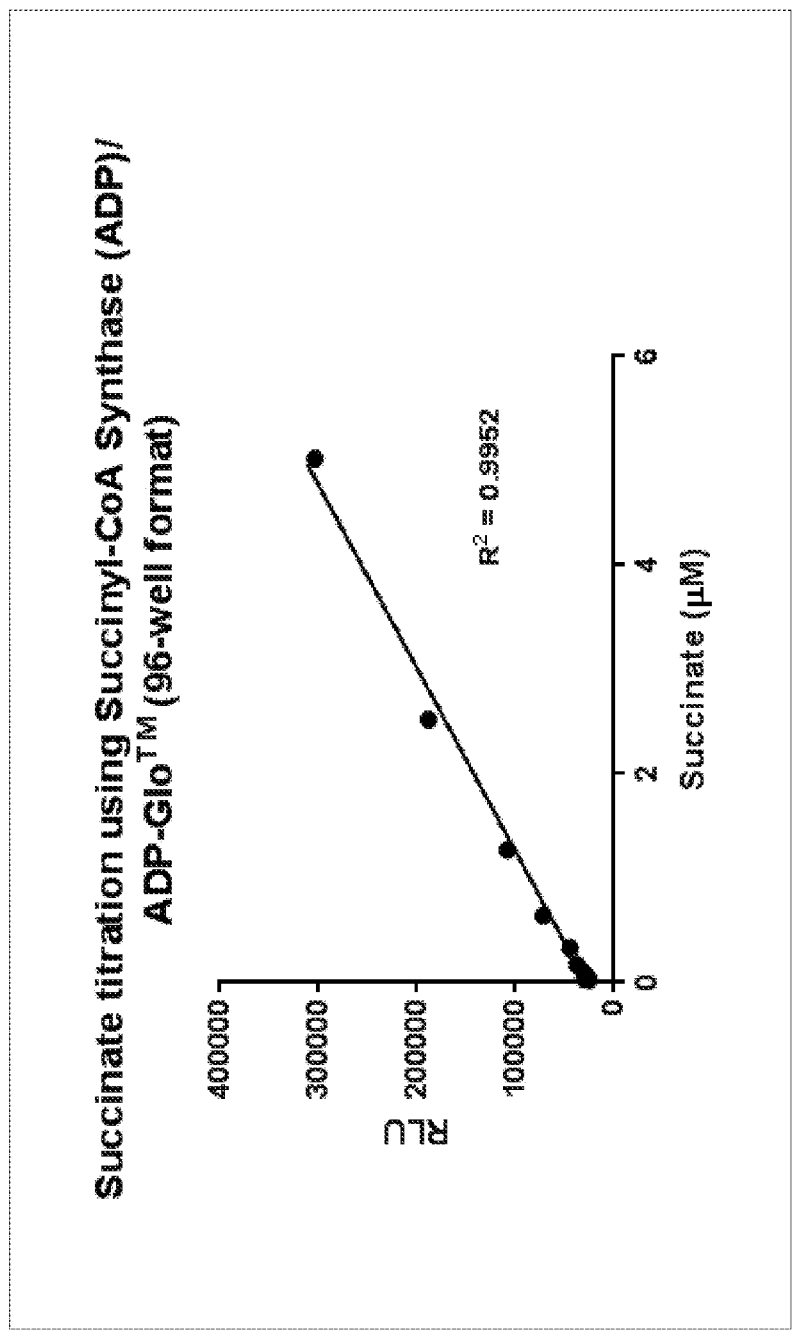
FIG. 13 illustrates succinate titration using SCS (ADP forming)/ADP-Glo™ assay (Method 3).

Succinate Detection Assay Using ADP-Forming Succinyl-CoA Synthase, Adenylate Cyclase, Pyrophosphatase and Pyruvate Kinase The succinate detection assay described in FIG. 12 was performed generally in three steps as follows herein. The succinate titration was performed in 10 µL containing 50 mM Tris-HCl, pH 7.5. 10 µL of Bioluminescent Succinate Detection Reagent I (SCS-ADP/ADP-Glo™ method, containing 50 mM Tris-HCl, pH 7.5, 10 mM $MgCl_2$, 30 µM ATP, and 30 µM coenzyme A) was added to the succinate samples, and the mixture was incubated for 60 min at room temperature. To remove the remaining ATP, 20 µL of ADP-Glo™ Reagent was added to the succinate samples, and the mixture was incubated for 40 min at room temperature. To detect ADP, 40 µL of ADP-Glo™ Kinase Detection Reagent (Promega) was added, and the mixture was incubated for 30 min at room temperature before luminescence was detected on a luminometer. The succinate titration described in FIG. 13 was performed in wells of 96-well low volume plates.

Example 11

Figures 14A, 14B:
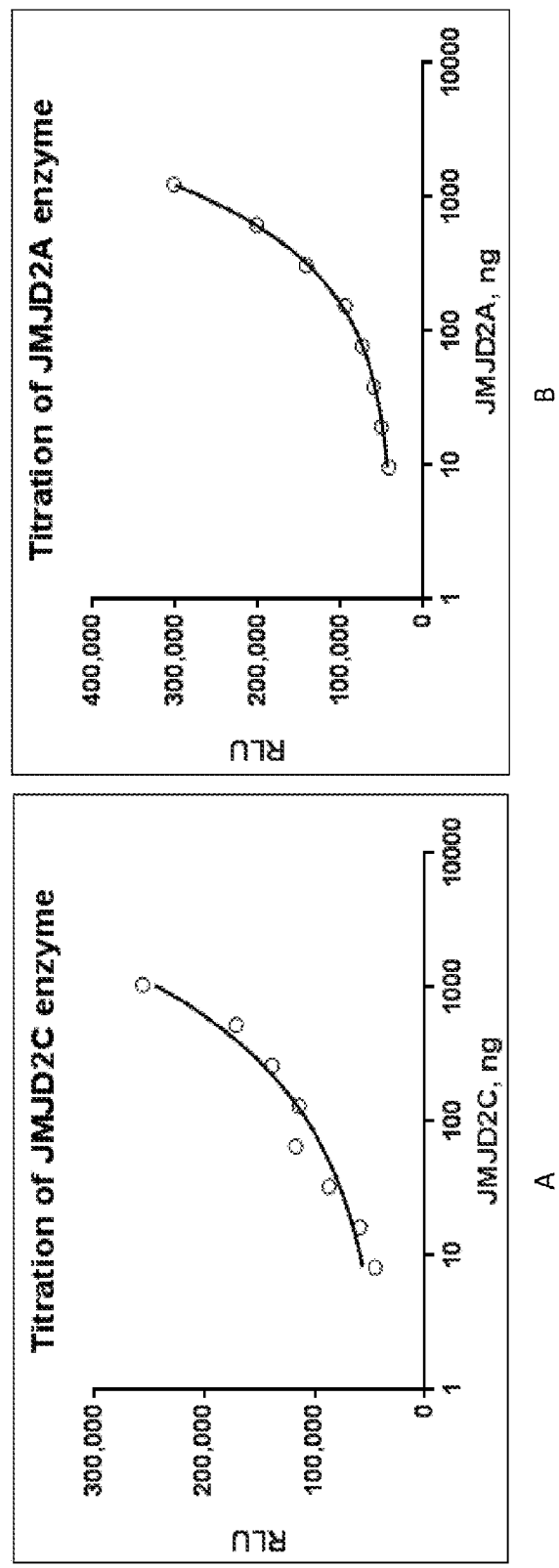
FIGS. 14A-14B illustrate succinate titration curves for JMJD2C and JMJD2A enzymes using Method 3.

Quantitation of the Different JMJC Demethylase Activities Using ADP-Forming Succinyl-CoA Synthase, Adenylate Cyclase, Pyrophosphatase and Pyruvate Kinase The method of the present invention was used to assay representative demethylating enzymes including, but not limited to JMJD2C (BPS Bioscience, cat #50105) and JMJD2A (BPS Bioscience, cat #50123), and peptide Lys (Me3)9-histone H3 (1-21) (Anaspec, cat #64452) used as substrate. Each enzyme was titrated separately and together, and the reaction performed in Demethylase Reaction Buffer without Tween-20 and BSA (50 mM HEPES, pH 7.5, 100 µM ascorbate, 5 µM Fe(II), and 5 µM α-ketoglutarate). Succinate and ATP were converted to succinyl-CoA and ADP using Bioluminescent Succinate Detection Reagent I (SCS-ADP/ADP-Glo™ method). ADP-Glo™ Reagent was added to the wells of a 96-well low volume plate to remove any remaining ATP from the reaction, followed by the conversion of ADP to ATP and detection of ATP using the ADP-Glo™ Kinase Detection Reagent. Briefly, 6 µL of serially diluted JMJC demethylase in 50 mM HEPES, pH 7.5 was added to wells of a 96-well low volume plate. The JMJC demethylase reaction was started by adding 6 µL of a mixture containing Demethylase Reaction Buffer without Tween-20 and BSA and 2.5 µM trimethylated histone H3 peptide substrate. After incubation of 60 min at room temperature, 12 µL of the succinate to succinyl-CoA conversion reagent (Bioluminescent Succinate Detection Reagent I (SCS-ADP/ADP-Glo™ method)) was added, mixed for 2 min on an orbital shaker, and then incubated at room temperature for 60 min. To the samples, 24 µL of ADP-Glo™ Reagent was added, and the samples incubated at room temperature for 40 min. For the conversion of ADP to ATP, 48 µL of ADP-Glo™ Kinase Detection Reagent was added, and the samples were incubated at room temperature for 30 min. Luminescence was then detected on a luminometer (FIG. 14). It was found that succinate generated in the reaction was proportional to the demethylation and/or enzyme activity. Thus, the method of the present invention may be used to screen for compounds that alter the activity of the all enzymes involved in histone demethylation.

Example 12

Succinate Determination in Cellular and Tissue Extracts

The method of the present invention was used to determine the presence and/or amount of succinate in tissue extracts. Any ATP present in the sample was removed. After removal of any ATP present in the sample, the succinate was converted to succinyl-CoA by SCOT, the ADP was converted to ATP, and the ATP was detected using the Bioluminescent Succinate Detection Reagent II (ADP-to-ATP Conversion Reagent). The ATP depleted samples that were tested for conversion of succinate (containing SCOT and SCS) were compared to samples which contained only Luciferase/luciferin to assess the succinate presence.

Figure 15:
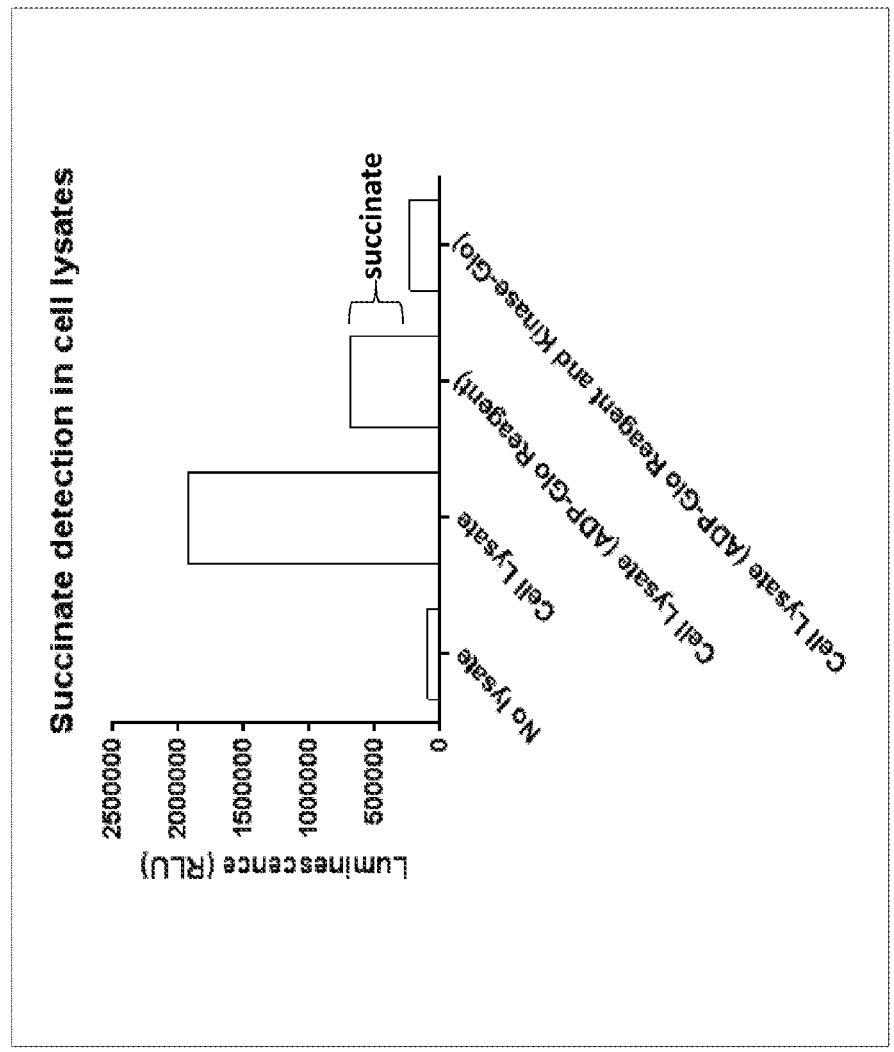
FIG. 15 illustrates succinate detection in cell extracts using 3-oxoacid CoA-transferase/Succinyl-CoA Ligase (Method 1).

Any ATP present in the sample is removed using the ADP-Glo™ Reagent (Promega Corp), succinate was converted using Bioluminescent Succinate Detection Reagent I followed by the conversion of ADP to ATP. ATP was detected using the Bioluminescent Succinate Detection Reagent II. Briefly, 10 µL of ATP-depleted cell extract in 50 mM Potassium Phosphate, pH 7.5, 10 mM $MgCl_2$ was incubated with 10 µL of the succinate to succinyl-CoA conversion reagent (Bioluminescent Succinate Detection Reagent I), mixed for 2 min on an orbital shaker, and then incubated at room temperature for 60 min. To the samples, 20 µL of Bioluminescent Succinate Detection Reagent II was added, and the samples were incubated at room temperature for 60 min. Luminescence was then detected on a luminometer (FIG. 15).

Example 13

Figure 16:
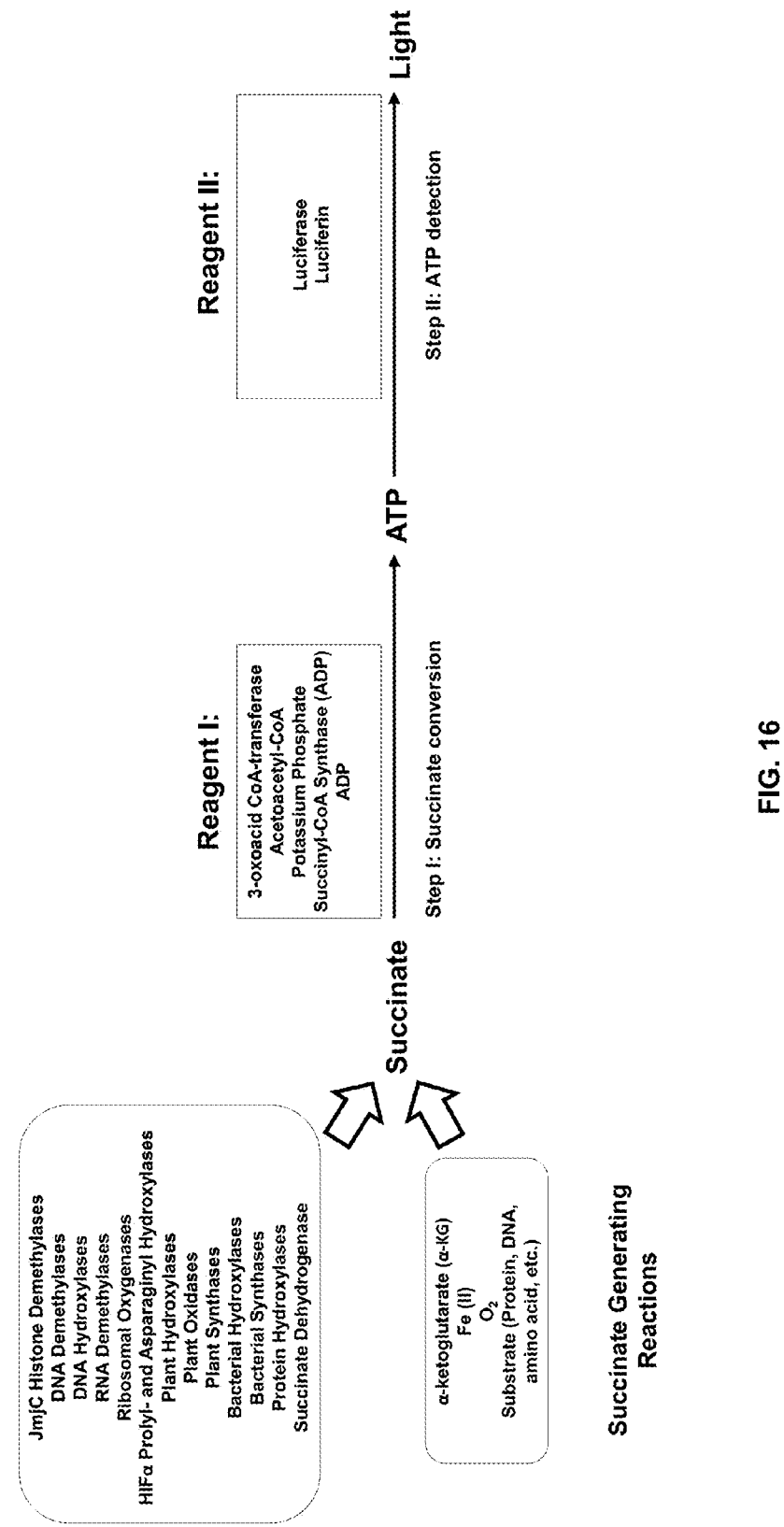
FIG. 16 illustrates a succinate detection assay using modified 3-oxoacid CoA-transferase/Succinyl-CoA Ligase (Method 4) after a succinate producing enzymatic reaction.
Figure 17:
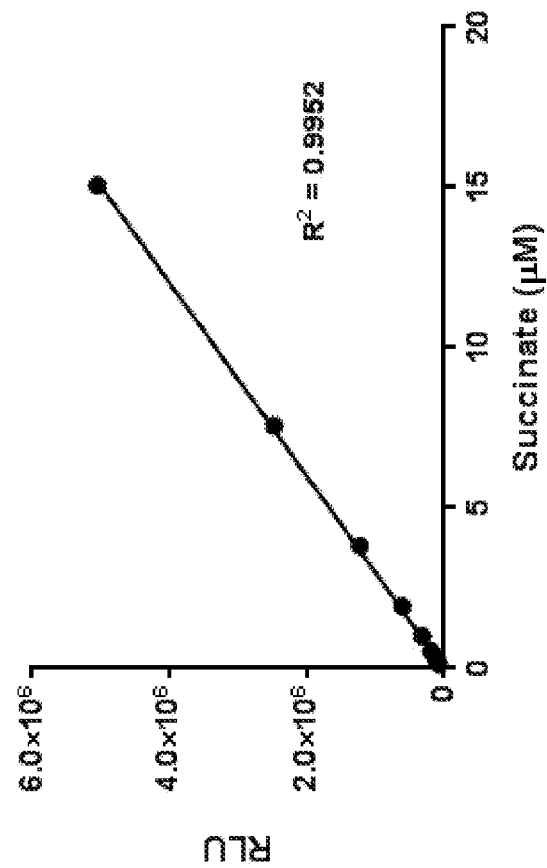
FIG. 17 illustrates succinate titration using modified 3-oxoacid CoA-transferase/Succinyl-CoA Ligase (Method 4).

Succinate Detection Assay Using Modified 3-Oxoacid CoA Transferase and ADP-Forming Succinyl-CoA Synthase The succinate detection assay described in FIG. 16 was performed generally in two steps as follows. The succinate titration was performed in 25 µL containing 1× Demethylase Reaction Buffer (50 mM HEPES, pH 7.5, 100 µM ascorbate, 10 µM Fe(II), 10 µM α-ketoglutarate). 25 µL of Bioluminescent Succinate Detection Reagent I was added to the succinate samples, and the mixture was incubated for 60 min at room temperature (~23° C.). To detect ATP, 50 µL of Bioluminescent Succinate Detection Reagent II was added, and the mixture was incubated for 10 min at room temperature before luminescence was detected on a luminometer. The succinate titration shown in FIG. 17 was performed in 96-well low volume plates (Corning Costar®, cat#3693).

Example 14

Figures 18A, 18B:
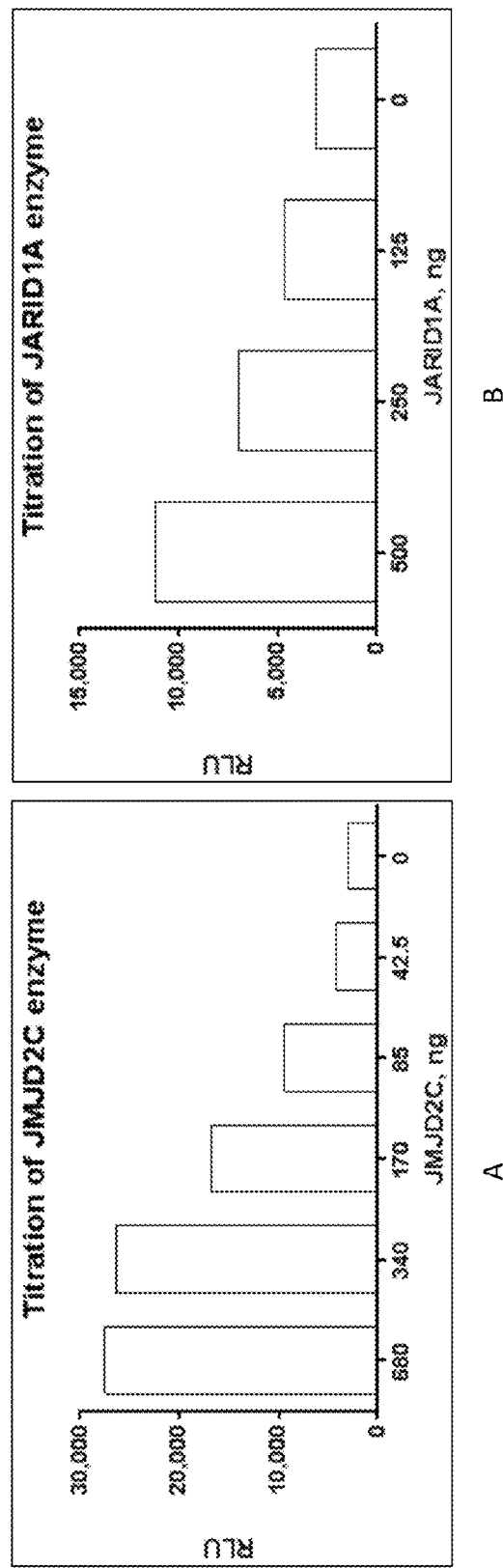
FIGS. 18A-18B illustrate JMJC demethylase titration curves for JMJD2C and JARID1A enzymes (Method 4).

Quantitation of the Different JumonjiC Demethylase Activities Using Modified 3-Oxoacid CoA Transferase and ADP-Forming Succinyl-CoA Synthase The method of the present invention was used to assay representative demethylating enzymes including, but not limited to, JMJD2C (BPS Bioscience, cat #50105) with substrate Lys(Me3)9-histone H3 (1-21) (Anaspec, cat #64452) and JARID1A (BPS Bioscience, cat #50110) with substrate Lys(Me3)4-histone H3 (1-21) (Anaspec, cat #64194). Each enzyme was titrated separately, and the reaction was performed in the Demethylase Reaction Buffer. Succinate was converted to ATP using Bioluminescent Succinate Detection Reagent I followed by the detection of ATP using the Bioluminescent Succinate Detection Reagent II. Briefly, 5 µL of serially diluted JMJC demethylase in 50 mM HEPES, pH 7.5 was added to wells of a 96-well low volume plate. The JMJC demethylase reaction was started by adding 5 µL of a mixture containing 2× Demethylase Reaction Buffer and 20 µM trimethylated histone H3 peptide substrate. After incubation of 60 min at room temperature, 10 µL of the succinate to ATP conversion reagent (Bioluminescent Succinate Detection Reagent I) was added, mixed for 2 min on an orbital shaker, and then incubated at room temperature for 60 min. To the samples, 20 µL of Bioluminescent Succinate Detection Reagent II was added, and the samples were incubated at room temperature for 10 min. Luminescence was then detected on a luminometer (FIG. 18). It was found that succinate generated in the reaction was proportional to the demethylation and/or enzyme activity. Thus, the method of the present invention may be used to screen for compounds that alter the activity of all enzymes involved in histone demethylation.

Example 15

Figures 19A, 19B:
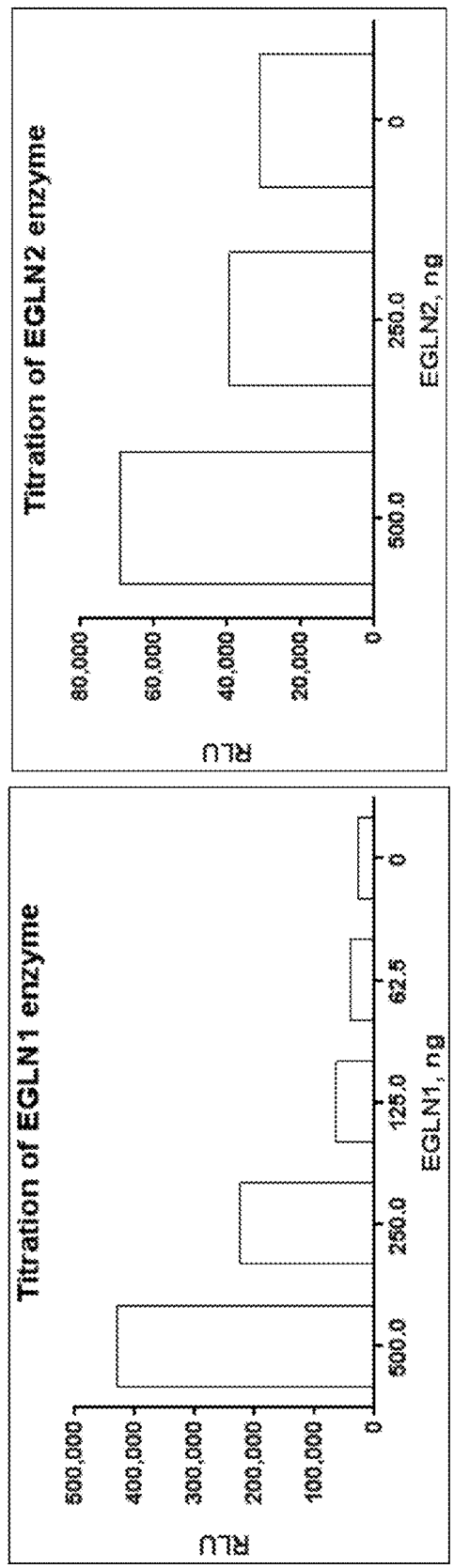
FIGS. 19A-19B illustrate dioxygenase titration curves for EGLN1 and EGLN2 enzymes (Method 4).

Quantitation of the Different Dioxygenase Activities Using Modified 3-Oxoacid CoA Transferase and ADP-Forming Succinyl-CoA Synthase The method of the present invention was used to assay representative hydroxylating enzymes including, but not limited to, ELGN1 (OriGene Technologies, cat # TP315158) and EGLN2 (OriGene Technologies, cat # TP306152) with substrate HIF-1 α (556-574) (Anaspec, cat # AS-61528). Each enzyme was titrated separately, and the reaction was performed in 1× Reaction Buffer (50 mM HEPES, pH 7.5, 100 µM ascorbate, 10 µM Fe(II), 10 µM α-ketoglutarate). Succinate was converted to ATP using Bioluminescent Succinate Detection Reagent I followed by the detection of ATP using the Bioluminescent Succinate Detection Reagent II. Briefly, 5 µL of serially diluted prolyl hydroxylase (in 50 mM HEPES, pH 7.5) was added to wells of a 96-well low volume plate. The prolyl hydroxylase reaction was started by adding 5 µL of a mixture containing 2× Reaction Buffer and 20 µM HIF-1 α (556-574) peptide substrate. After incubation of 60 min at room temperature, 10 µL of the succinate to ATP conversion reagent (Bioluminescent Succinate Detection Reagent I) was added, mixed for 2 min on an orbital shaker, and then incubated at room temperature for 60 min. To the samples, 20 µL of Bioluminescent Succinate Detection Reagent II was added, and the samples were incubated at room temperature for 10 min. Luminescence was then detected on a luminometer (FIG. 19). It was found that succinate generated in the reaction was proportional to the hydroxylase and/or enzyme activity. Thus, the method of the present invention may be used to screen for compounds that alter the activity of all enzymes involved in HIF1-alpha hydroxylation.

While the present invention is described in connection with what is presently considered to be the most practical and preferred embodiments, it should be appreciated that the invention is not limited to the disclosed embodiments and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

For reasons of completeness, various aspects of the present disclosure are set out in the following numbered clauses:

Clause 1. A method for luminescent detection or determination of succinate in a sample, the method comprising:
(a) contacting the sample with a first detection reagent to form a first reaction mixture;
(b) contacting the first reaction mixture with a second detection reagent to form a second reaction mixture; and
(c) detecting luminescence in the second reaction mixture, thereby detecting or determining the presence or amount of succinate in the sample;
wherein if succinate is present in the sample, the first detection reagent and the second detection reagent converts the succinate to ATP.

Clause 2. A method for detecting or determining the presence or amount of succinate in a sample, the method comprising:
(a) contacting the sample with a first detection reagent to form a first reaction mixture;
(b) contacting the first reaction mixture with a second detection reagent to form a second reaction mixture; and
(c) detecting luminescence in the second reaction mixture, thereby detecting or determining the presence or amount of succinate in the sample;
wherein:
(i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;
(ii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or
(iii) the first detection reagent comprises ADP forming succinyl-CoA ligase (SCS-ADP), ATP, and coenzyme A and the second detection reagent comprises an ATP depletion reagent and subsequently an ADP to ATP conversion/detection reagent, wherein the first reaction mixture is contacted sequentially with the ATP depletion reagent and the ADP to ATP conversion/detection reagent, and wherein the ATP depletion reagent comprises adenylate cyclase and pyrophosphatase and the ADP to ATP conversion/detection reagent comprises pyruvate kinase, phosphoenolpyruvate, a bioluminescent enzyme, and a luciferin substrate.

Clause 3. The method of clause 2, wherein the first detection reagent comprises 3-oxoacid CoA-transferase (SCOT), inorganic phosphate, and acetoacetyl-CoA and the second detection reagent comprises succinyl-CoA ligase (SCS), ADP, a thermostable firefly luciferase, and D-luciferin.

Clause 4. The method of clause 2, wherein the first detection reagent comprises GDP forming succinyl-CoA ligase (SCS-GDP), GTP, and coenzyme A and the second detection reagent comprises guanylate kinase (GMPK), ADP, a thermostable firefly luciferase, and D-luciferin.

Clause 5. The method of clause 2, wherein the first detection reagent comprises ADP forming succinyl-CoA ligase (SCS-ADP), ATP, and coenzyme A and the second detection reagent comprises an ATP depletion reagent and subsequently an ADP to ATP conversion/detection reagent, wherein the first reaction mixture is contacted sequentially with the ATP depletion reagent and the ADP to ATP conversion/detection reagent, and wherein the ATP depletion reagent comprises adenylate cyclase and pyrophosphatase and the ADP to ATP conversion/detection reagent comprises pyruvate kinase, phosphoenolpyruvate, a thermostable firefly luciferase, and D-luciferin.

Clause 6. A method for detecting or determining the presence or amount of a succinate forming enzyme in a sample or the activity of a succinate forming enzyme, the method comprising:

(a) contacting the sample with a peptide, protein, or non-protein substrate, 2-oxoglutarate, Fe (II), and ascorbate to form a succinate reaction mixture, wherein succinate is formed if the sample comprises a succinate forming enzyme;

(b) contacting the succinate reaction mixture with a first detection reagent to form a first reaction mixture, wherein the succinate formed in step (a) is converted to succinyl-CoA;

(c) contacting the first reaction mixture with a second detection reagent to form a second reaction mixture; and (d) detecting luminescence in the second reaction mixture, thereby detecting or determining the presence or amount of succinate forming enzyme or succinate forming enzyme activity in the sample, wherein:

(i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;

(ii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iii) the first detection reagent comprises ADP forming succinyl-CoA ligase (SCS-ADP), ATP, and coenzyme A and the second detection reagent comprises an ATP depletion reagent and an ADP to ATP conversion/detection reagent, wherein the first reaction mixture is contacted sequentially with the ATP depletion reagent and the ADP to ATP conversion/detection reagent, wherein the ATP depletion reagent comprises adenylate cyclase and pyrophosphatase, and wherein the ADP to ATP conversion/detection reagent comprises pyruvate kinase, phosphoenolpyruvate, a bioluminescent enzyme, and a luciferin substrate.

Clause 7. The method of any one of clauses 1-6, wherein contacting the first reaction mixture with a second detection reagent generates ATP.

Clause 8. The method of clause 6, wherein the succinate forming enzyme is a 2-oxoglutarate oxygenase.

Clause 9. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe (II), and ascorbate to form a succinate reaction mixture;

(c) contacting the succinate reaction mixture with 3-oxoacid CoA-transferase (SCOT), inorganic phosphate, and acetoacetyl-CoA to form a first reaction mixture, whereby the succinate formed in step (a) is converted to succinyl-CoA;

(d) contacting the first reaction mixture with an ATP detection reagent to form a second reaction mixture, wherein the ATP detection reagent comprises succinyl-CoA ligase (SCS), ADP, a bioluminescent enzyme, and a luciferin substrate;

(e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

Clause 10. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe (II), and ascorbate to form a succinate reaction mixture;

(c) contacting the succinate reaction mixture with GDP forming succinyl-CoA ligase (SCS-GDP), GTP, and coenzyme A; to form a first reaction mixture, whereby the succinate formed in step (a) is converted to succinyl-CoA and GDP;

(d) contacting the first reaction mixture with an ATP detection reagent to form a second reaction mixture, wherein the ATP detection reagent comprises guanylate kinase (GMPK), ADP, a bioluminescent enzyme, and a luciferin substrate;

(e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

Clause 11. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe (II), and ascorbate to form a succinate reaction mixture;

(c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP;

(d) contacting the first reaction mixture with an ATP depletion reagent to form a second reaction mixture, wherein the ATP depletion reagent comprises adenylate cyclase and pyrophosphatase;

(e) contacting the second reaction mixture with an ADP to ATP conversion/detection reagent to form a third reaction mixture, wherein the ADP to ATP conversion/detection reagent comprises pyruvate kinase, phosphoenolpyruvate, a bioluminescent enzyme, and a luciferin substrate;

(f) detecting luminescence in the third reaction mixture; and (g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity.

Clause 12. The method of any one of clauses 8-11, wherein the 2-oxoglutarate oxygenase is a Fe (II) dependent lysine demethylase or a 2-oxoglutarate-dependent dioxygenase.

Clause 13. The method of clause 12, wherein the Fe (II) dependent lysine demethylases is a JumonjiC domain-containing histone lysine (JMJC) demethylase.

Clause 14. The method of clause 13, wherein the JMJC demethylase is a member of the KDM3, KDM4, KDM5, or KDM6 family of histone demethylases.

Clause 15. The method of clause 14, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 16. The method of clause 15, wherein the JMJC demethylase is JMJD2A or JMJD2C.

Clause 17. The method of any one of clauses 6-16, wherein the sample is contacted with a peptide, protein, or non-protein substrate.

Clause 18. The method of clause 17, wherein the peptide or protein substrate is a histone peptide substrate.

Clause 19. The method of clause 18, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 20. The method of any one of the preceding clauses, wherein the bioluminescent enzyme is luciferase.

Clause 21. The method of clause 20, wherein the luciferase is a recombinant luciferase.

Clause 22. The method of clause 20, wherein the luciferase is a thermostable and/or a chemostable luciferase.

Clause 23. The method of clause 22, wherein the luciferase is a thermostable firefly luciferase.

Clause 24. A kit for detecting succinate in a sample, the kit comprising:
(i) 3-oxoacid CoA-transfer (SCOT);
(ii) inorganic phosphate;
(iii) acetoacetyl-CoA;
(iv) succinyl-CoA ligase (SCS);
(v) ADP;
(vi) a bioluminescent enzyme; and
(vii) a luciferin substrate,
wherein (i)-(vii) are in one or more containers.

Clause 25. The kit of clause 24, wherein a first detection reagent comprises:
(i) 3-oxoacid CoA-transfer (SCOT);
(ii) inorganic phosphate; and
(iii) acetoacetyl-CoA; and
a second detection reagent comprises:
(iv) succinyl-CoA ligase (SCS);
(v) ADP;
(vi) a bioluminescent enzyme; and
(vii) a luciferin substrate.

Clause 26. The kit of clause 24 or 25, wherein the bioluminescent enzyme is a thermostable firefly luciferase and the luciferin substrate is D-luciferin.

Clause 27. A kit for detecting succinate in a sample, the kit comprising:
(i) GDP forming succinyl-CoA ligase (SCS-GDP);
(ii) GTP;
(iii) coenzyme A;
(iv) guanylate kinase (GMPK);
(v) ADP;
(vi) a bioluminescent enzyme; and
(vii) a luciferin substrate,
wherein (i)-(vii) are in one or more containers.

Clause 28. The kit of clause 27, wherein a first detection reagent comprises:
(i) GDP forming succinyl-CoA ligase (SCS-GDP);
(ii) GTP; and
(iii) coenzyme A; and
a second detection reagent comprises:
(iv) guanylate kinase (GMPK);
(v) ADP;
(vi) a bioluminescent enzyme; and
(vii) a luciferin substrate.

Clause 29. A kit for detecting succinate in a sample, the kit comprising:
(i) ADP forming succinyl-CoA ligase (SCS-ADP);
(ii) ATP;
(iii) coenzyme A;
(iv) adenylate cyclase;
(v) pyrophosphatase;
(vi) pyruvate kinase;
(vii) phosphoenolpyruvate;
(viii) a bioluminescent enzyme; and
(ix) a luciferin substrate,
wherein (i)-(ix) are in one or more containers.

Clause 30. The kit of clause 29, wherein a first detection reagent comprises:
(i) ADP forming succinyl-CoA ligase (SCS-ADP);
(ii) ATP; and
(iii) coenzyme A; and
a second detection reagent comprises an ATP depletion reagent and an ADP to ATP conversion/detection reagent, wherein the ATP depletion reagent comprises:
(iv) adenylate cyclase; and
(v) pyrophosphatase; and
the ADP to ATP conversion/detection reagent comprises:
(vi) pyruvate kinase;
(vii) phosphoenolpyruvate;
(viii) a bioluminescent enzyme; and
(ix) a luciferin substrate.

Clause 31. The kit of any one of clauses 24-30, further comprising instructions for using the kit to detect or determine the presence or amount of succinate in the sample.

Clause 32. A kit for detecting or determining 2-oxoglutarate oxygenase activity in a sample, the kit comprising:
(i) a peptide, protein, or non-protein substrate;
(ii) 2-oxoglutarate;
(iii) Fe (II);
(iv) ascorbate;
(v) 3-oxoacid CoA-transfer (SCOT);
(vi) inorganic phosphate;
(vii) acetoacetyl-CoA;
(viii) succinyl-CoA ligase (SCS);
(ix) ADP;
(x) a bioluminescent enzyme; and
(xi) a luciferin substrate,
wherein (i)-(xi) are in one or more containers.

Clause 33. The kit of clause 32, wherein a first detection reagent comprises:
(v) 3-oxoacid CoA-transfer (SCOT);
(vi) inorganic phosphate; and
(vii) acetoacetyl-CoA; and a second detection reagent comprises:
  (viii) succinyl-CoA ligase (SCS);
  (ix) ADP;
  (x) a bioluminescent enzyme; and
  (xi) a luciferin substrate.

Clause 34. A kit for detecting or determining 2-oxoglutarate oxygenase activity in a sample, the kit comprising:
  (i) a peptide, protein, or non-protein substrate;
  (ii) 2-oxoglutarate;
  (iii) Fe (II);
  (iv) ascorbate;
  (v) GDP forming succinyl-CoA ligase (SCS-GDP);
  (vi) GTP;
  (vii) coenzyme A;
  (viii) guanylate kinase (GMPK);
  (ix) ADP;
  (x) a bioluminescent enzyme; and
  (xi) a luciferin substrate,
wherein (i)-(xi) are in one or more containers.

Clause 35. The kit of clause 34, wherein a first detection reagent comprises:
  (v) GDP forming succinyl-CoA ligase (SCS-GDP);
  (vi) GTP; and
  (vii) coenzyme A; and
a second detection reagent comprises:
  (viii) guanylate kinase (GMPK);
  (ix) ADP;
  (x) a bioluminescent enzyme; and
  (xi) a luciferin substrate.

Clause 36. A kit for detecting or determining 2-oxoglutarate oxygenase activity in a sample, the kit comprising:
  (i) a peptide, protein, or non-protein substrate;
  (ii) 2-oxoglutarate;
  (iii) Fe (II);
  (iv) ascorbate;
  (v) ADP forming succinyl-CoA ligase (SCS-ADP);
  (vi) ATP;
  (vii) coenzyme A;
  (viii) adenylate cyclase;
  (ix) pyrophosphatase;
  (x) pyruvate kinase;
  (xi) phosphoenolpyruvate;
  (xii) a bioluminescent enzyme; and
  (xiii) a luciferin substrate,
wherein (i)-(xiii) are in one or more containers.

Clause 37. The kit of clause 36, wherein a first detection reagent comprises:
  (v) ADP forming succinyl-CoA ligase (SCS-ADP);
  (vi) ATP; and
  (vii) coenzyme A; and
a second detection reagent comprises an ATP depletion reagent and an ADP to ATP conversion/detection reagent, wherein the ATP depletion reagent comprises:
  (viii) adenylate cyclase; and
  (ix) pyrophosphatase; and
the ADP to ATP conversion/detection reagent comprises:
  (x) pyruvate kinase;
  (xi) phosphoenolpyruvate;
  (xii) a bioluminescent enzyme; and
  (xiii) a luciferin substrate.

Clause 38. The kit of any one of clauses 32-37, further comprising instructions for using the kit to detect or determine 2-oxoglutarate oxygenase activity in a sample.

Clause 39. The kit of any one of clauses 32-38, wherein the 2-oxoglutarate oxygenase is a Fe (II) dependent lysine demethylase or a 2-oxoglutarate-dependent dioxygenase.

Clause 40. The kit of clause 39, wherein the Fe (II) dependent lysine demethylases is a JumonjiC domain-containing histone lysine (JMJC) demethylase.

Clause 41. The kit of clause 40, wherein the JMJC demethylase is a member of the KDM3, KDM4, KDM5, or KDM6 family of histone demethylases.

Clause 42. The kit of clause 41, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 43. The kit of clause 42, wherein the JMJC demethylase is JMJD2A or JMJD2C.

Clause 44. The kit of any one of clauses 32-43, wherein the kit comprises a peptide, protein, or non-protein substrate.

Clause 45. The kit of clause 44, wherein the peptide or protein substrate is a histone peptide substrate.

Clause 46. The kit of clause 45, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 47. The kit of any one of clauses 24-46, wherein the bioluminescent enzyme is luciferase.

Clause 48. The kit of clause 47, wherein the luciferase is a recombinant luciferase.

Clause 49. The kit of clause 48, wherein the luciferase is a thermostable and/or a chemostable luciferase.

Clause 50. The kit of clause 49, wherein the luciferase is a thermostable firefly luciferase.

Clause 51. A method for luminescent detection or determination of succinate in a sample, the method comprising:
  (a) contacting the sample with a first detection reagent to form a first reaction mixture;
  (b) contacting the first reaction mixture with a second detection reagent to form a second reaction mixture; and
  (c) detecting luminescence in the second reaction mixture, thereby detecting or determining the presence or amount of succinate in the sample;
wherein if succinate is present in the sample, the first detection reagent and the second detection reagent converts the succinate to ATP.

Clause 52. A method for detecting or determining the presence or amount of succinate in a sample, the method comprising:
  (a) contacting the sample with a first detection reagent to form a first reaction mixture;
  (b) contacting the first reaction mixture with a second detection reagent to form a second reaction mixture; and
  (c) detecting luminescence in the second reaction mixture, thereby detecting or determining the presence or amount of succinate in the sample;
wherein:
  (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;
  (ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate;
  (iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iv) the first detection reagent comprises ADP forming succinyl-CoA ligase (SCS-ADP), ATP, and coenzyme A and the second detection reagent comprises an ATP depletion reagent and subsequently an ADP-to-ATP conversion/detection reagent, wherein the first reaction mixture is contacted sequentially with the ATP depletion reagent and the ADP-to-ATP conversion/detection reagent, and wherein the ATP depletion reagent comprises adenylate cyclase and pyrophosphatase and the ADP-to-ATP conversion/detection reagent comprises pyruvate kinase, phosphoenolpyruvate, a bioluminescent enzyme, and a luciferin substrate.

Clause 53. The method of clause 51 or 52, wherein the first detection reagent comprises 3-oxoacid CoA-transferase (SCOT), inorganic phosphate, and acetoacetyl-CoA and the second detection reagent comprises succinyl-CoA ligase (SCS), ADP, a thermostable firefly luciferase, and D-luciferin.

Clause 54. The method of clause 51 or 52, wherein first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a thermostable firefly luciferase, and D-luciferin.

Clause 55. The method of clause 51 or 52, wherein the first detection reagent comprises GDP forming succinyl-CoA ligase (SCS-GDP), GTP, and coenzyme A and the second detection reagent comprises guanylate kinase (GMPK), ADP, a thermostable firefly luciferase, and D-luciferin.

Clause 56. The method of clause 51 or 52, wherein the first detection reagent comprises ADP forming succinyl-CoA ligase (SCS-ADP), ATP, and coenzyme A and the second detection reagent comprises an ATP depletion reagent and subsequently an ADP-to-ATP conversion/detection reagent, wherein the first reaction mixture is contacted sequentially with the ATP depletion reagent and the ADP-to-ATP conversion/detection reagent, and wherein the ATP depletion reagent comprises adenylate cyclase and pyrophosphatase and the ADP-to-ATP conversion/detection reagent comprises pyruvate kinase, phosphoenolpyruvate, a thermostable firefly luciferase, and D-luciferin.

Clause 57. A method for detecting or determining the presence or amount of a succinate forming enzyme in a sample or the activity of a succinate forming enzyme, the method comprising:

(a) contacting the sample with a peptide, protein, or non-protein substrate, 2-oxoglutarate, Fe(II), and ascorbate to form a succinate reaction mixture, wherein succinate is formed if the sample comprises a succinate forming enzyme;

(b) contacting the succinate reaction mixture with a first detection reagent to form a first reaction mixture, wherein the succinate formed in step (a) is converted to succinyl-CoA;

(c) contacting the first reaction mixture with a second detection reagent to form a second reaction mixture; and (d) detecting luminescence in the second reaction mixture, thereby detecting or determining the presence or amount of succinate forming enzyme or succinate forming enzyme activity in the sample,
wherein:

(i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;

(ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate;

(iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate; or (iv) the first detection reagent comprises ADP forming succinyl-CoA ligase (SCS-ADP), ATP, and coenzyme A and the second detection reagent comprises an ATP depletion reagent and an ADP-to-ATP conversion/detection reagent, wherein the first reaction mixture is contacted sequentially with the ATP depletion reagent and the ADP-to-ATP conversion/detection reagent, wherein the ATP depletion reagent comprises adenylate cyclase and pyrophosphatase, and wherein the ADP-to-ATP conversion/detection reagent comprises pyruvate kinase, phosphoenolpyruvate, a bioluminescent enzyme, and a luciferin substrate.

Clause 58. The method of any one of clauses 51-57, wherein contacting the first reaction mixture with a second detection reagent generates ATP.

Clause 59. The method of clause 57, wherein the succinate forming enzyme is a 2-oxoglutarate oxygenase.

Clause 60. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe(II), and ascorbate to form a succinate reaction mixture;

(c) contacting the succinate reaction mixture with:

i) 3-oxoacid CoA-transferase (SCOT), inorganic phosphate, and acetoacetyl-CoA to form a first reaction mixture, whereby the succinate formed in step (a) is converted to succinyl-CoA; or ii) 3-oxoacid CoA-transferase (SCOT), inorganic phosphate, acetoacetyl-CoA, succinyl-CoA ligase (SCS), ADP, magnesium chloride to form a first reaction mixture, whereby the succinate formed in step (a) is converted to ATP;

(d) contacting the first reaction mixture with an ATP detection reagent to form a second reaction mixture, wherein the ATP detection reagent comprises succinyl-CoA ligase (SCS), ADP, a bioluminescent enzyme, and a luciferin substrate;

(e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

Clause 61. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe(II), and ascorbate to form a succinate reaction mixture;

(c) contacting the succinate reaction mixture with GDP forming succinyl-CoA ligase (SCS-GDP), GTP, and coenzyme A; to form a first reaction mixture, whereby the succinate formed in step (a) is converted to succinyl-CoA and GDP;

(d) contacting the first reaction mixture with an ATP detection reagent to form a second reaction mixture, wherein the ATP detection reagent comprises guanylate kinase (GMPK), ADP, a bioluminescent enzyme, and a luciferin substrate;

(e) detecting luminescence in the second reaction mixture; and (f) comparing the luminescence in the second reaction mixture to luminescence in a control sample, wherein if the luminescence in the second reaction mixture is different from the luminescence in a control sample, the compound is identified as being a modulator of 2-oxoglutarate oxygenase activity.

Clause 62. A method for determining whether a compound modulates 2-oxoglutarate oxygenase activity in a sample, the method comprising:

(a) contacting the sample with the compound to form a test sample, wherein the sample comprises a 2-oxoglutarate oxygenase;

(b) contacting the test sample with a peptide, protein, or non-protein substrate, 2-oxoglutarate, Fe(II), and ascorbate to form a succinate reaction mixture;

(c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP;

(d) contacting the first reaction mixture with an ATP depletion reagent to form a second reaction mixture, wherein the ATP depletion reagent comprises adenylate cyclase and pyrophosphatase;

(e) contacting the second reaction mixture with an ADP-to-ATP conversion/detection reagent to form a third reaction mixture, wherein the ADP-to-ATP conversion/detection reagent comprises pyruvate kinase, phosphoenolpyruvate, a bioluminescent enzyme, and a luciferin substrate;

(f) detecting luminescence in the third reaction mixture; and (g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity.

Clause 63. The method of any one of clauses 59-62, wherein the 2-oxoglutarate oxygenase is a Fe(II)-dependent lysine demethylase or a 2-oxoglutarate-dependent dioxygenase.

Clause 64. The method of clause 63, wherein the Fe(II)-dependent lysine demethylases is a JumonjiC domain-containing histone lysine (JMJC) demethylase.

Clause 65. The method of clause 64, wherein the JMJC demethylase is a member of the KDM3, KDM4, KDM5, or KDM6 family of histone demethylases.

Clause 66. The method of clause 65, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 67. The method of clause 66, wherein the JMJC demethylase is JMJD2A or JMJD2C.

Clause 68. The method of any one of clauses 57-67, wherein the sample is contacted with a peptide, protein, or non-protein substrate.

Clause 69. The method of clause 68, wherein the peptide or protein substrate is a histone peptide substrate.

Clause 70. The method of clause 69, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 71. The method of any one of the preceding clauses, wherein the bioluminescent enzyme is luciferase.

Clause 72. The method of clause 71, wherein the luciferase is a recombinant luciferase.

Clause 73. The method of clause 71, wherein the luciferase is a thermostable and/or a chemostable luciferase.

Clause 74. The method of clause 73, wherein the luciferase is a thermostable firefly luciferase.

Clause 75. A kit for detecting succinate in a sample, the kit comprising:
(i) 3-oxoacid CoA-transferase (SCOT);
(ii) inorganic phosphate;
(iii) acetoacetyl-CoA;
(iv) succinyl-CoA ligase (SCS);
(v) ADP;
(vi) a bioluminescent enzyme; and
(vii) a luciferin substrate,
wherein (i)-(vii) are in one or more containers.

Clause 76. The kit of clause 75, wherein a first detection reagent comprises:
(i) 3-oxoacid CoA-transferase (SCOT);
(ii) inorganic phosphate; and
(iii) acetoacetyl-CoA; and
a second detection reagent comprises:
(iv) succinyl-CoA ligase (SCS);
(v) ADP;
(vi) a bioluminescent enzyme; and
(vii) a luciferin substrate.

Clause 77. The kit of clause 75, wherein a first detection reagent comprises:
(i) 3-oxoacid CoA-transferase (SCOT);
(ii) inorganic phosphate;
(iii) acetoacetyl-CoA;
(iv) succinyl-CoA ligase (SCS);
(v) ADP;
(viii) magnesium chloride and
a second detection reagent comprises:
(vi) a bioluminescent enzyme; and
(vii) a luciferin substrate.

Clause 78. The kit of any one of clauses 75-77, wherein the bioluminescent enzyme is a thermostable firefly luciferase and the luciferin substrate is D-luciferin.

Clause 79. A kit for detecting succinate in a sample, the kit comprising:
(i) GDP forming succinyl-CoA ligase (SCS-GDP);
(ii) GTP;
(iii) coenzyme A;
(iv) guanylate kinase (GMPK);
(v) ADP;
(vi) a bioluminescent enzyme; and
(vii) a luciferin substrate,
wherein (i)-(vii) are in one or more containers.

Clause 80. The kit of clause 79, wherein a first detection reagent comprises:
(i) GDP forming succinyl-CoA ligase (SCS-GDP);
(ii) GTP; and
(iii) coenzyme A; and
a second detection reagent comprises:
(iv) guanylate kinase (GMPK);
(v) ADP;

(vi) a bioluminescent enzyme; and
(vii) a luciferin substrate.

Clause 81. A kit for detecting succinate in a sample, the kit comprising:
(i) ADP forming succinyl-CoA ligase (SCS-ADP);
(ii) ATP;
(iii) coenzyme A;
(iv) adenylate cyclase;
(v) pyrophosphatase;
(vi) pyruvate kinase;
(vii) phosphoenolpyruvate;
(viii) a bioluminescent enzyme; and
(ix) a luciferin substrate,
wherein (i)-(ix) are in one or more containers.

Clause 82. The kit of clause 81, wherein a first detection reagent comprises:
(i) ADP forming succinyl-CoA ligase (SCS-ADP);
(ii) ATP; and
(iii) coenzyme A; and
a second detection reagent comprises an ATP depletion reagent and an ADP-to-ATP conversion/detection reagent, wherein the ATP depletion reagent comprises:
(iv) adenylate cyclase; and
(v) pyrophosphatase; and
the ADP-to-ATP conversion/detection reagent comprises:
(vi) pyruvate kinase;
(vii) phosphoenolpyruvate;
(viii) a bioluminescent enzyme; and
(ix) a luciferin substrate.

Clause 83. The kit of any one of clauses 75-82, further comprising instructions for using the kit to detect or determine the presence or amount of succinate in the sample.

Clause 84. A kit for detecting or determining 2-oxoglutarate oxygenase activity in a sample, the kit comprising:
(i) a peptide, protein, or non-protein substrate;
(ii) 2-oxoglutarate;
(iii) Fe(II);
(iv) ascorbate;
(v) 3-oxoacid CoA-transferase (SCOT);
(vi) inorganic phosphate;
(vii) acetoacetyl-CoA;
(viii) succinyl-CoA ligase (SCS);
(ix) ADP;
(x) a bioluminescent enzyme; and
(xi) a luciferin substrate,
wherein (i)-(xi) are in one or more containers.

Clause 85. The kit of clause 84, wherein a first detection reagent comprises:
(v) 3-oxoacid CoA-transferase (SCOT);
(vi) inorganic phosphate; and
(vii) acetoacetyl-CoA; and
a second detection reagent comprises:
(viii) succinyl-CoA ligase (SCS);
(ix) ADP;
(x) a bioluminescent enzyme; and
(xi) a luciferin substrate.

Clause 86. The kit of clause 84, wherein a first detection reagent comprises:
(v) 3-oxoacid CoA-transferase (SCOT);
(vi) inorganic phosphate;
(vii) acetoacetyl-CoA;
(viii) succinyl-CoA ligase (SCS);
(ix) ADP;
(xii) magnesium chloride and
a second detection reagent comprises:
(x) a bioluminescent enzyme; and
(xi) a luciferin substrate.

Clause 87. A kit for detecting or determining 2-oxoglutarate oxygenase activity in a sample, the kit comprising:
(i) a peptide, protein, or non-protein substrate;
(ii) 2-oxoglutarate;
(iii) Fe(II);
(iv) ascorbate;
(v) GDP forming succinyl-CoA ligase (SCS-GDP);
(vi) GTP;
(vii) coenzyme A;
(viii) guanylate kinase (GMPK);
(ix) ADP;
(x) a bioluminescent enzyme; and
(xi) a luciferin substrate,
wherein (i)-(xi) are in one or more containers.

Clause 88. The kit of clause 87, wherein a first detection reagent comprises:
(v) GDP forming succinyl-CoA ligase (SCS-GDP);
(vi) GTP; and
(vii) coenzyme A; and
a second detection reagent comprises:
(viii) guanylate kinase (GMPK);
(ix) ADP;
(x) a bioluminescent enzyme; and
(xi) a luciferin substrate.

Clause 89. A kit for detecting or determining 2-oxoglutarate oxygenase activity in a sample, the kit comprising:
(i) a peptide, protein, or non-protein substrate;
(ii) 2-oxoglutarate;
(iii) Fe(II);
(iv) ascorbate;
(v) ADP forming succinyl-CoA ligase (SCS-ADP);
(vi) ATP;
(vii) coenzyme A;
(viii) adenylate cyclase;
(ix) pyrophosphatase;
(x) pyruvate kinase;
(xi) phosphoenolpyruvate;
(xii) a bioluminescent enzyme; and
(xiii) a luciferin substrate,
wherein (i)-(xiii) are in one or more containers.

Clause 90. The kit of clause 89, wherein a first detection reagent comprises:
(v) ADP forming succinyl-CoA ligase (SCS-ADP);
(vi) ATP; and
(vii) coenzyme A; and
a second detection reagent comprises an ATP depletion reagent and an ADP-to-ATP conversion/detection reagent, wherein the ATP depletion reagent comprises:
(viii) adenylate cyclase; and
(ix) pyrophosphatase; and
the ADP-to-ATP conversion/detection reagent comprises:
(x) pyruvate kinase;
(xi) phosphoenolpyruvate;
(xii) a bioluminescent enzyme; and
(xiii) a luciferin substrate.

Clause 91. The kit of any one of clauses 84-90, further comprising instructions for using the kit to detect or determine 2-oxoglutarate oxygenase activity in a sample.

Clause 92. The kit of any one of clauses 84-91, wherein the 2-oxoglutarate oxygenase is a Fe(II)-dependent lysine demethylase or a 2-oxoglutarate-dependent dioxygenase.

Clause 93. The kit of clause 92, wherein the Fe(II)-dependent lysine demethylases is a JumonjiC domain-containing histone lysine (JMJC) demethylase.

Clause 94. The kit of clause 93, wherein the JMJC demethylase is a member of the KDM3, KDM4, KDM5, or KDM6 family of histone demethylases.

Clause 95. The kit of clause 94, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 96. The kit of clause 95, wherein the JMJC demethylase is JMJD2A or JMJD2C.

Clause 97. The kit of any one of clauses 84-96, wherein the kit comprises a peptide, protein, or non-protein substrate.

Clause 98. The kit of clause 97, wherein the peptide or protein substrate is a histone peptide substrate.

Clause 99. The kit of clause 98, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 100. The kit of any one of clauses 75-99, wherein the bioluminescent enzyme is luciferase.

Clause 101. The kit of clause 100, wherein the luciferase is a recombinant luciferase.

Clause 102. The kit of clause 101, wherein the luciferase is a thermostable and/or a chemostable luciferase.

Clause 103. The kit of clause 102, wherein the luciferase is a thermostable firefly luciferase.

Clause 104. A method for detecting or determining the presence or amount of succinate in a sample, the method comprising:
(a) contacting the sample with a first detection reagent to form a first reaction mixture;
(b) contacting the first reaction mixture with a second detection reagent to form a second reaction mixture; and
(c) detecting luminescence in the second reaction mixture, thereby detecting or determining the presence or amount of succinate in the sample;
wherein the first detection reagent comprises ADP forming succinyl-CoA ligase (SCS-ADP), ATP, and coenzyme A, and the second detection reagent comprises an ATP depletion reagent and subsequently an ADP-to-ATP conversion/detection reagent, wherein the first reaction mixture is contacted sequentially with the ATP depletion reagent and the ADP-to-ATP conversion/detection reagent; and a bioluminescent enzyme, and a luciferin substrate.

Clause 105. A method for determining whether a compound modulates 2-oxoglutarate oxygenase activity in a sample, the method comprising:
(a) contacting the sample with the compound to form a test sample, wherein the sample comprises a 2-oxoglutarate oxygenase;
(b) contacting the test sample with a peptide, protein, or non-protein substrate, 2-oxoglutarate, Fe(II), and ascorbate to form a succinate reaction mixture;
(c) contacting the succinate reaction mixture with ADP forming succinyl-CoA ligase (SCS-ADP), ATP, and coenzyme A to form a first reaction mixture, whereby the succinate formed in step (a) is converted to succinyl-CoA and ADP;
(d) contacting the first reaction mixture with an ATP depletion reagent to form a second reaction mixture;
(e) contacting the second reaction mixture with an ADP-to-ATP conversion/detection reagent to form a third reaction mixture, wherein the ADP-to-ATP conversion/detection reagent comprises pyruvate kinase, phosphoenolpyruvate, a bioluminescent enzyme, and a luciferin substrate;
(f) detecting luminescence in the third reaction mixture; and
(g) comparing the luminescence in the third reaction mixture to luminescence in a control sample, wherein if the luminescence in the third reaction mixture is different from the luminescence in a control sample, the compound is identified as being a modulator of 2-oxoglutarate oxygenase activity.

Clause 106. The method of clause 104 or 105, wherein the ADP-to-ATP conversion/detection reagent comprises pyruvate kinase, phosphoenolpyruvate, a thermostable firefly luciferase, and D-luciferin.

Clause 107. The method of clause 104 or 105, wherein the ATP depletion reagent comprises (i) adenylate cyclase or ATP sulfurylase and (ii) pyrophosphatase.

Clause 108. The method of any one of clauses 105-107, wherein the 2-oxoglutarate oxygenase is a Fe(II)-dependent lysine demethylase or a 2-oxoglutarate-dependent dioxygenase.

Clause 109. The method of clause 108, wherein the Fe(II)-dependent lysine demethylases is a JumonjiC domain-containing histone lysine (JMJC) demethylase.

Clause 110. The method of clause 109, wherein the JMJC demethylase is a member of the KDM3, KDM4, KDM5, or KDM6 family of histone demethylases.

Clause 111. The method of clause 110, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 112. The method of clause 111, wherein the JMJC demethylase is JMJD2A or JMJD2C.

Clause 113. The method of any one of clauses 105-112, wherein the sample is contacted with a peptide, protein, or non-protein substrate.

Clause 114. The method of clause 113, wherein the peptide or protein substrate is a histone peptide substrate.

Clause 115. The method of clause 114, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 116. The method of any one of the preceding clauses, wherein the bioluminescent enzyme is luciferase.

Clause 117. The method of clause 116, wherein the luciferase is a recombinant luciferase.

Clause 118. The method of clause 116, wherein the luciferase is a thermostable and/or a chemostable luciferase.

Clause 119. The method of clause 118, wherein the luciferase is a thermostable firefly luciferase.

Clause 120. A kit for detecting succinate in a sample, the kit comprising:
(i) ADP forming succinyl-CoA ligase (SCS-ADP);
(ii) ATP;
(iii) coenzyme A;
(iv) an ATP depletion reagent;
(v) an ADP-to-ATP conversion/detection reagent;
(vi) a bioluminescent enzyme; and
(vii) a luciferin substrate,
wherein (i)-(vii) are in one or more containers.

Clause 121. The kit of clause 120, wherein a first detection reagent comprises:
(i) ADP forming succinyl-CoA ligase (SCS-ADP);
(ii) ATP; and
(iii) coenzyme A; and
wherein a second detection reagent comprises (iv) an ATP depletion reagent and (v) an ADP-to-ATP conversion/detection reagent.

Clause 122. The kit of clause 120 or 121, wherein the ADP-to-ATP conversion/detection reagent comprises pyruvate kinase, phosphoenolpyruvate, a bioluminescent enzyme; and a luciferin substrate.

Clause 123. The kit of clause 120 or 121, wherein the ATP depletion reagent comprises (a) adenylate cyclase or ATP sulfurylase and (b) pyrophosphatase.

Clause 124. The kit of any one of clauses 120-123, further comprising instructions for using the kit to detect or determine the presence or amount of succinate in the sample.

Clause 125. A kit for detecting or determining 2-oxoglutarate oxygenase activity in a sample, the kit comprising:
  (i) a peptide, protein, or non-protein substrate;
  (ii) 2-oxoglutarate;
  (iii) Fe(II);
  (iv) ascorbate;
  (v) ADP forming succinyl-CoA ligase (SCS-ADP);
  (vi) ATP;
  (vii) coenzyme A;
  (viii) an ATP depletion reagent;
  (ix) an ATP-to-ATP conversion/detection reagent;
  (x) a bioluminescent enzyme; and
  (xi) a luciferin substrate,
wherein (i)-(xi) are in one or more containers.

Clause 126. The kit of clause 125, wherein a first detection reagent comprises:
  (v) ADP forming succinyl-CoA ligase (SCS-ADP);
  (vi) ATP; and
  (vii) coenzyme A; and
a second detection reagent comprises an ATP depletion reagent and an ADP-to-ATP conversion/detection reagent, wherein the ADP-to-ATP conversion/detection reagent comprises pyruvate kinase, phosphoenolpyruvate, a bioluminescent enzyme; and a luciferin substrate, and wherein the ATP depletion reagent comprises (a) adenylate cyclase or ATP sulfurylase and (b) pyrophosphatase.

Clause 127. The kit of clauses 125-126, further comprising instructions for using the kit to detect or determine 2-oxoglutarate oxygenase activity in a sample.

Clause 128. The kit of any one of clauses 125-127, wherein the 2-oxoglutarate oxygenase is a Fe(II)-dependent lysine demethylase or a 2-oxoglutarate-dependent dioxygenase.

Clause 129. The kit of clause 128, wherein the Fe(II)-dependent lysine demethylases is a JumonjiC domain-containing histone lysine (JMJC) demethylase.

Clause 130. The kit of clause 129, wherein the JMJC demethylase is a member of the KDM3, KDM4, KDM5, or KDM6 family of histone demethylases.

Clause 131. The kit of clause 130, wherein the JMJC demethylase is JMJD1A, JMJD1B, JMJD1C, JMJD2A, JMJD2B, JMJD2C, JMJD2D, JMJD3, JMJD4, JMJD5, or JMJD6.

Clause 132. The kit of clause 131, wherein the JMJC demethylase is JMJD2A or JMJD2C.

Clause 133. The kit of any one of clauses 125-131, wherein the kit comprises a peptide, protein, or non-protein substrate.

Clause 134. The kit of clause 133, wherein the peptide or protein substrate is a histone peptide substrate.

Clause 135. The kit of clause 134, wherein the histone peptide substrate is histone H3 Me3K9, histone H3 Me2K9, histone H3 Me1K9, histone H3 Me3K4, histone H3 Me2K4, histone H3 Me3K27, histone H3 Me2K27, histone H3 Me3K36, or histone H3 Me2K36.

Clause 136. The kit of any one of clauses 120-135, wherein the bioluminescent enzyme is luciferase.

Clause 137. The kit of clause 136, wherein the luciferase is a recombinant luciferase.

Clause 138. The kit of clause 137, wherein the luciferase is a thermostable and/or a chemostable luciferase.

Clause 139. The kit of clause 138, wherein the luciferase is a thermostable firefly luciferase.

Clause 140. The method of any one of clauses 51-119, wherein the sample comprises a cell.

Clause 141. The method of any one of clauses 51-119, wherein the sample comprises a cell lysate.

Clause 142. The method of clause 140 or 141, wherein the cell is a eukaryotic cell or a prokaryotic cell.

Clause 143. The method of any one of clauses 51-119, wherein the sample comprises a tissue sample.

We claim:

1. A method for detecting or determining the presence or amount of succinate in a sample, the method comprising:
  (a) contacting the sample with a first detection reagent to form a first reaction mixture;
  (b) contacting the first reaction mixture with a second detection reagent to form a second reaction mixture; and
  (c) detecting luminescence in the second reaction mixture, thereby detecting or determining the presence or amount of succinate in the sample;
wherein if succinate is present in the sample, the first detection reagent and the second detection reagent converts the succinate to ATP, wherein:
  (i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;
  (ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate; or
  (iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate.

2. The method of claim 1, wherein contacting the first reaction mixture with a second detection reagent generates ATP.

3. The method of claim 1, wherein the sample comprises a cell, a cell lysate, or a tissue sample.

4. The method of claim 1, wherein the bioluminescent enzyme is luciferase and/or the luciferin substrate is D-luciferin.

5. A method for detecting or determining the presence or amount of a succinate forming enzyme in a sample or the activity of a succinate forming enzyme, the method comprising:
  (a) contacting the sample with a peptide, protein, or non-protein substrate, 2-oxoglutarate, Fe(II), and ascorbate to form a succinate reaction mixture, wherein succinate is formed if the sample comprises a succinate forming enzyme;
  (b) contacting the succinate reaction mixture with a first detection reagent to form a first reaction mixture, wherein the succinate formed in step (a) is converted to succinyl-CoA;
  (c) contacting the first reaction mixture with a second detection reagent to form a second reaction mixture; and
  (d) detecting luminescence in the second reaction mixture, thereby detecting or determining the presence or amount of succinate forming enzyme or succinate forming enzyme activity in the sample, wherein:
(i) the first detection reagent comprises 3-oxoacid CoA-transferase (SCOT), inorganic phosphate, and acetoacetyl-CoA and the second detection reagent comprises succinyl-CoA ligase (SCS), ADP, a bioluminescent enzyme, and a luciferin substrate;
(ii) the first detection reagent comprises 3-oxoacid CoA-transferase (SCOT), inorganic phosphate, acetoacetyl-CoA, succinyl-CoA ligase (SCS), ADP, magnesium chloride, and the second detection reagent comprises a bioluminescent enzyme, and a luciferin substrate; or
(iii) the first detection reagent comprises GDP forming succinyl-CoA ligase (SCS-GDP), GTP, and coenzyme A and the second detection reagent comprises guanylate kinase (GMPK), ADP, a bioluminescent enzyme, and a luciferin substrate.

6. The method of claim 5, wherein contacting the first reaction mixture with a second detection reagent generates ATP.

7. The method of claim 5, wherein the succinate forming enzyme is a 2-oxoglutarate oxygenase.

8. The method of claim 7, wherein the 2-oxoglutarate oxygenase is a Fe(II)-dependent lysine demethylase or a 2-oxoglutarate-dependent dioxygenase.

9. The method of claim 8, wherein the Fe(II)-dependent lysine demethylase is a JumonjiC domain-containing histone lysine (JMJC) demethylase.

10. The method of claim 5, wherein the sample comprises a cell, a cell lysate, or a tissue sample.

11. The method of claim 5, wherein the bioluminescent enzyme is luciferase and/or the luciferin substrate is D-luciferin.

12. A method for determining whether a compound modulates 2-oxoglutarate oxygenase activity in a sample, the method comprising:
(a) contacting the sample with the compound to form a test sample, wherein the sample comprises a 2-oxoglutarate oxygenase;
(b) contacting the test sample with a peptide, protein, or non-protein substrate, 2-oxoglutarate, Fe(II), and ascorbate to form a succinate reaction mixture;
(c) contacting the succinate reaction mixture with: a first detection reagent to form a first reaction mixture;
(d) contacting the first reaction mixture with a ATP detection reagent or a second detection reagent to form a second reaction mixture;
(e) contacting the second reaction mixture with a ADP-to-ATP conversion/detection reagent to form a third reaction mixture if a second detection reagent is used in step (d);
(f) detecting luminescence in the second reaction mixture of step (d) or the third reaction mixture of step (e); and
(g) comparing the luminescence in the second reaction mixture of step (d) or the third reaction mixture of step (e) to luminescence in a control sample, wherein if the luminescence in the second reaction mixture of step (d) or the third reaction mixture of step (e) is different from the luminescence in a control sample, the compound is identified as being a modulator of 2-oxoglutarate oxygenase activity, wherein:
(i) the first detection reagent comprises: (A) 3-oxoacid CoA-transferase (SCOT), inorganic phosphate, and acetoacetyl-CoA to form a first reaction mixture, whereby the succinate formed in step (a) is converted to succinyl-CoA; or (B) 3-oxoacid CoA-transferase (SCOT), inorganic phosphate, acetoacetyl-CoA, succinyl-CoA ligase (SCS), ADP, magnesium chloride; and the ATP detection reagent comprises: succinyl-CoA ligase (SCS), ADP, a bioluminescent enzyme, and a luciferin substrate; or
(ii) the first detection reagent comprises: GDP forming succinyl-CoA ligase (SCS-GDP), GTP, and coenzyme A; and the ATP detection reagent comprises: guanylate kinase (GMPK), ADP, a bioluminescent enzyme, and a luciferin substrate.

* * * * *